US007732668B2

(12) United States Patent
Danilevskaya et al.

(10) Patent No.: US 7,732,668 B2
(45) Date of Patent: Jun. 8, 2010

(54) FLORAL DEVELOPMENT GENES

(75) Inventors: Olga Danilevskaya, Johnston, IA (US); Pedro Herman, Johnston, IA (US); Edward Bruggemann, West Des Moines, IA (US); David M Shirbroun, West Des Moines, IA (US); Evgueni Ananiev, Johnston, IA (US); Antoni J Rafalski, Wilmington, DE (US); Hajime Sakai, Newark, DE (US); Edgar B Cahoon, Webster Groves, MO (US); Rebecca E Cahoon, Webster Groves, MO (US); Theodore M Klein, Wilmington, DE (US)

(73) Assignee: Pioneer Hi-Bred International, Inc., Johnston, IA (US)

( * ) Notice: Subject to any disclaimer, the term of this patent is extended or adjusted under 35 U.S.C. 154(b) by 570 days.

(21) Appl. No.: 11/561,462

(22) Filed: Nov. 20, 2006

(65) Prior Publication Data

US 2007/0157341 A1 Jul. 5, 2007

Related U.S. Application Data

(63) Continuation of application No. 10/343,477, filed on Jun. 24, 2003, which is a continuation of application No. PCT/US01/43750, filed on Nov. 21, 2001, now abandoned.

(60) Provisional application No. 60/253,415, filed on Nov. 28, 2000.

(51) Int. Cl.
*C12N 15/29* (2006.01)
*C12N 15/82* (2006.01)
*C12N 15/87* (2006.01)
*A01H 5/00* (2006.01)

(52) U.S. Cl. ...................... 800/298; 536/23.6; 800/278; 435/320.1; 435/419

(58) Field of Classification Search ....................... None
See application file for complete search history.

(56) References Cited

OTHER PUBLICATIONS

Zhang et al (2005, Plant Science 168:1393-1408).*
Kano-Murakami et al (1993, FEBS 334:365-368).*
Bowie et al, Science 247:1306-1310, 1990.*
McConnell et al, Nature 411 (6838):709-713, 2001.*
Cong et al (Jul. 1999, NCBI Accession No. AF159882).*
Ratcliffe et al., (1998, Development 125(9):1609-1615).*
Huang, T., et al.; "The mRNA of the Arabidopsis Gene FT Moves from Leaf to Shoot Apex and Induces Flowering"; Science; Sep. 9, 2005; vol. 39, pp. 1694-1696.
Abe, M., et al; "FD, a bZIP Protein Mediating Signals from the Floral Pathway Integrator FT at the Shoot Apex"; Science; Aug. 12, 2005; vol. 309, pp. 1052-1056.
Wigge, P., et al.; "Integration of Spatial and Temporal Information During Floral Induction in Arabidopsis"; Science; Aug. 12, 2005; vol. 309, pp. 1056-1059.

* cited by examiner

*Primary Examiner*—Stuart F. Baum

(57) ABSTRACT

This invention relates to an isolated nucleic acid fragment encoding floral development proteins, more specifically FT, TFL or Ap3 homologs. The invention also relates to the construction of a recombinant DNA construct encoding all or a portion of the floral development proteins, in sense or antisense orientation, wherein expression of the recombinant DNA construct results in production of altered levels of the FT, TFL or Ap3 homologs in a transformed host cell.

10 Claims, 7 Drawing Sheets

Figure 3:
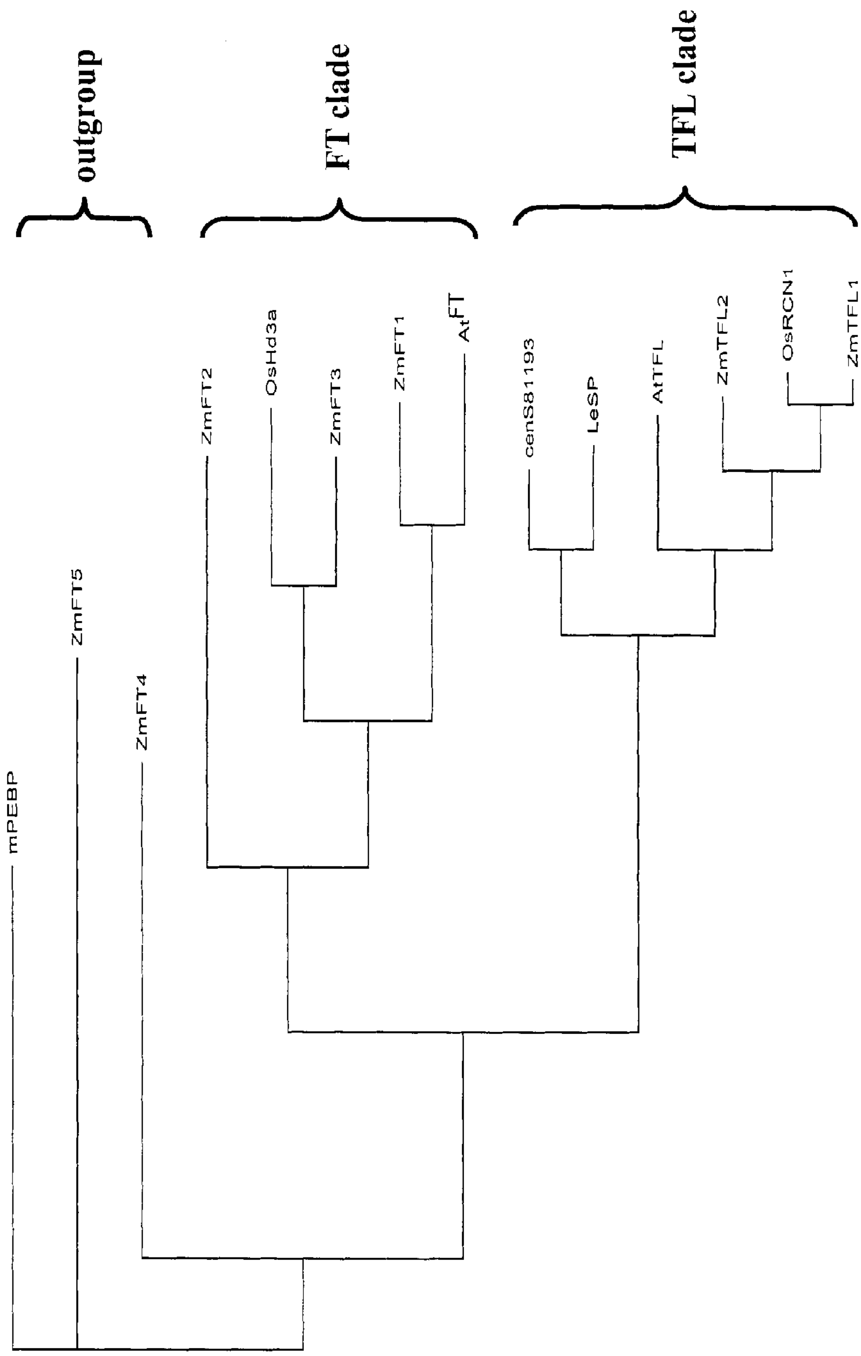

```
                 *       *** **      *   * *                  *    **     *
SEQ ID NO:04     MAM---SV---DPLVVGRVIGDVVDMFVPTANLAVYF-NSKHVTNGCDIKPSLAVNPPRL
SEQ ID NO:06     MSQISASI---DPLIMCRIIGDVVDVFVPTTAMNVYF-GNKHVTNGCNIKPSMAYDAPNV
SEQ ID NO:08     M-------QRGDPLVVGRIIGDVVDPFVRRVPLRVAYAA-REVSNGCELRPSAIADQPRV
SEQ ID NO:10     MA---RFV---DPLVVGRVIGEVVDLFVPSISMTVAYDGSKDISNGCLLKPSATAAPPLV
SEQ ID NO:12     MSR--------DPLVVGNVVGDILDPFIKSASLRVLYNN-RELTNGSEFRPSQVAYEPRI
SEQ ID NO:14     MA---AHV---DPLVVGRVIGDVVDLFVPTVAVSARF-GAKDLTNGCEIKPSVAAAAPAV
SEQ ID NO:16     MSDV-------EPLVLAHVIRDVLDSFAPSIGLRITYNS-RLLLSGVELKPSAVVNKPRV
SEQ ID NO:18     MAGRDR-----EPLVVGRVVGDVLDPFVRTTNLRVSYGA-RTVSNGCELKPSMVVHQPRV
SEQ ID NO:20     MSRS-V-----EPLIVGRVIGEVLDSFNPCVKMIVTYNSNKLVFNGHEIYPSAIVSKPRV
SEQ ID NO:22     MSRV-L-----EPLIVGKVIGEVLDNFNPTVKMTATYGANKQVFNGHEFFPSAVAGKPRV
SEQ ID NO:30     MA---SHV---DPLVVGRVIGDVVDLFVPTTAMSVRF-GTKDLTNGCEIKPSVAAAPPAV
SEQ ID NO:32     MSRV-L-----EPLIVGKVIGEVLDNFNPTVKMTATYGANKQVFNGHEFFPSAVAGKPRV
SEQ ID NO:36     MA---ASV---DPLVVGRVIGDVVDMFIPSVNMSVYF-GSKHVTNGCDIKPSIAISPPKL
SEQ ID NO:38     MARMPL-----EPLIVGRVIGEVLDSFTTSTKMIVSYNKNQ-VYNGHELFPSTVNTKPKV
SEQ ID NO:40     MSRLME-----QPLVVGRVIGEVVDIFSPSVRMNVTYST-KQVANGHELMPSTIMAKPRV
SEQ ID NO:42     MA---AHV---DPLVVGRVIGDVVDMFVPTMPVTVRF-GTKDLTNGCEIKPSIADAAPSI
SEQ ID NO:44     MVGSGMHAQRGDPLVVGRVIGDVVDPFVRRVALRVGYAS-RDVANGCELRPSAIADPPRV
SEQ ID NO:51     MSRS-V-----EPLVVGRVIGEVLDTFNPCMKMIVTYNSNKLVFNGHELYPSAVVSKPRV
                 1                                                          60
```

FIG. 1A

```
                 * *      *   *** * ** *   *  **    **       *      *  * *
SEQ ID NO:04  VIPGH-PRDLYTLVMTDPDAPSPSEPHMREWVHWIIVDIPGGSTMTQGKE-ILPYTGPRP
SEQ ID NO:06  TISGM-PHELYTLVMTDPDAPSPSEPSMREWVHWVVTNIPGGSSAAQGKE-LVSYMGPCP
SEQ ID NO:08  EVGGPDMRTFYTLVMVDPDAPSPSDPNLREYLHWLVTDIPATTGVSFGTE-VVCYESPRP
SEQ ID NO:10  RISGR-RNDLYTLIMTDPDAPSPSNPTMREYLHWIVINIPGGTDATKG-EEVVEYMGPRP
SEQ ID NO:12  EIAGYDMRTLYTLVMVDPDSPSPSNPTKREYLHWLVTDIPESTDVSFGNE-VVSYESPKP
SEQ ID NO:14  LIAGR-ANDLFTLVMTDPDAPSPSEPTMRELLHWLVVNIPGGADASQGGETVVPYVGPRP
SEQ ID NO:16  DVGGTDLRVFYTLVLVDPDAPSPSNPSLREYLHWMVIDIPGTTGASFGQE-LMFYERPEP
SEQ ID NO:18  EVGGPDMRTFYTLVMVDPDAPSPSDPNLREYLHWLVTDIPGTTGAAFGQE-VICYESPRP
SEQ ID NO:20  EVQGGDLRSFFTLVMTDPDVPGPSDPYLREHLHWIVTDIPGTTDASFGRE-VISYESPRP
SEQ ID NO:22  EVQGGDLRSFFTLVMTDPDVPGPSDPYLREHLHWIVTDIPGTTDASFGRE-VVSYESPRP
SEQ ID NO:30  QIAGR-VNELFALVMTDPDAPSPSEPTMREWLHWLVVNIPGGTDPSQG-DVVVPYMGPRP
SEQ ID NO:32  EVQGGDLRSFFTLVMTDPDVPGPSDPYLREHLHWIVTDIPGTTDASFGRE-VVSYESPRP
SEQ ID NO:36  TLTGN-MDNLYTLVMTDPDAPSPSEPSMREWIHWILVDIPGGTNPFRGKE-IVSYVGPRP
SEQ ID NO:38  EIEGGDMRSFFTLIMTDPDVPGPSDPYLREHLHWIVTDIPGTTDATFGKE-LVSYEIPKP
SEQ ID NO:40  EIGGDDMRTAYTLIMTDPDAPSPSDPHLREHLHWTVTDIPGTTDVSFGKE-IVGYESPKP
SEQ ID NO:42  QIAGR-AGDLFTLVMTDPDAPSPSEPTMKEWLHWLVVNIPGGSDPSQG-EEVVPYMGPKP
SEQ ID NO:44  EVGGPDMRTFYTLVMVDPDAPSPSDPSLREYLHWLVTDIPATTGVSFGTE-VVCYEGPRP
SEQ ID NO:51  EVQGGDLRSFFTLVMTDPDVPGPSDPYLREHLHWIVTDIPGTTDASFGRE-VISYESPKP
             61                                                        120
```

FIG. 1B

```
                  ****       *        *         *  *    *     *  * *   ** *
SEQ ID NO:04    PIGIHRYILLLFKQKGPVGL----IEQPP--SRANFSTRLFAKHLDLDLPVAATYFNSQK
SEQ ID NO:06    AIGIHRYILILYRQSIYVDQ---NIEKPNIITRANFSTRAFSHHLCLGVPVATVYFNAQK
SEQ ID NO:08    VLGIHRVVFLLFQQLGRQTVYAPG-------WRQNFSTRDFAELYNLGLPVAAVYFNCQR
SEQ ID NO:10    PVGIHRYVLVLFEQKTRVHAEAPGD-------RANFKTRAFAAAHELGLPTAVVYFNAQK
SEQ ID NO:12    SAGIHRFVFVLVRQSVRQTIYAPG-------WRQNFNTRDFSALYNLGPPVASVFFNCQR
SEQ ID NO:14    PVGIHRYVLVVYQQKARVTAP-PSLAPATEATRARFSNRAFADRHDLGLPVAAMFFNAQK
SEQ ID NO:16    RSGIHRMVFVLFRQLGRGTVFAPD-------MRHNFNCKSFARQYHLDV-VAATYFNCQR
SEQ ID NO:18    TMGIHRFVLVLFQQLGRQTVYAPG-------WRQNFNTRDFAELYNLGPPVAAVYFNCQR
SEQ ID NO:20    NIGIHRFIFVLFKQKGRQTVTVPS-------FRDHFNTRQFAEENDLGLPVAAVYFNAQR
SEQ ID NO:22    NIGIHRFILVLFRQKRRQAVSPPP-------SRDRFSTRQFAEDNDLGLPVAAVYFNAQR
SEQ ID NO:30    PVGIHRYVMVLFQQKARVAAPPPDEDAA----RARFSTRAFADRHDLGLPVAALYFNAQK
SEQ ID NO:32    NIGIHRFILVLFRQKRRQAVSPPP-------SRDRFSTRQFAEDNDLGLPVAAVYFNAQR
SEQ ID NO:36    PIGIHRYIFVLFQQKGPLGL----VEQPP--TRASFNTRYFARQLDLGLPVATVYFNSQK
SEQ ID NO:38    NIGIHRFVFVLFKQKRRQCVTPPT-------SRDHFNTRKFAAENDLALPVAAVYFNAQR
SEQ ID NO:40    VIGIHRYVFILFKQRGRQTVRPPS-------SRDHFNTRRFSEENGLGLPVAVVYFNAQR
SEQ ID NO:42    PLGIHRYVLVLFQQKARVLAPAPGGDTAASAMRARFSTRAFAERHDLGLPVAAMYFNAQK
SEQ ID NO:44    VLGIHRLVFLLFQQLGRQTVYAPG-------WRQNFSTRDFAELYNLGLPVAAVYFNCQR
SEQ ID NO:51    NIGIHRFIFVLFKQKRRQTVIVPS-------FRDHFNTRRFAEENDLGLPVAAVYFNAQR
                121                                                      180
```

FIG. 1C

```
                          *
SEQ ID NO:04              EPATKKFAM-----
SEQ ID NO:06              EPLNQRKNV-----
SEQ ID NO:08              ESGTGGRRM-----
SEQ ID NO:10              EPASRRR-------
SEQ ID NO:12              ENGCGGRRY---IR
SEQ ID NO:14              ETASRRRHY-----
SEQ ID NO:16              EAGSGGRRFRPESS
SEQ ID NO:18              EAGSGGRRM---YS
SEQ ID NO:20              ETA--ARR-----R
SEQ ID NO:22              ETA--ARR-----R
SEQ ID NO:30              EPANRRRRY-----
SEQ ID NO:32              ETA--ARR-----R
SEQ ID NO:36              EPAVKR--R-----
SEQ ID NO:38              ETA--ARR-----R
SEQ ID NO:40              ETA--ARR-----R
SEQ ID NO:42              EPANRRRRY-----
SEQ ID NO:44              ETGTGGRRM-----
SEQ ID NO:51              ETA--ARR-----R
                        181           194
```

FIG. 1D

REPLACEMENT PAGE

```
SEQ ID NO: 68    MgRGKIeIKRIENXTNRQVTySKRRXGiXkKArEltVLCDAXVXiimFSStGKXhXXcSP
                 * **** ****** ****** **** *  *** *  ***** *    *** **     **
SEQ ID NO:46     MGRGKIEIKRIENATNRQVTYSKRRTGIMKKARELTVLCDAQVAIIMFSSTGKYHEFCSP
SEQ ID NO:48     MGRGKIEIKRIENSTNRQVTFSKRRNGILKKAREISVLCDAEVGVVVFSSAGKLYDYCSP
SEQ ID NO:50     MARGKIQIKRIENNTNRQVTYSKRRNGLFKKANELTVLCDAKVSIIMFSSTGKLHQYISP
SEQ ID NO:52     MGRGKIEIKRIENATNRQVTYSKRRTGIMKKARELTVLCDAQVAIIMFSSTGKYHEFCSP
                 1                                                          60

                  *         **    *  **              *  *      * *    *  *  *
SEQ ID NO:46     GTDIKTIFDRYQQAIGTSLWIEQYENMQRTLSHLKDINRGLRTEIRQRMGEDLDSLDFDE
SEQ ID NO:48     KTSLSKILEKYQTNSGKILWGEKHKSLSAEIDRIKKENDTMQIELRHLKGEDLNSLQPKD
SEQ ID NO:50     STSTKQFFDQYQMTLGVDLWNSHYENMQENLKKLKEVNRNLRKEIRQRMGDCLNELGMED
SEQ ID NO:52     STDIKGIFDRYQQAIGTSLWIEQYENMQRTLSHLKDINRNLRTEIRQRMGEDLDGLEFDE
                61                                                          120

                 *   *   *                         *  *
SEQ ID NO:46     LRGLEQNVDAALKEVRHRKYHVISTQTDTYKKKVKHSHE--AYKNLQQELGMR-EDPAFG
SEQ ID NO:48     LIMIEEALDNGLTNLNEKLMEHWERRV-TNTKMMEDENKLLAFKLHQQDIALSGSMRELE
SEQ ID NO:50     LKLLEEEMDKAAKVVRERKYKVITNQIDTQRKKFNNEKE--VHNRLLHDLDAKAEDPRFA
SEQ ID NO:52     LRGLEQNVDAALKEVRHRKYHVITTQTETYKKKVKHSYE--AYETLQQELGLR-EEPAFG
               121                                                          180

                       *  *                *       ** *       *  ***      *
SEQ ID NO:46     YVDNTGAGVAWDGAAAALGGAPPDM-YAFRVVPSQPNLHGMAYG-FHDLR----LG
SEQ ID NO:48     LGYHPD-----------RDLAAQMPITFRVQPSHPNLQENN---------------
SEQ ID NO:50     LIDNGGE----YESVIGFSNLGPRM-FALSIQPSHPSAHSGGAGS--DLTTYPLLF
SEQ ID NO:52     FVDNTGGG--WDGGAGA--GAAADM-FAFRVVPSQPNLHGMAYGGNHDLR----LG
               181                                                      236
```

FIG. 2

Phylogenetic tree of FT-TFL flowering proteins.

FLORAL DEVELOPMENT GENES

APPLICATION PRIORITY INFORMATION

This application is a Continuation of application Ser. No, 10/343,477 filed Jun. 24, 2003 now abandoned, which is a Continuation-In-Part of International Application No. PCT/US01/43750 filed Nov. 21, 2001, which claims the benefit under 35 U.S.C. §119(e) of U.S. Provisional Application 60/253,415 filed Nov. 28, 2000.

FIELD OF THE INVENTION

This invention is in the field of plant molecular biology. More specifically, this invention pertains to nucleic acid fragments encoding floral development proteins in plants and seeds.

BACKGROUND OF THE INVENTION

Flowering in plants is a consequence of the transition of the shoot apex from vegetative to reproductive growth in response to environmental and internal signals. Currently, there is little information about how plants coordinate the activities of the cells that give rise to reproductive plant tissues, however, research has focused on identifying the genes that control this developmental process. Floral homeotic genes that control the specification of meristem and organ identity in developing flowers have been identified in *Arabidopsis thaliana* and *Antirrhinum majus*. Most of these genes belong to a large family of regulatory genes that possess a characteristic DNA binding domain known as the MADS-box. Members of this gene family display primarily floral-specific expression and are homologous to transcription factors found in several animal and fungal species. Molecular evolutionary analysis reveal that there are appreciable differences in the substitution rates between different domains of these plant MADS-box genes. Phylogenetic analysis also demonstrate that members of the plant MADS-box gene family are organized into several distinct gene groups: the AGAMOUS, APETALA3 (Ap3)/PISTILLATA and APETALA1/AGL9 groups. Several genes that belong to the APETALA3 (Ap3) group have been identified in *Arabidopsis thaliana* (Jack, et al., (1992) *Cell* 68:683-697). Genes of this group have been shown to play a role in the control of organ identity of petals and stamens during floral development (Bowman, et al., (1989) *Plant Cell* 1:37-52 and Bowman, et al., (1991) *Development* 112:1-20; Weigel and Meyerowitz (1994) *Cell* 78:203-209; Coen and Meyerowitz (1991) *Nature* 353:31-37; WO 93/21322). Thus, the shared evolutionary history of members of a gene group appear to reflect the distinct functional roles these MAD-box genes play in flower development.

The flowering locus T gene (FT) encodes a protein that appears to be involved in the regulating plant growth by controlling the rate at which maturation occurs. For example, an increase in FT function has been shown to produce early flowering (Kardailsky, et al., (1999) *Science* 286:1962-1965). Thus the FT gene may be useful to accelerate flowering in various crops.

The deduced sequence of the FT protein is similar to the sequence of TERMINAL FLOWER 1 (TFL1) and shares sequence similarity with membrane-associated mammalian proteins (Kardailsky, et al., (1999) *Science* 286:1962-1965). TFL1 in *Arabidopsis*, and the homologous *Antirrhinum* gene CENTRORADIALIS (CEN) play a key role in determining inflorescence architecture (Bradley, et al., (1997) *Science* 275:80-83; WO 97/10339; WO 99/53070).

FT protein belongs to a family of membrane-associated phosphatidylethanolamine-bind proteins (PEBP), which may function as kinase inhibitors to regulate the signal transudation pathways (Kardailsky, et al., (1999) Activation tagging of the floral inducer FT *Science*, December 3; 286 (5446); 1962-5. Also, Kobayashi, et al., (1999). A pair of related genes with antagonistic roles in mediating flowering signals *Science* December 3; 286 (5446); 1960-2.). The *Arabidopsis* gene TFL encodes a protein related to FT. Genes play antagonistic roles in the floral transition such as TFL is a repressor of flowering whereas FT is an activator (Kardailsky, et al., 1999; Kobayashi, et al., 1999). International patent application PCT/US01/43750 claims 9 corn homologs of the *Arabidopsis* FT. For continuity, maize genes were named ZmFT or ZmTFL (Table 1) accordingly to the degree of the translational homology to *Arabidopsis* FT-TFL proteins (GenBank accession numbers FT AB027504, TFL U77674).

There is a great deal of interest in identifying the genes that encode proteins involved in cellular differentiation in plants. These genes may be used in plant cells to control development. Accordingly, the availability of nucleic acid sequences encoding all or a portion of an Ap3 or FT or TFL1 gene homolog would facilitate studies to better understanding development in plants and provide genetic tools to enhance or otherwise alter plant developmental processes. Nucleic acid fragments encoding Ap3 homologs may be useful for engineering plant sterility/fertility, and flower development and morphology. Nucleic acid fragments encoding FT or TFL1 homologs may be useful for engineering flowering time, plant growth rate, inflorescence architecture, and tissue culture morphology and rate of cell division to enhance transformation.

SUMMARY OF THE INVENTION

The present invention concerns isolated polynucleotides comprising a nucleotide sequence encoding a polypeptide having FT, TFL or Ap3 homolog activity wherein the amino acid sequence of the polypeptide and the amino acid sequence of SEQ ID NO: 2, 4, 6, 8, 10, 12, 14, 16, 18, 20, 22, 24, 26, 28, 30, 32, 34, 36, 38, 40, 42, 44, 46, 48, 50, 54, 56, 58 or 60 have at least 80% sequence identity. It is preferred that the identity be at least 85%, it is preferable if the identity is at least 90%, it is more preferred that the identity be at least 95%. The present invention also relates to isolated polynucleotides comprising the complement of the nucleotide sequence, wherein the complement and the nucleotide sequence contain the same number of nucleotides and are 100% complementary. More specifically, the present invention concerns isolated polynucleotides encoding the polypeptide sequence of SEQ ID NO: 2, 4, 6, 8, 10, 12, 14, 16, 18, 20, 22, 24, 26, 28, 30, 32, 34, 36, 38, 40, 42, 44, 46, 48, 50, 54, 56, 58 or 60 or nucleotide sequences comprising the nucleotide sequence of SEQ ID NO: 1, 3, 5, 7, 9, 11, 13, 15, 17, 19, 21, 23, 25, 27, 29, 31, 33, 37, 39, 41, 43, 45, 47, 49, 53, 55, 57, 59, 63, 64, 65, 66 or 67.

In a first embodiment, the present invention concerns an isolated polynucleotide comprising: (a) a nucleotide sequence encoding a polypeptide comprising at least 50, 100, 150, 160, 170, 175 or 200, amino acids, wherein the amino acid sequence of the polypeptide and the amino acid sequence of SEQ ID NO: 2, 4, 6, 8, 10, 12, 14, 16, 18, 20, 22, 24, 26, 28, 30, 32, 34, 36, 38, 40, 42, 44, 46, 48, 50, 54, 56, 58 or 60 have at least 80%, 85%, 90% or 95% identity based on the Clustal alignment method, or (b) the complement of the nucleotide sequence, wherein the complement and the nucleotide sequence contain the same number of nucleotides and are 100% complementary. The polypeptide preferably comprises the amino acid sequence of SEQ ID NO: 2, 4, 6, 8, 10, 12, 14, 16, 18, 20, 22, 24, 26, 28, 30, 32, 34, 36, 38, 40, 42, 44, 46, 48, 50, 54, 56, 58 or 60. The nucleotide sequence preferably comprises the nucleotide sequence of SEQ ID NO: 1, 3, 5, 7, 9, 11, 13, 15, 17, 19, 21, 23, 25, 27, 29, 31, 33, 37, 39, 41, 43, 45, 47, 49, 53, 55, 57, 59, 63, 64, 65, 66 or 67. The polypeptide preferably is a FT, TFL or Ap3 homolog.

In a second embodiment, the present invention relates to a recombinant DNA construct comprising any of the isolated polynucleotides of the present invention operably linked to a regulatory sequence, and a cell, a plant, and a seed comprising the recombinant DNA construct.

In a third embodiment, the present invention relates to a vector comprising any of the isolated polynucleotides of the present invention.

In a fourth embodiment, the present invention relates to an isolated polynucleotide comprising a nucleotide sequence comprised by any of the polynucleotides of the first embodiment, wherein the nucleotide sequence contains at least 30, 40, 50, 60, 100, 150, 160, 170, 175 or 200 nucleotides.

In a fifth embodiment, the present invention relates to a method for transforming a cell comprising transforming a cell with any of the isolated polynucleotides of the present invention, and the cell transformed by this method. Advantageously, the cell is eukaryotic, e.g., a yeast or plant cell, or prokaryotic, e.g., a bacterium.

In a sixth embodiment, the present invention relates to a method for producing a transgenic plant comprising transforming a plant cell with any of the isolated polynucleotides of the present invention and regenerating a plant from the transformed plant cell. The invention also concerns the transgenic plant produced by this method, and the seed obtained from this transgenic plant.

In a seventh embodiment, the present invention concerns an isolated polypeptide comprising an amino acid sequence comprising at least 50, 100, 150, 160, 170, 175 or 200 amino acids, wherein the amino acid sequence and the amino acid sequence of SEQ ID NO: 2, 4, 6, 8, 10, 12, 14, 16, 18, 20, 22, 24, 26, 28, 30, 32, 34, 36, 38, 40, 42, 44, 46, 48, 50, 54, 56, 58 or 60 have at least 80%, 85%, 90% or 95% identity based on the Clustal alignment method. The amino acid sequence preferably comprises the amino acid sequence of SEQ ID NO: 2, 4, 6, 8, 10, 12, 14, 16, 18, 20, 22, 24, 26, 28, 30, 32, 34, 36, 38, 40, 42, 44, 46, 48, 50, 54, 56, 58 or 60. The polypeptide preferably is a FT, TFL or Ap3 homolog.

In an eighth embodiment, the invention concerns a method for isolating a polypeptide encoded by the polynucleotide of the present invention comprising isolating the polypeptide from a cell containing a recombinant DNA construct comprising the polynucleotide operably linked to a regulatory sequence.

In a ninth embodiment, the present invention relates to a virus, preferably a baculovirus, comprising any of the isolated polynucleotides of the present invention or any of the recombinant DNA constructs of the present invention.

In a tenth embodiment, the invention relates to a method of selecting an isolated polynucleotide that affects the level of expression of a gene encoding a FT, TFL or Ap3 homolog protein or activity in a host cell, preferably a plant cell, the method comprising the steps of: (a) constructing an isolated polynucleotide of the present invention or an isolated recombinant DNA construct of the present invention; (b) introducing the isolated polynucleotide or the isolated recombinant DNA construct into a host cell; (c) measuring the level of the FT, TFL or Ap3 homolog protein or activity in the host cell containing the isolated polynucleotide; and (d) comparing the level of the FT, TFL or Ap3 homolog protein or activity in the host cell containing the isolated polynucleotide with the level of the FT, TFL or Ap3 homolog protein or activity in the host cell that does not contain the isolated polynucleotide.

In an eleventh embodiment, the invention concerns a method of obtaining a nucleic acid fragment encoding a substantial portion of a FT, TFL or Ap3 homolog protein, preferably a plant FT, TFL or Ap3 homolog protein comprising the steps of: synthesizing an oligonucleotide primer comprising a nucleotide sequence of at least 30 (preferably at least 40, most preferably at least 60) contiguous nucleotides derived from a nucleotide sequence selected from the group consisting of SEQ ID NO: 1, 3, 5, 7, 9, 11, 13, 15, 17, 19, 21, 23, 25, 27, 29, 31, 33, 37, 39, 41, 43, 45, 47, 49, 53, 55, 57 or 59, and the complement of such nucleotide sequences; and amplifying a nucleic acid fragment (preferably a cDNA inserted in a cloning vector) using the oligonucleotide primer. The amplified nucleic acid fragment preferably will encode a substantial portion of a FT, TFL or Ap3 homolog amino acid sequence.

In a twelfth embodiment, this invention relates to a method of obtaining a nucleic acid fragment encoding all or a substantial portion of the amino acid sequence encoding a FT, TFL or Ap3 homolog protein comprising the steps of: probing a cDNA or genomic library with an isolated polynucleotide of the present invention; identifying a DNA clone that hybridizes with an isolated polynucleotide of the present invention; isolating the identified DNA clone; and sequencing the cDNA or genomic fragment that comprises the isolated DNA clone.

In a thirteenth embodiment, this invention concerns a method for positive selection of a transformed cell comprising: (a) transforming a host cell with the recombinant DNA construct of the present invention or an expression cassette of the present invention; and (b) growing the transformed host cell, preferably a plant cell, such as a monocot or a dicot, under conditions which allow expression of the FT, TFL or Ap3 homolog polynucleotide in an amount sufficient to complement a null mutant, or a conditional null mutant, to provide a positive selection means.

In a fourteenth embodiment, this invention relates to a method of altering the level of expression of a FT, TFL or Ap3 homolog protein in a host cell comprising: (a) transforming a host cell with a recombinant DNA construct of the present invention; and (b) growing the transformed host cell under conditions that are suitable for expression of the recombinant DNA construct wherein expression of the recombinant DNA construct results in production of altered levels of the FT, TFL or Ap3 homolog protein in the transformed host cell.

BRIEF DESCRIPTION OF THE DRAWINGS AND SEQUENCE LISTINGS

The invention can be more fully understood from the following detailed description and the accompanying drawings and Sequence Listing which form a part of this application.

FIG. 1 depicts an alignment of amino acid sequences of FT homologs encoded by nucleotide sequences derived from a contig assembled from balsam pear clones fds.pk0003.h2, fds.pk0026.d10, and fds1n.pk001.p18 (SEQ ID NO: 4), garden balsam clone ids.pk0031.a5 (SEQ ID NO: 6), contig assembled from corn clones cbn10.pk0052.f5, cbn2.pk0035.f12, cco1n.pk0010.h3, p0095.cwsas14f, p0119.cmtmg45rb, and p0128.cpicl42r (SEQ ID NO: 8), corn clone cc71seb.pk0003.h10 (SEQ ID NO: 10), corn clone cco1n.pk0037.d10 (SEQ ID NO: 12), contig assembled from corn clones cen3n.pk0004.e9, cen3n.pk0047.h7, cen3n.pk0093.f1, cen3n.pk0165.f1, and p0120.cdeae63r (SEQ ID NO: 14), corn clone p0014.ctush42r (SEQ ID NO: 16), corn clone p0081.chcad07r (SEQ ID NO: 18), corn clone p0104.cabak14rb (SEQ ID NO: 20), corn clone p0118.chsaq04rb (SEQ ID NO: 22), rice clone rls24.pk0017.c7 (SEQ ID NO: 30), rice clone rr1.pk0043.f9 (SEQ ID NO: 32), contig assembled from soybean clones se3.pk0036.g4 and se6.pk0039.h6 (SEQ ID NO: 36), soybean clone srr2c.pk002.o7 (SEQ ID NO: 38), contig assembled from soybean clone ssl.pk0007.a9 and a PCR fragment sequence (SEQ ID NO: 40), wheat clone wdk2c.pk012.o17 (SEQ ID NO: 42), and wheat clone wdk9n1.pk001.o20 (SEQ ID NO: 44) and *Oryza sativa* (NCBI GI No. 5360178; SEQ ID NO: 51). Amino acids which are conserved among all and at least two sequences with an amino acid at that position are indicated with an asterisk (*). Dashes are used by the program to maximize alignment of the sequences.

FIG. 2 depicts an alignment of amino acid sequences of Ap3 homologs encoded by nucleotide sequences derived from corn clone cta1n.pk0050.f8 (SEQ ID NO: 46), corn clone ctn1c.pk002.j23 (SEQ ID NO: 48), soybean clone sf1n.pk001.l16 (SEQ ID NO: 50), and *Oryza sativa* (NCBI GI No. 5295980; SEQ ID NO: 52). Amino acids which are conserved among all and at least two sequences with an amino acid at that position are indicated with an asterisk (*). Dashes are used by the program to maximize alignment of the sequences.

FIG. 3 delineated a phylogenetic analysis of the family of membrane-associated phosphatidylethanolamine-binding proteins. The phylogenetic tree was constructed by the maximum parsimony methods. The phylogram clearly delimits two major clades that correspond to FT and TFL proteins.

Figure 4:
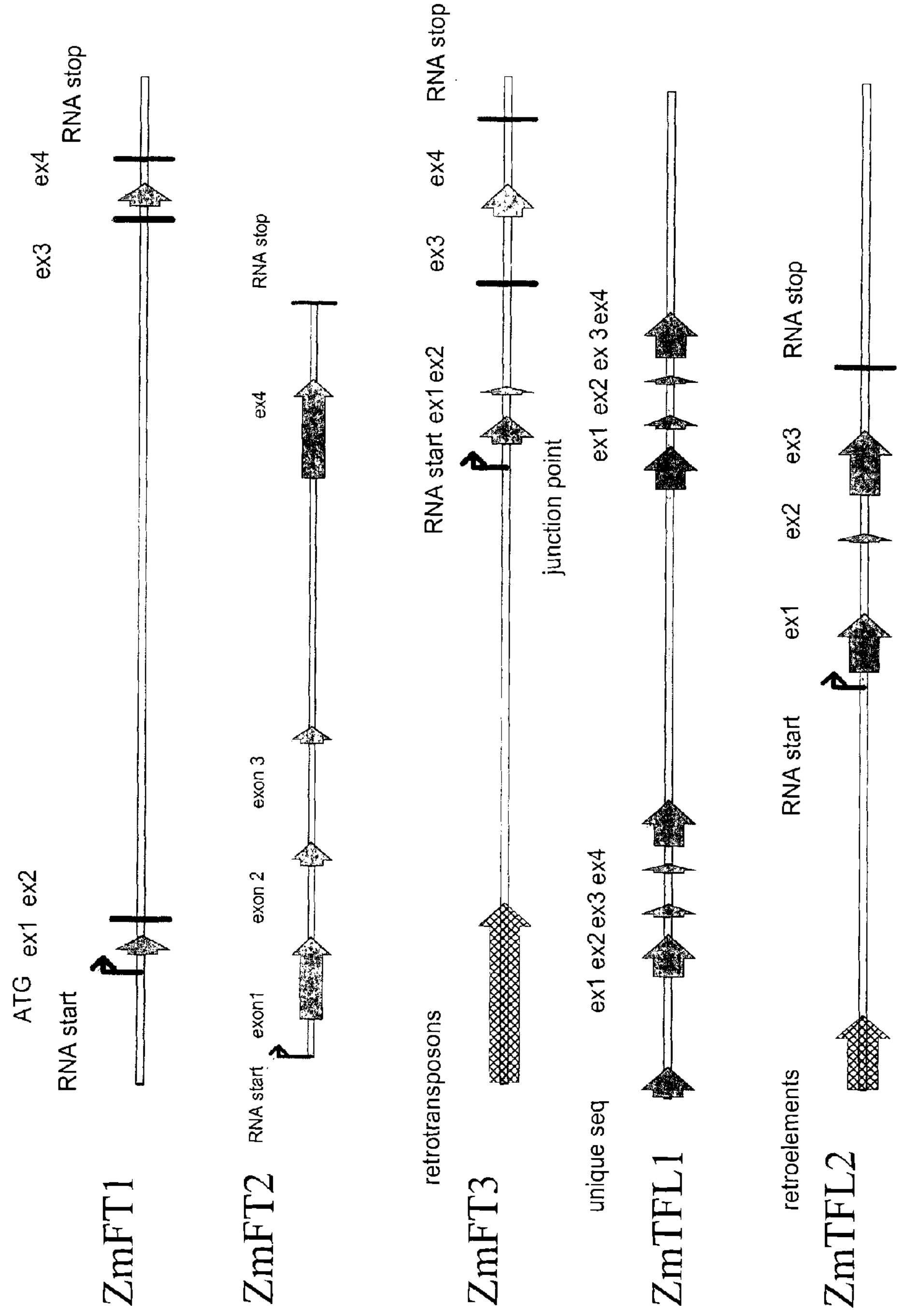

FIG. 4 diagrams the genomic structures of the FT/TFL sequences.

The genomic region of ZmFT1 (SEQ ID NO: 63) is composed of a promoter (1-2211 nt), 5'UTR (2212-2385 nt), exon 1 (2386-3580 nt), exon 2 (2741-2802 nt), exon 3 (9718-9760 nt), exon 4 (9845-10067), 3'UTR (10067-10316).

The genomic region of ZmFT2 (SEQ ID NO: 64) is composed of 5'UTR (1-93), exon1 (94-293), exon2 (468-525), exon3 (765-806), exon 4 (1411-1651), 3'UTR (1652-1840).

The genomic region of ZmFT3 (SEQ ID NO: 65) is composed of a promoter (286-4375nt), 5'UTR (4376-4542 nt), exon 1 (4543-4743 nt), exon 2 (4894-4953 nt), exon 3 (5688-5728 nt), exon 4 (6166-6396 nt), 3'UTR (6397-6860).

The genomic region of ZmTFL1 (SEQ ID NO: 66) is composed of two copies of ZmTFL1 gene arranged in a perfect tandem. The first copy has a partial promoter (1-562 nt), 5'UTR (486-563 nt), exon 1 (564-763 nt), exon 2 (846-9907 nt), exon 3 (1056-1096 nt), exon 4 (1176-1364nt), 3'UTR (1395-1611 nt), 3' downstream segment (1612-2435 nt). The second copy begins from 2436 nt and shows the identical structure as the first one. Genomic organization of ZmTFL1 gene is an example of an unusual configuration of a tandem array of two gene copies. The unit length in tandem is 2292 nt, which include a 5'upstream sequence (364 nt), exon/intron genic segment (1116 nt) and 3'downstream sequence (812 nt). A promoter for the second ZmTFL1 copy may be defined between nucleotides 1611 and 2435 (824 nt total length). Almost identical nucleotide sequences of both units suggest a very recent duplication of ZmTFL1 gene in Mo17 genome.

Genomic region of ZmTFL2 (SEQ ID NO: 67) is composed of a promoter (1-1450 nt), 5'UTR (1451-1518 nt), exon 1 (1519-1780 nt), exon 2 (2097-2137 nt), exon 3 (2309-2595 nt), 3'UTR (2596-2881 nt).

Table 1 lists the polypeptides that are described herein, the designation of the cDNA clones that comprise the nucleic acid fragments encoding polypeptides representing all or a substantial portion of these polypeptides, and the corresponding identifier (SEQ ID NO:) as used in the attached Sequence Listing. The sequence descriptions and Sequence Listing attached hereto comply with the rules governing nucleotide and/or amino acid sequence disclosures in patent applications as set forth in 37 CFR §1.821-1.825.

TABLE 1

Floral Development Proteins

| Protein (Plant Source) | Clone Designation | SEQ ID NO: (Nucleotide) | SEQ ID NO: (Amino Acid) |
|---|---|---|---|
| FT Homolog (Peruvian Lily) | eal1c.pk006.e6 | 1 | 2 |
| FT Homolog (Balsam Pear) | Contig of fds.pk0003.h2 fds.pk0026.d10 fds1n.pk001.p18 | 3 | 4 |
| FT Homolog (Garden Balsam) | ids.pk0031.a5 | 5 | 6 |
| FT Homolog (Corn) | Contig of cbn10.pk0052.f5 cbn2.pk0035.f12 cco1n.pk0010.h3 p0095.cwsas14f p0119.cmtmg45rb p0128.cpicl42r | 7 | 8 |
| FT Homolog (Corn) | cc71se-b.pk0003.h10 | 9 | 10 |
| FT Homolog (Corn) | cco1n.pk0037.d10 | 11 | 12 |
| FT Homolog (Corn) | Contig of cen3n.pk0004.e9 cen3n.pk0047.h7 cen3n.pk0093.f1 cen3n.pk0165.f1 p0120.cdeae63r | 13 | 14 |
| FT Homolog (Corn) | p0014.ctush42r | 15 | 16 |
| FT Homolog (Corn) | p0081.chcad07r | 17 | 18 |
| FT Homolog (Corn) | p0104.cabak14rb | 19 | 20 |
| FT Homolog (Corn) | p0118.chsaq04rb | 21 | 22 |
| FT Homolog (Rice) | rbm1c.pk001.a6 | 23 | 24 |
| FT Homolog (Rice) | Contig of rl0n.pk0022.h10 rl0n.pk0022.h11 | 25 | 26 |
| FT Homolog (Rice) | rlr48.pk0001.b1 | 27 | 28 |
| FT Homolog (Rice) | rls24.pk0017.c7 | 29 | 30 |
| FT Homolog (Rice) | rr1.pk0043.f9 | 31 | 32 |
| FT Homolog (Rice) | rsr9n.pk001.d1 | 33 | 34 |
| FT Homolog (Soybean) | Contig of se3.pk0036.g4 se6.pk0039.h6 | 35 | 36 |
| FT Homolog (Soybean) | srr2c.pk002.o7 | 37 | 38 |
| FT Homolog (Soybean) | Contig of ssl.pk0007.a9 PCR fragment sequence | 39 | 40 |
| FT Homolog (Wheat) | wdk2c.pk012.o17 | 41 | 42 |
| FT Homolog (Wheat) | wdk9n1.pk001.o20 | 43 | 44 |
| Ap3 Homolog (Corn) | cta1n.pk0050.f8 | 45 | 46 |
| Ap3 Homolog (Corn) | ctn1c.pk002.j23 | 47 | 48 |
| Ap3 Homolog (Soybean) | sf1n.pk001.l16 | 49 | 50 |
| FT Homolog (Corn) | cta1n.pk0058.d11b | 53 | 54 |
| FT Homolog (Rice) | rbm1c.pk001.a6:fis | 55 | 56 |
| FT Homolog (Rice) | rl0n.pk0022.h10:fis | 57 | 58 |
| FT Homolog (Rice) | rsr9n.pk001.d1:fis | 59 | 60 |
| FT Homolog (*Arabiopsis*) | | | 61 |

TABLE 1-continued

Floral Development Proteins

| Protein (Plant Source) | Clone Designation | SEQ ID NO: (Nucleotide) | SEQ ID NO: (Amino Acid) |
|---|---|---|---|
| FT Homolog (Rice) | | | 62 |
| FT Homolog (Corn) | | 63 | |
| FT Homolog (Corn | | 64 | |
| FT Homolog (Corn) | | 65 | |
| TFL Homolog (Corn) | | 66 | |
| TFL Homolog (Corn) | | 67 | |

The Sequence Listing contains the one letter code for nucleotide sequence characters and the three letter codes for amino acids as defined in conformity with the IUPAC-IUBMB standards described in *Nucleic Acids Res.* 13:3021-3030 (1985) and in the *Biochemical J.* 219(2):345-373 (1984) which are herein incorporated by reference. The symbols and format used for nucleotide and amino acid sequence data comply with the rules set forth in 37 CFR §1.822.

DETAILED DESCRIPTION OF THE INVENTION

In the context of this disclosure, a number of terms shall be utilized. The terms "polynucleotide", "polynucleotide sequence", "nucleic acid sequence", and "nucleic acid fragment"/"isolated nucleic acid fragment" are used interchangeably herein. These terms encompass nucleotide sequences and the like. A polynucleotide may be a polymer of RNA or DNA that is single- or double-stranded, that optionally contains synthetic, non-natural or altered nucleotide bases. A polynucleotide in the form of a polymer of DNA may be comprised of one or more segments of cDNA, genomic DNA, synthetic DNA, or mixtures thereof. An isolated polynucleotide of the present invention may include at least 30 contiguous nucleotides, preferably at least 40 contiguous nucleotides, most preferably at least 60 contiguous nucleotides derived from SEQ ID NO: 1, 3, 5, 7, 9, 11, 13, 15, 17, 19, 21, 23, 25, 27, 29, 31, 33, 37, 39, 41, 43, 45, 47, 49, 53, 55, 57, 59, 63, 64, 65, 66 or 67 or the complement of such sequences.

The term "isolated" refers to materials, such as nucleic acid molecules and/or proteins, which are substantially free or otherwise removed from components that normally accompany or interact with the materials in a naturally occurring environment. Isolated polynucleotides may be purified from a host cell in which they naturally occur. Conventional nucleic acid purification methods known to skilled artisans may be used to obtain isolated polynucleotides. The term also embraces recombinant polynucleotides and chemically synthesized polynucleotides.

The term "recombinant" means, for example, that a nucleic acid sequence is made by an artificial combination of two otherwise separated segments of sequence, e.g., by chemical synthesis or by the manipulation of isolated nucleic acids by genetic engineering techniques.

As used herein, "contig" refers to a nucleotide sequence that is assembled from two or more constituent nucleotide sequences that share common or overlapping regions of sequence homology. For example, the nucleotide sequences of two or more nucleic acid fragments can be compared and aligned in order to identify common or overlapping sequences. Where common or overlapping sequences exist between two or more nucleic acid fragments, the sequences (and thus their corresponding nucleic acid fragments) can be assembled into a single contiguous nucleotide sequence.

As used herein, "substantially similar" refers to nucleic acid fragments wherein changes in one or more nucleotide bases results in substitution of one or more amino acids, but do not affect the functional properties of the polypeptide encoded by the nucleotide sequence. "Substantially similar" also refers to nucleic acid fragments wherein changes in one or more nucleotide bases does not affect the ability of the nucleic acid fragment to mediate alteration of gene expression by gene silencing through for example antisense or co-suppression technology. "Substantially similar" also refers to modifications of the nucleic acid fragments of the instant invention such as deletion or insertion of one or more nucleotides that do not substantially affect the functional properties of the resulting transcript vis-à-vis the ability to mediate gene silencing or alteration of the functional properties of the resulting protein molecule. It is therefore understood that the invention encompasses more than the specific exemplary nucleotide or amino acid sequences and includes functional equivalents thereof. The terms "substantially similar" and "corresponding substantially" are used interchangeably herein.

Substantially similar nucleic acid fragments may be selected by screening nucleic acid fragments representing subfragments or modifications of the nucleic acid fragments of the instant invention, wherein one or more nucleotides are substituted, deleted and/or inserted, for their ability to affect the level of the polypeptide encoded by the unmodified nucleic acid fragment in a plant or plant cell. For example, a substantially similar nucleic acid fragment representing at least 30 contiguous nucleotides, preferably at least 40 contiguous nucleotides, most preferably at least 60 contiguous nucleotides derived from the instant nucleic acid fragment can be constructed and introduced into a plant or plant cell. The level of the polypeptide encoded by the unmodified nucleic acid fragment present in a plant or plant cell exposed to the substantially similar nucleic fragment can then be compared to the level of the polypeptide in a plant or plant cell that is not exposed to the substantially similar nucleic acid fragment.

For example, it is well known in the art that antisense suppression and co-suppression of gene expression may be accomplished using nucleic acid fragments representing less than the entire coding region of a gene, and by using nucleic acid fragments that do not share 100% sequence identity with the gene to be suppressed. Moreover, alterations in a nucleic acid fragment which result in the production of a chemically equivalent amino acid at a given site, but do not affect the functional properties of the encoded polypeptide, are well known in the art. Thus, a codon for the amino acid alanine, a hydrophobic amino acid, may be substituted by a codon encoding another less hydrophobic residue, such as glycine, or a more hydrophobic residue, such as valine, leucine, or isoleucine. Similarly, changes which result in substitution of one negatively charged residue for another, such as aspartic acid for glutamic acid, or one positively charged residue for another, such as lysine for arginine, can also be expected to produce a functionally equivalent product. Nucleotide changes which result in alteration of the N-terminal and C-terminal portions of the polypeptide molecule would also not be expected to alter the activity of the polypeptide. Each of the proposed modifications is well within the routine skill in the art, as is determination of retention of biological activity of the encoded products. Consequently, an isolated polynucleotide comprising a nucleotide sequence of at least 30 (preferably at least 40, most preferably at least 60) contiguous nucleotides derived from a nucleotide sequence selected from the group consisting of SEQ ID NO: 1, 3, 5, 7, 9, 11, 13, 15, 17, 19, 21, 23, 25, 27, 29, 31, 33, 37, 39, 41, 43, 45, 47, 49, 53, 55, 57, 59, 63, 64, 65, 66 or 67, and the complement of such nucleotide sequences may be used to affect the expression and/or function of a FT, TFL or Ap3 homolog in a host cell. A method of using an isolated polynucleotide to affect the level of expression of a polypeptide in a host cell (eukaryotic, such as plant or yeast, prokaryotic such as bacterial) may comprise the steps of: constructing an isolated polynucleotide of the present invention or an isolated chimeric gene of the present invention; introducing the isolated polynucleotide or the isolated chimeric gene into a host cell; measuring the level of a polypeptide or enzyme activity in the host cell containing the isolated polynucleotide; and comparing the level of a polypeptide or enzyme activity in the host cell containing the isolated polynucleotide with the level of a polypeptide or enzyme activity in a host cell that does not contain the isolated polynucleotide.

Moreover, substantially similar nucleic acid fragments may also be characterized by their ability to hybridize. Estimates of such homology are provided by either DNA-DNA or DNA-RNA hybridization under conditions of stringency as is well understood by those skilled in the art (Hames and Higgins, Eds. (1985) *Nucleic Acid Hybridisation* IRL Press, Oxford, U.K.). Stringency conditions can be adjusted to screen for moderately similar fragments, such as homologous sequences from distantly related organisms, to highly similar fragments, such as genes that duplicate functional enzymes from closely related organisms. Post-hybridization washes determine stringency conditions. One set of preferred conditions uses a series of washes starting with 6×SSC, 0.5% SDS at room temperature for 15 min, then repeated with 2×SSC, 0.5% SDS at 45° C. for 30 min, and then repeated twice with 0.2×SSC, 0.5% SDS at 50° C. for 30 min. A more preferred set of stringent conditions uses higher temperatures in which the washes are identical to those above except for the temperature of the final two 30 min washes in 0.2×SSC, 0.5% SDS was increased to 60° C. Another preferred set of highly stringent conditions uses two final washes in 0.1×SSC, 0.1% SDS at 65° C.

Substantially similar nucleic acid fragments of the instant invention may also be characterized by the percent identity of the amino acid sequences that they encode to the amino acid sequences disclosed herein, as determined by algorithms commonly employed by those skilled in this art. Suitable nucleic acid fragments (isolated polynucleotides of the present invention) encode polypeptides that are at least about 70% identical, preferably at least about 80% identical to the amino acid sequences reported herein. Preferred nucleic acid fragments encode amino acid sequences that are at least about 85% identical to the amino acid sequences reported herein. More preferred nucleic acid fragments encode amino acid sequences that are at least about 90% identical to the amino acid sequences reported herein. Most preferred are nucleic acid fragments that encode amino acid sequences that are at least about 95% identical to the amino acid sequences reported herein. Suitable nucleic acid fragments not only have the above identities but typically encode a polypeptide having at least 50 amino acids, preferably at least 100 amino acids, more preferably at least 150 amino acids, still more preferably at least 200 amino acids, and most preferably at least 250 amino acids. Sequence alignments and percent identity calculations were performed using the Megalign program of the LASERGENE bioinformatics computing suite (DNASTAR Inc., Madison, Wis.). Multiple alignment of the sequences was performed using the Clustal method of alignment (Higgins and Sharp (1989) *CABIOS* 5:151-153) with the default parameters (GAP PENALTY=10, GAP LENGTH PENALTY=10). Default parameters for pairwise alignments using the Clustal method were KTUPLE 1, GAP PENALTY=3, WINDOW=5 and DIAGONALS SAVED=5.

A "substantial portion" of an amino acid or nucleotide sequence comprises an amino acid or a nucleotide sequence that is sufficient to afford putative identification of the protein or gene that the amino acid or nucleotide sequence comprises. Amino acid and nucleotide sequences can be evaluated either manually by one skilled in the art, or by using computer-based sequence comparison and identification tools that employ algorithms such as BLAST (Basic Local Alignment Search Tool; Altschul, et al., (1993) *J. Mol. Biol.* 215:403-410; see also, the explanation of the BLAST algorithm on the world wide web site for the National Center for Biotechnology Information at the National Library of Medicine of the National Institutes of Health). In general, a sequence of ten or more contiguous amino acids or thirty or more contiguous nucleotides is necessary in order to putatively identify a polypeptide or nucleic acid sequence as homologous to a known protein or gene. Moreover, with respect to nucleotide sequences, gene-specific oligonucleotide probes comprising 30 or more contiguous nucleotides may be used in sequence-dependent methods of gene identification (e.g., Southern hybridization) and isolation (e.g., in situ hybridization of bacterial colonies or bacteriophage plaques). In addition, short oligonucleotides of 12 or more nucleotides may be used as amplification primers in PCR in order to obtain a particular nucleic acid fragment comprising the primers. Accordingly, a "substantial portion" of a nucleotide sequence comprises a nucleotide sequence that will afford specific identification and/or isolation of a nucleic acid fragment comprising the sequence. The instant specification teaches amino acid and nucleotide sequences encoding polypeptides that comprise one or more particular plant proteins. The skilled artisan, having the benefit of the sequences as reported herein, may now use all or a substantial portion of the disclosed sequences for purposes known to those skilled in this art. Accordingly, the instant invention comprises the complete sequences as reported in the accompanying Sequence Listing, as well as substantial portions of those sequences as defined above.

"Codon degeneracy" refers to divergence in the genetic code permitting variation of the nucleotide sequence without effecting the amino acid sequence of an encoded polypeptide. Accordingly, the instant invention relates to any nucleic acid fragment comprising a nucleotide sequence that encodes all or a substantial portion of the amino acid sequences set forth herein. The skilled artisan is well aware of the "codon-bias" exhibited by a specific host cell in usage of nucleotide codons to specify a given amino acid. Therefore, when synthesizing a nucleic acid fragment for improved expression in a host cell, it is desirable to design the nucleic acid fragment such that its frequency of codon usage approaches the frequency of preferred codon usage of the host cell.

"Synthetic nucleic acid fragments" can be assembled from oligonucleotide building blocks that are chemically synthesized using procedures known to those skilled in the art. These building blocks are ligated and annealed to form larger nucleic acid fragments which may then be enzymatically assembled to construct the entire desired nucleic acid fragment. "Chemically synthesized", as related to a nucleic acid fragment, means that the component nucleotides were assembled in vitro. Manual chemical synthesis of nucleic acid fragments may be accomplished using well established procedures, or automated chemical synthesis can be performed using one of a number of commercially available machines.

Accordingly, the nucleic acid fragments can be tailored for optimal gene expression based on optimization of the nucleotide sequence to reflect the codon bias of the host cell. The skilled artisan appreciates the likelihood of successful gene expression if codon usage is biased towards those codons favored by the host. Determination of preferred codons can be based on a survey of genes derived from the host cell where sequence information is available.

"Gene" refers to a nucleic acid fragment that expresses a specific protein, including regulatory sequences preceding (5' non-coding sequences) and following (3' non-coding sequences) the coding sequence. "Native gene" refers to a gene as found in nature with its own regulatory sequences. "Chimeric gene" refers any gene that is not a native gene, comprising regulatory and coding sequences that are not found together in nature. Accordingly, a chimeric gene may comprise regulatory sequences and coding sequences that are derived from different sources, or regulatory sequences and coding sequences derived from the same source, but arranged in a manner different than that found in nature. "Endogenous gene" refers to a native gene in its natural location in the genome of an organism. A "foreign-gene" refers to a gene not normally found in the host organism, but that is introduced into the host organism by gene transfer. Foreign genes can comprise native genes inserted into a non-native organism, or chimeric genes. A "transgene" is a gene that has been introduced into the genome by a transformation procedure.

"Coding sequence" refers to a nucleotide sequence that codes for a specific amino acid sequence. "Regulatory sequences" refer to nucleotide sequences located upstream (5' non-coding sequences), within, or downstream (3' non-coding sequences) of a coding sequence, and which influence the transcription, RNA processing or stability, or translation of the associated coding sequence. Regulatory sequences may include promoters, translation leader sequences, introns, and polyadenylation recognition sequences.

"Promoter" refers to a nucleotide sequence capable of controlling the expression of a coding sequence or functional RNA. In general, a coding sequence is located 3' to a promoter sequence. The promoter sequence consists of proximal and more distal upstream elements, the latter elements often referred to as enhancers. Accordingly, an "enhancer" is a nucleotide sequence which can stimulate promoter activity and may be an innate element of the promoter or a heterologous element inserted to enhance the level or tissue-specificity of a promoter. Promoters may be derived in their entirety from a native gene, or may be composed of different elements derived from different promoters found in nature, or may even comprise synthetic nucleotide segments. It is understood by those skilled in the art that different promoters may direct the expression of a gene in different tissues or cell types, or at different stages of development, or in response to different environmental conditions. Promoters which cause a nucleic acid fragment to be expressed in most cell types at most times are commonly referred to as "constitutive promoters". New promoters of various types useful in plant cells are constantly being discovered; numerous examples may be found in the compilation by Okamuro and Goldberg (1989) *Biochemistry of Plants* 15:1-82. It is further recognized that since in most cases the exact boundaries of regulatory sequences have not been completely defined, nucleic acid fragments of different lengths may have identical promoter activity.

"Translation leader sequence" refers to a nucleotide sequence located between the promoter sequence of a gene and the coding sequence. The translation leader sequence is present in the fully processed mRNA upstream of the translation start sequence. The translation leader sequence may affect processing of the primary transcript to mRNA, mRNA stability or translation efficiency. Examples of translation leader sequences have been described (Turner and Foster (1995) *Mol. Biotechnol.* 3:225-236).

"3' non-coding sequences" refer to nucleotide sequences located downstream of a coding sequence and include polyadenylation recognition sequences and other sequences encoding regulatory signals capable of affecting mRNA processing or gene expression. The polyadenylation signal is usually characterized by affecting the addition of polyadenylic acid tracts to the 3' end of the mRNA precursor. The use of different 3' non-coding sequences is exemplified by Ingelbrecht, et al., (1989) *Plant Cell* 1:671-680.

"RNA transcript" refers to the product resulting from RNA polymerase-catalyzed transcription of a DNA sequence. When the RNA transcript is a perfect complementary copy of the DNA sequence, it is referred to as the primary transcript or it may be a RNA sequence derived from post-transcriptional processing of the primary transcript and is referred to as the mature RNA. "Messenger RNA (mRNA)" refers to the RNA that is without introns and that can be translated into polypeptides by the cell. "cDNA" refers to DNA that is complementary to and derived from an mRNA template. The cDNA can be single-stranded or converted to double stranded form using, for example, the Klenow fragment of DNA polymerase I. "Sense-RNA" refers to an RNA transcript that includes the mRNA and so can be translated into a polypeptide by the cell. "Antisense RNA" refers to an RNA transcript that is complementary to all or part of a target primary transcript or mRNA and that blocks the expression of a target gene (see, U.S. Pat. No. 5,107,065, incorporated herein by reference). The complementarity of an antisense RNA may be with any part of the specific nucleotide sequence, i.e., at the 5' non-coding sequence, 3' non-coding sequence, introns, or the coding sequence. "Functional RNA" refers to sense RNA, antisense RNA, ribozyme RNA, or other RNA that may not be translated but yet has an effect on cellular processes.

The term "operably linked" refers to the association of two or more nucleic acid fragments on a single polynucleotide so that the function of one is affected by the other. For example, a promoter is operably linked with a coding sequence when it is capable of affecting the expression of that coding sequence (i.e., that the coding sequence is under the transcriptional control of the promoter). Coding sequences can be operably linked to regulatory sequences in sense or antisense orientation.

The term "expression", as used herein, refers to the transcription and stable accumulation of sense (mRNA) or antisense RNA derived from the nucleic acid fragment of the invention. Expression may also refer to translation of mRNA into a polypeptide. "Antisense inhibition" refers to the production of antisense RNA transcripts capable of suppressing the expression of the target protein. "Overexpression" refers to the production of a gene product in transgenic organisms that exceeds levels of production in normal or non-transformed organisms. "Co-suppression" refers to the production of sense RNA transcripts capable of suppressing the expression of identical or substantially similar foreign or endogenous genes (U.S. Pat. No. 5,231,020, incorporated herein by reference).

A "protein" or "polypeptide" is a chain of amino acids arranged in a specific order determined by the coding sequence in a polynucleotide encoding the polypeptide. Each protein or polypeptide has a unique function.

"Altered levels" or "altered expression" refers to the production of gene product(s) in transgenic organisms in amounts or proportions that differ from that of normal or non-transformed organisms.

"Mature protein" or the term "mature" when used in describing a protein refers to a post-translationally processed polypeptide; i.e., one from which any pre- or propeptides present in the primary translation product have been removed. "Precursor protein" or the term "precursor" when used in describing a protein refers to the primary product of translation of mRNA; i.e., with pre- and propeptides still present. Pre- and propeptides may be but are not limited to intracellular localization signals.

A "chloroplast transit peptide" is an amino acid sequence which is translated in conjunction with a protein and directs the protein to the chloroplast or other plastid types present in the cell in which the protein is made. "Chloroplast transit sequence" refers to a nucleotide sequence that encodes a chloroplast transit peptide. A "signal peptide" is an amino acid sequence which is translated in conjunction with a protein and directs the protein to the secretory system (Chrispeels (1991) *Ann. Rev. Plant Phys. Plant Mol. Biol.* 42:21-53). If the protein is to be directed to a vacuole, a vacuolar targeting signal (supra) can further be added, or if to the endoplasmic reticulum, an endoplasmic reticulum retention signal (supra) may be added. If the protein is to be directed to the nucleus, any signal peptide present should be removed and instead a nuclear localization signal included (Raikhel (1992) *Plant Phys.* 100:1627-1632).

"Transformation" refers to the transfer of a nucleic acid fragment into the genome of a host organism, resulting in genetically stable inheritance. Host organisms containing the transformed nucleic acid fragments are referred to as "transgenic" organisms. Examples of methods of plant transformation include *Agrobacterium*-mediated transformation (De Blaere, et al., (1987) *Meth. Enzymol.* 143:277) and particle-accelerated or "gene gun" transformation technology (Klein, et al., (1987) *Nature* (London) 327:70-73; U.S. Pat. No. 4,945,050, incorporated herein by reference). Thus, isolated polynucleotides of the present invention can be incorporated into recombinant constructs, typically DNA constructs, capable of introduction into and replication in a host cell. Such a construct can be a vector that includes a replication system and sequences that are capable of transcription and translation of a polypeptide-encoding sequence in a given host cell. A number of vectors suitable for stable transfection of plant cells or for the establishment of transgenic plants have been described in, e.g., Pouwels, et al., *Cloning Vectors: A Laboratory Manual* (1985 supp. 1987); Weissbach and Weissbach, *Methods for Plant Molecular Biology* Academic Press (1989); and Flevin, et al., *Plant Molecular Biology Manual* Kluwer Academic Publishers (1990). Typically, plant expression vectors include, for example, one or more cloned plant genes under the transcriptional control of 5' and 3' regulatory sequences and a dominant selectable marker. Such plant expression vectors also can contain a promoter regulatory region (e.g., a regulatory region controlling inducible or constitutive, environmentally- or developmentally-regulated, or cell- or tissue-specific expression), a transcription initiation start site, a ribosome binding site, an RNA processing signal, a transcription termination site, and/or a polyadenylation signal.

Standard recombinant DNA and molecular cloning techniques used herein are well known in the art and are described more fully in Sambrook, et al., *Molecular Cloning: A Laboratory Manual* Cold Spring Harbor Laboratory Press, Cold Spring Harbor (1989) (hereinafter "Maniatis").

"PCR" or "polymerase chain reaction" is well known by those skilled in the art as a technique used for the amplification of specific DNA segments (U.S. Pat. Nos. 4,683,195 and 4,800,159).

The present invention concerns an isolated polynucleotide comprising a nucleotide sequence encoding a FT, TFL or Ap3 homolog polypeptide having at least 80%, 85%, 90%, 95%, or 100% identity, based on the Clustal method of alignment, when compared to a polypeptide selected from the group consisting of SEQ ID NO: 2, 4, 6, 8, 10, 12, 14, 16, 18, 20, 22, 24, 26, 28, 30, 32, 34, 36, 38, 40, 42, 44, 46, 48, 50, 54, 56, 58 or 60.

This invention also relates to the isolated complement of such polynucleotides, wherein the complement and the polynucleotide consist of the same number of nucleotides, and the nucleotide sequences of the complement and the polynucleotide have 100% complementarity.

Nucleic acid fragments encoding at least a portion of several floral development proteins have been isolated and identified by comparison of random plant cDNA sequences to public databases containing nucleotide and protein sequences using the BLAST algorithms well known to those skilled in the art. The nucleic acid fragments of the instant invention may be used to isolate cDNAs and genes encoding homologous proteins from the same or other plant species. Isolation of homologous genes using sequence-dependent protocols is well known in the art. Examples of sequence-dependent protocols include, but are not limited to, methods of nucleic acid hybridization, and methods of DNA and RNA amplification as exemplified by various uses of nucleic acid amplification technologies (e.g., polymerase chain reaction, ligase chain reaction).

For example, genes encoding other FT, TFL or Ap3 homolog, either as cDNAs or genomic DNAs, could be isolated directly by using all or a portion of the instant nucleic acid fragments as DNA hybridization probes to screen libraries from any desired plant employing methodology well known to those skilled in the art. Specific oligonucleotide probes based upon the instant nucleic acid sequences can be designed and synthesized by methods known in the art (Maniatis). Moreover, an entire sequence can be used directly to synthesize DNA probes by methods known to the skilled artisan such as random primer DNA labeling, nick translation, end-labeling techniques, or RNA probes using available in vitro transcription systems. In addition, specific primers can be designed and used to amplify a part or all of the instant sequences. The resulting amplification products can be labeled directly during amplification reactions or labeled after amplification reactions, and used as probes to isolate full length cDNA or genomic fragments under conditions of appropriate stringency.

In addition, two short segments of the instant nucleic acid fragments may be used in polymerase chain reaction protocols to amplify longer nucleic acid fragments encoding homologous genes from DNA or RNA. The polymerase chain reaction may also be performed on a library of cloned nucleic acid fragments wherein the sequence of one primer is derived from the instant nucleic acid fragments, and the sequence of the other primer takes advantage of the presence of the polyadenylic acid tracts to the 3' end of the mRNA precursor encoding plant genes. Alternatively, the second primer sequence may be based upon sequences derived from the cloning vector. For example, the skilled artisan can follow the RACE protocol (Frohman, et al., (1988) *Proc. Natl. Acad. Sci. USA* 85:8998-9002) to generate cDNAs by using PCR to amplify copies of the region between a single point in the transcript and the 3' or 5' end. Primers oriented in the 3' and 5' directions can be designed from the instant sequences. Using commercially available 3' RACE or 5' RACE systems (BRL), specific 3' or 5' cDNA fragments can be isolated (Ohara, et al., (1989) *Proc. Natl. Acad. Sci. USA* 86:5673-5677; Loh, et al., (1989) *Science* 243:217-220). Products generated by the 3' and 5' RACE procedures can be combined to generate full-length cDNAs (Frohman and Martin (1989) *Techniques* 1:165). Consequently, a polynucleotide comprising a nucleotide sequence of at least 30 (preferably at least 40, most preferably at least 60) contiguous nucleotides derived from a nucleotide sequence selected from the group consisting of SEQ ID NO: 1, 3, 5, 7, 9, 11, 13, 15, 17, 19, 21, 23, 25, 27, 29, 31, 33, 37, 39, 41, 43, 45, 47, 49, 53, 55, 57, 59, 63, 64, 65, 66 or 67 and the complement of such nucleotide sequences may be used in such methods to obtain a nucleic acid fragment encoding a substantial portion of an amino acid sequence of a polypeptide.

Availability of the instant nucleotide and deduced amino acid sequences facilitates immunological screening of cDNA expression libraries. Synthetic peptides representing portions of the instant amino acid sequences may be synthesized. These peptides can be used to immunize animals to produce polyclonal or monoclonal antibodies with specificity for peptides or proteins comprising the amino acid sequences. These antibodies can be then be used to screen cDNA expression libraries to isolate full-length cDNA clones of interest (Lerner (1984) *Adv. Immunol.* 36:1-34; Maniatis).

In another embodiment, this invention concerns viruses and host cells comprising either the chimeric genes of the invention as described herein or an isolated polynucleotide of the invention as described herein. Examples of host cells which can be used to practice the invention include, but are not limited to, yeast, bacteria, and plants.

As was noted above, the nucleic acid fragments of the instant invention may be used to create transgenic plants in which the disclosed polypeptides are present at higher or lower levels than normal or in cell types or developmental stages in which they are not normally found. This would have the effect of altering floral development and/or axillary meristems in transgenic plants. For instance, FT is an activator of flowering, while FT-like proteins (TFL) are repressor of flowering. Inhibition of TFL, or over-expression of FT, by chemical treatment, co-suppression, or mutation leads to a proliferation of flower formation which is useful for seed yield in crops such as corn, soybean, rice, and wheat. Over-expression of TFL, or inhibition of FT, suppresses flower formation which is useful for crops such as spinach or lettuce where leaves are desired and seed formation is not. The use of conditional promoters to control FT or TFL expression allows one to control the timing of flower formation, to delay flowering when vegetative growth is advantageous, or accelerate flowering in breeding where reduced generation time is desired. AP3 is required for the determination of the second and third whorls of the floral meristem which give rise to the petals and stamen. Suppression of AP3 has the effect of creating male-sterile flowers, which is advantageous in crops such as corn where outcrossing can lead to hybrid vigor. Induction of male-sterility in self-pollinating plants such as tomato has great commercial value in terms of breeding.

Overexpression of the proteins of the instant invention may be accomplished by first constructing a chimeric gene in which the coding region is operably linked to a promoter capable of directing expression of a gene in the desired tissues at the desired stage of development. The chimeric gene may comprise promoter sequences and translation leader sequences derived from the same genes. 3' Non-coding sequences encoding transcription termination signals may also be provided. The instant chimeric gene may also comprise one or more introns in order to facilitate gene expression.

Plasmid vectors comprising the instant isolated polynucleotide (or chimeric gene) may be constructed. The choice of plasmid vector is dependent upon the method that will be used to transform host plants. The skilled artisan is well aware of the genetic elements that must be present on the plasmid vector in order to successfully transform, select and propagate host cells containing the chimeric gene. The skilled artisan will also recognize that different independent transformation events will result in different levels and patterns of expression (Jones, et al., (1985) *EMBO J.* 4:2411-2418; De Almeida, et al., (1989) *Mol. Gen. Genetics* 218:78-86), and thus that multiple events must be screened in order to obtain lines displaying the desired expression level and pattern. Such screening may be accomplished by Southern analysis of DNA, Northern analysis of mRNA expression, Western analysis of protein expression, or phenotypic analysis.

For some applications it may be useful to direct the instant polypeptides to different cellular compartments, or to facilitate its secretion from the cell. It is thus envisioned that the chimeric gene described above may be further supplemented by directing the coding sequence to encode the instant polypeptides with appropriate intracellular targeting sequences such as transit sequences (Keegstra (1989) *Cell* 56:247-253), signal sequences or sequences encoding endoplasmic reticulum localization (Chrispeels (1991) *Ann. Rev. Plant Phys. Plant Mol. Biol.* 42:21-53), or nuclear localization signals (Raikhel (1992) *Plant Phys.* 100:1627-1632) with or without removing targeting sequences that are already present. While the references cited give examples of each of these, the list is not exhaustive and more targeting signals of use may be discovered in the future.

Gene or Trait Stacking

In certain embodiments the nucleic acid sequences of the present invention can be stacked with any combination of polynucleotide sequences of interest in order to create plants with a desired phenotype. For example, the polynucleotides of the present invention may be stacked with any other polynucleotides of the present invention, such as any combination of ZmFT1, ZmFT2, and ZmFT3 (SEQ ID NOS: 63, 64, and 65), or with other genes implicated in flower development pathways such as ZmTFL1 or ZmTFL2 (SEQ ID NOS: 66 and 67). The combinations generated can also include multiple copies of any one of the polynucleotides of interest. The polynucleotides of the present invention can also be stacked with any other gene or combination of genes to produce plants with a variety of desired trait combinations including but not limited to traits desirable for animal feed such as high oil genes (e.g., U.S. Pat. No. 6,232,529); balanced amino acids (e.g., hordothionins (U.S. Pat. Nos. 5,990,389; 5,885,801; 5,885,802; and 5,703,409); barley high lysine (Williamson, et al., (1987) *Eur. J. Biochem.* 165:99-106; and WO 98/20122); and high methionine proteins (Pedersen, et al., (1986) *J. Biol. Chem.* 261:6279; Kirihara, et al., (1988) *Gene* 71:359; and Musumura, et al., (1989) *Plant Mol. Biol.* 12:123)); increased digestibility (e.g., modified storage proteins (U.S. Provisional Application Ser. No. 60,246,455, filed Nov. 11, 2000); and thioredoxins (U.S. Provisional Application Ser. No. 60/250,705, filed Dec. 12, 2000)), the disclosures of which are herein incorporated by reference. The polynucleotides of the present invention can also be stacked with traits desirable for insect, disease or herbicide resistance (e.g., *Bacillus thuringiensis* toxic proteins (U.S. Pat. Nos. 5,366,892; 5,747, 450; 5,737,514; 5723,756; 5,593,881; Geiser, et al., (1986)

*Gene* 48:109); lectins (Van Damme, et al., (1994) *Plant Mol. Biol.* 24:825); fumonisin detoxification genes (U.S. Pat. No. 5,792,931); avirulence and disease resistance genes (Jones, et al., (1994) *Science* 266:789; Martin, et al., (1993) *Science* 262:1432; Mindrinos, et al., (1994) *Cell* 78:1089); acetolactate synthase (ALS) mutants that lead to herbicide resistance such as the S4 and/or Hra mutations; inhibitors of glutamine synthase such as phosphinothricin or basta (e.g., bar gene); and glyphosate resistance (EPSPS gene)); and traits desirable for processing or process products such as high oil (e.g., U.S. Pat. No. 6,232,529); modified oils (e.g., fatty acid desaturase genes (U.S. Pat. No. 5,952,544; WO 94/11516)); modified starches (e.g., ADPG pyrophosphorylases (AGPase), starch synthases (SS), starch branching enzymes (SBE) and starch debranching enzymes (SDBE)); and polymers or bioplastics (e.g., U.S. Pat. No. 5,602,321; beta-ketothiolase, polyhydroxybutyrate synthase, and acetoacetyl-CoA reductase (Schubert, et al., (1988) *J. Bacteriol.* 170:5837-5847) facilitate expression of polyhydroxyalkanoates (PHAs)), the disclosures of which are herein incorporated by reference. One could also combine the polynucleotides of the present invention with polynucleotides providing agronomic traits such as male sterility (e.g., see U.S. Pat. No. 5,583,210), stalk strength, flowering time, or transformation technology traits such as cell cycle regulation or gene targeting (e.g. WO 99/61619; WO 00/17364; WO 99/25821), the disclosures of which are herein incorporated by reference.

These stacked combinations can be created by any method including but not limited to cross breeding plants by any conventional or TopCross methodology, or genetic transformation. If the traits are stacked by genetically transforming the plants, the polynucleotide sequences of interest can be combined at any time and in any order. For example, a transgenic plant comprising one or more desired traits can be used as the target to introduce further traits by subsequent transformation. The traits can be introduced simultaneously in a co-transformation protocol with the polynucleotides of interest provided by any combination of transformation cassettes. For example, if two sequences will be introduced, the two sequences can be contained in separate transformation cassettes (trans) or contained on the same transformation cassette (cis). Expression of the sequences can be driven by the same promoter or by different promoters. In certain cases, it may be desirable to introduce a transformation cassette that will suppress the expression of the polynucleotide of interest. This may be combine with any combination of other suppression cassettes or overexpression cassettes to generate the desired combination of traits in the plant.

It may also be desirable to reduce or eliminate expression of genes encoding the instant polypeptides in plants for some applications. In order to accomplish this, a chimeric gene designed for co-suppression of the instant polypeptide can be constructed by linking a gene or gene fragment encoding that polypeptide to plant promoter sequences. Alternatively, a chimeric gene designed to express antisense RNA for all or part of the instant nucleic acid fragment can be constructed by linking the gene or gene fragment in reverse orientation to plant promoter sequences. Either the co-suppression or antisense chimeric genes could be introduced into plants via transformation wherein expression of the corresponding endogenous genes are reduced or eliminated.

Molecular genetic solutions to the generation of plants with altered gene expression have a decided advantage over more traditional plant breeding approaches. Changes in plant phenotypes can be produced by specifically inhibiting expression of one or more genes by antisense inhibition or cosuppression (U.S. Pat. Nos. 5,190,931, 5,107,065 and 5,283,323). An antisense or cosuppression construct would act as a dominant negative regulator of gene activity. While conventional mutations can yield negative regulation of gene activity these effects are most likely recessive. The dominant negative regulation available with a transgenic approach may be advantageous from a breeding perspective. In addition, the ability to restrict the expression of a specific phenotype to the reproductive tissues of the plant by the use of tissue specific promoters may confer agronomic advantages relative to conventional mutations which may have an effect in all tissues in which a mutant gene is ordinarily expressed.

The person skilled in the art will know that special considerations are associated with the use of antisense or cosuppression technologies in order to reduce expression of particular genes. For example, the proper level of expression of sense or antisense genes may require the use of different chimeric genes utilizing different regulatory elements known to the skilled artisan. Once transgenic plants are obtained by one of the methods described above, it will be necessary to screen individual transgenics for those that most effectively display the desired phenotype. Accordingly, the skilled artisan will develop methods for screening large numbers of transformants. The nature of these screens will generally be chosen on practical grounds. For example, one can screen by looking for changes in gene expression by using antibodies specific for the protein encoded by the gene being suppressed, or one could establish assays that specifically measure enzyme activity. A preferred method will be one which allows large numbers of samples to be processed rapidly, since it will be expected that a large number of transformants will be negative for the desired phenotype.

In another embodiment, the present invention relates to an isolated polypeptide comprising: (a) a first amino acid sequence comprising at least 50 or 100 amino acids, wherein the first amino acid sequence and the amino acid sequence of SEQ ID NO: 6, SEQ ID NO: 10, SEQ ID NO: 12, SEQ ID NO: 14, SEQ ID NO: 26, SEQ ID NO: 28, SEQ ID NO: 30, SEQ ID NO: 34 or SEQ ID NO: 42 have at least 80%, 85%, 90% or 95% identity based on the Clustal alignment method; (b) a second amino acid sequence comprising at least 50 or 100 amino acids, wherein the second amino acid sequence and the amino acid sequence of SEQ ID NO: 2 have at least 85%, 90% or 95% identity based on the Clustal alignment method; (c) a third amino acid sequence comprising at least 100 amino acids, wherein the third amino acid sequence and the amino acid sequence of SEQ ID NO: 4, SEQ ID NO: 16 or SEQ ID NO: 40 have at least 80%, 85%, 90% or 95% identity based on the Clustal alignment method; (d) a fourth amino acid sequence comprising at least 100 amino acids, wherein the fourth amino acid sequence and the amino acid sequence of SEQ ID NO: 24 have at least 85%, 90% or 95% identity based on the Clustal alignment method; (e) a fifth amino acid sequence comprising at least 150 amino acids, wherein the fifth amino acid sequence and the amino acid sequence of SEQ ID NO: 8 or SEQ ID NO: 44 have at least 80%, 85%, 90% or 95% identity based on the Clustal alignment method; (f) a sixth amino acid sequence comprising at least 150 amino acids, wherein the sixth amino acid sequence and the amino acid sequence of SEQ ID NO: 38 have at least 85%, 90% or 95% identity based on the Clustal alignment method; (g) a seventh amino acid sequence comprising at least 150 amino acids, wherein the seventh amino acid sequence and the amino acid sequence of SEQ ID NO: 50 have at least 90% or 95% identity based on the Clustal alignment method; (h) an eighth amino acid sequence comprising at least 160 amino acids, wherein the eighth amino acid sequence and the amino acid sequence of SEQ ID NO: 22 or SEQ ID NO: 32 have at least 85%, 90% or 95% identity based on the Clustal alignment method; (i) a ninth amino acid sequence comprising at least 170 amino acids, wherein the ninth amino acid sequence and the amino acid sequence of SEQ ID NO: 20 have at least 95% identity based on the Clustal alignment method; (j) a tenth amino acid sequence comprising at least 175 amino acids, wherein the tenth amino acid sequence and the amino acid sequence of SEQ ID NO: 18 have at least 80%, 85%, 90% or 95% identity based on the Clustal alignment method; or (k) an eleventh amino acid sequence comprising at least 200 amino acids, wherein the eleventh amino acid sequence and the amino acid sequence of SEQ ID NO: 46 or SEQ ID NO: 48 have at least 95% identity based on the Clustal alignment method. The first amino acid sequence preferably comprises the amino acid sequence of SEQ ID NO: 6, SEQ ID NO: 10, SEQ ID NO: 12, SEQ ID NO: 14, SEQ ID NO: 26, SEQ ID NO: 28, SEQ ID NO: 30, SEQ ID NO: 34 or SEQ ID NO: 42, the second amino acid sequence preferably comprises the amino acid sequence of SEQ ID NO: 2, the third amino acid sequence preferably comprises the amino acid sequence of SEQ ID NO: 4, SEQ ID NO: 16 or SEQ ID NO: 40, the fourth amino acid sequence preferably comprises the amino acid sequence of SEQ ID NO:24, the fifth amino acid sequence preferably comprises the amino acid sequence of SEQ ID NO: 8 or SEQ ID NO: 44, the sixth amino acid sequence preferably comprises the amino acid sequence of SEQ ID NO: 38, the seventh amino acid sequence preferably comprises the amino acid sequence of SEQ ID NO: 50, the eighth amino acid sequence preferably comprises the amino acid sequence of SEQ ID NO: 22 or SEQ ID NO: 32, the ninth amino acid sequence preferably comprises the amino acid sequence of SEQ ID NO: 20, the tenth amino acid sequence preferably comprises the amino acid sequence of SEQ ID NO: 18, and the eleventh amino acid sequence preferably comprises the amino acid sequence of SEQ ID NO: 46 or SEQ ID NO: 48. The polypeptide preferably is a FT or Ap3 homolog.

The instant polypeptides (or portions thereof) may be produced in heterologous host cells, particularly in the cells of microbial hosts, and can be used to prepare antibodies to these proteins by methods well known to those skilled in the art. The antibodies are useful for detecting the polypeptides of the instant invention in situ in cells or in vitro in cell extracts. Preferred heterologous host cells for production of the instant polypeptides are microbial hosts. Microbial expression systems and expression vectors containing regulatory sequences that direct high level expression of foreign proteins are well known to those skilled in the art. Any of these could be used to construct a chimeric gene for production of the instant polypeptides. This chimeric gene could then be introduced into appropriate microorganisms via transformation to provide high level expression of the encoded floral development protein. An example of a vector for high level expression of the instant polypeptides in a bacterial host is provided (Example 7).

All or a substantial portion of the polynucleotides of the instant invention may also be used as probes for genetically and physically mapping the genes that they are a part of, and used as markers for traits linked to those genes. Such information may be useful in plant breeding in order to develop lines with desired phenotypes. For example, the instant nucleic acid fragments may be used as restriction fragment length polymorphism (RFLP) markers. Southern blots (Maniatis) of restriction-digested plant genomic DNA may be probed with the nucleic acid fragments of the instant invention. The resulting banding patterns may then be subjected to genetic analyses using computer programs such as MapMaker (Lander, et al., (1987) *Genomics* 1:174-181) in order to construct a genetic map. In addition, the nucleic acid fragments of the instant invention may be used to probe Southern blots containing restriction endonuclease-treated genomic DNAs of a set of individuals representing parent and progeny of a defined genetic cross. Segregation of the DNA polymorphisms is noted and used to calculate the position of the instant nucleic acid sequence in the genetic map previously obtained using this population (Botstein, et al., (1980) *Am. J. Hum. Genet.* 32:314-331).

The production and use of plant gene-derived probes for use in genetic mapping is described in Bernatzky and Tanksley (1986) *Plant Mol. Biol. Reporter* 4:37-41. Numerous publications describe genetic mapping of specific cDNA clones using the methodology outlined above or variations thereof. For example, F2 intercross populations, backcross populations, randomly mated populations, near isogenic lines, and other sets of individuals may be used for mapping. Such methodologies are well known to those skilled in the art.

Nucleic acid probes derived from the instant nucleic acid sequences may also be used for physical mapping (i.e., placement of sequences on physical maps; see, Hoheisel, et al., *In: Nonmammalian Genomic Analysis: A Practical Guide*, Academic Press (1996) pp. 319-346, and references cited therein).

Nucleic acid probes derived from the instant nucleic acid sequences may be used in direct fluorescence in situ hybridization (FISH) mapping (Trask (1991) *Trends Genet.* 7:149-154). Although current methods of FISH mapping favor use of large clones (several to several hundred KB; see, Laan, et al., (1995) *Genome Res.* 5:13-20), improvements in sensitivity may allow performance of FISH mapping using shorter probes.

A variety of nucleic acid amplification-based methods of genetic and physical mapping may be carried out using the instant nucleic acid sequences. Examples include allele-specific amplification (Kazazian (1989) *J. Lab. Clin. Med.* 11:95-96), polymorphism of PCR-amplified fragments (CAPS; Sheffield, et al., (1993) *Genomics* 16:325-332), allele-specific ligation (Landegren, et al., (1988) *Science* 241:1077-1080), nucleotide extension reactions (Sokolov (1990) *Nucleic Acid Res.* 18:3671), Radiation Hybrid Mapping (Walter, et al., (1997) *Nat. Genet.* 7:22-28) and Happy Mapping (Dear and Cook (1989) *Nucleic Acid Res.* 17:6795-6807). For these methods, the sequence of a nucleic acid fragment is used to design and produce primer pairs for use in the amplification reaction or in primer extension reactions. The design of such primers is well known to those skilled in the art. In methods employing PCR-based genetic mapping, it may be necessary to identify DNA sequence differences between the parents of the mapping cross in the region corresponding to the instant nucleic acid sequence. This, however, is generally not necessary for mapping methods.

Loss of function mutant phenotypes may be identified for the instant cDNA clones either by targeted gene disruption protocols or by identifying specific mutants for these genes contained in a maize population carrying mutations in all possible genes (Ballinger and Benzer (1989) *Proc. Natl. Acad. Sci USA* 86:9402-9406; Koes, et al., (1995) *Proc. Natl. Acad. Sci USA* 92:8149-8153; Bensen, et al., (1995) *Plant Cell* 7:75-84). The latter approach may be accomplished in two ways. First, short segments of the instant nucleic acid fragments may be used in polymerase chain reaction protocols in conjunction with a mutation tag sequence primer on DNAs prepared from a population of plants in which Mutator transposons or some other mutation-causing DNA element has been introduced (see, Bensen, supra). The amplification of a specific DNA fragment with these primers indicates the insertion of the mutation tag element in or near the plant gene encoding the instant polypeptides. Alternatively, the instant nucleic acid fragment may be used as a hybridization probe against PCR amplification products generated from the mutation population using the mutation tag sequence primer in conjunction with an arbitrary genomic site primer, such as that for a restriction enzyme site-anchored synthetic adaptor. With either method, a plant containing a mutation in the endogenous gene encoding the instant polypeptides can be identified and obtained. This mutant plant can then be used to determine or confirm the natural function of the instant polypeptides disclosed herein.

EXAMPLES

The present invention is further defined in the following Examples, in which parts and percentages are by weight and degrees are Celsius, unless otherwise stated. It should be understood that these Examples, while indicating preferred embodiments of the invention, are given by way of illustration only. From the above discussion and these Examples, one skilled in the art can ascertain the essential characteristics of this invention, and without departing from the spirit and scope thereof, can make various changes and modifications of the invention to adapt it to various usages and conditions. Thus, various modifications of the invention in addition to those shown and described herein will be apparent to those skilled in the art from the foregoing description. Such modifications are also intended to fall within the scope of the appended claims.

The disclosure of each reference set forth herein is incorporated herein by reference in its entirety.

Example 1

Composition of cDNA Libraries

Isolation and Sequencing of cDNA Clones cDNA libraries representing mRNAs from various Peruvian lily (*Alstroemeria caryophylla*), balsam pear (*Momordica charantia*), garden balsam (*Impatiens balsamia*), corn (*Zea mays*), rice (*Oryza sativa*), soybean (*Glycine max*), and wheat (*Triticum aestivum*) tissues were prepared. The characteristics of the libraries are described below. Corn developmental stages are explained in the publication "How a corn plant develops" from the Iowa State University Coop. Ext. Service Special Report No. 48 reprinted June 1993.

TABLE 2 cDNA Libraries from Peruvian Lily, Balsam Pear, Garden Balsam, Corn, Rice, Soybean, and Wheat

| Library | Tissue | Clone |
|---|---|---|
| cbn10 | Corn Developing Kernel (Embryo and Endosperm); 10 Days After Pollination | cbn10.pk0052.f5 |
| cbn2 | Corn Developing Kernel Two Days After Pollination | cbn2.pk0035.f12 |
| cc71se-b | Corn Callus Type II Tissue, Somatic Embryo Formed | cc71se-b.pk0003.h10 |
| cco1n | Corn Cob of 67 Day Old Plants Grown in Green House* | cco1n.pk0010.h3<br>cco1n.pk0037.d10 |
| cen3n | Corn Endosperm 20 Days After Pollination* | cen3n.pk0004.e9<br>cen3n.pk0047.h7<br>cen3n.pk0093.f1<br>cen3n.pk0165.f1 |
| cta1n | Corn Tassel* | cta1n.pk0050.f8<br>cta1n.pk0058.d11b |
| ctn1c | Corn Tassel, Night Harvested | ctn1c.pk002.j23 |
| eal1c | Peruvian Lily Mature Leaf from Mature Stem | eal1c.pk006.e6 |
| fds | Balsam Pear Developing Seed | fds.pk0003.h2<br>fds.pk0026.d10 |
| fds1n | Balsam Pear Developing Seed | fds1n.pk001.p18 |
| ids | Garden Balsam Developing Seed | ids.pk0031.a5 |
| p0014 | Corn Leaf | p0014.ctush42r |
| p0081 | Corn Pedicel 10 Days After Pollination | p0081.chcad07r |
| p0095 | Ear Leaf Sheath*; Growth Conditions: Field; Control or Untreated Tissues; Growth Stage: 2-3 weeks After Pollen Shed | p0095.cwsas14f |
| p0104 | Corn V5-Stage Root Infested With Corn Root Worm* | p0104.cabak14rb |
| p0118 | Corn Stem Tissue Pooled From the 4-5 Internodes Subtending The Tassel At Stages V8-V12, Night Harvested* | p0118.chsaq04rb |
| p0119 | Corn V12-Stage Ear Shoot With Husk, Night Harvested* | p0119.cmtmg45rb |
| p0120 | Pooled Endosperm: 18, 21, 24, 27 and 29 Days After Pollination* | p0120.cdeae63r |
| p0128 | Corn Primary and Secondary Immature Ear | p0128.cpicl42r |
| rbm1c | Rice Bran 0 Hrs After Milling | rbm1c.pk001.a6 |
| rl0n | Rice 15 Day Old Leaf* | rl0n.pk0022.h10<br>rl0n.pk0022.h11 |
| rlr48 | Resistant Rice Leaf 15 Days After Germination, 48 Hours After Infection of Strain *Magnaporthe grisea* 4360-R-62 (AVR2-YAMO) | rlr48.pk0001.b1 |
| rls24 | Susceptible Rice Leaf 15 Days After Germination, 24 Hours After Infection of Strain *Magnaporthe grisea* 4360-R-67 (AVR2-YAMO) | rls24.pk0017.c7 |

TABLE 2-continued cDNA Libraries from Peruvian Lily, Balsam Pear, Garden Balsam, Corn, Rice, Soybean, and Wheat

| Library | Tissue | Clone |
|---|---|---|
| rr1 | Rice Root of Two Week Old Developing Seedling | rr1.pk0043.f9 |
| rsr9n | Rice Leaf 15 Days After Germination, Harvested 2-72 Hours Following Infection With *Magnaporthe grisea* (4360-R-62 and 4360-R-67)* | rsr9n.pk001.d1 |
| se3 | Soybean Embryo, 17 Days After Flowering | se3.pk0036.g4 |
| se6 | Soybean Embryo, 26 Days After Flowering | se6.pk0039.h6 |
| sfl1n | Soybean Immature Flower* | sfl1n.pk001.l16 |
| srr2c | Soybean 8-Day-Old Root | srr2c.pk002.o7 |
| ssl | Soybean Seedling 5-10 Days After Germination | ssl.pk0007.a9 |
| wdk2c | Wheat Developing Kernel, 7 Days After Anthesis | wdk2c.pk012.o17<br>wdk2c.pk017.p21<br>wdk2c.pk008.n3 |
| wdk9n1 | Wheat Kernels 3, 7, 14 and 21 Days After Anthesis* | wdk9n1.pk001.o20 |

*These libraries were normalized essentially as described in U.S. Pat. No. 5,482,845, incorporated herein by reference.

cDNA libraries may be prepared by any one of many methods available. For example, the cDNAs may be introduced into plasmid vectors by first preparing the cDNA libraries in Uni-ZAP™ XR vectors according to the manufacturer's protocol (Stratagene Cloning Systems, La Jolla, Calif.). The Uni-ZAP™ XR libraries are converted into plasmid libraries according to the protocol provided by Stratagene. Upon conversion, cDNA inserts will be contained in the plasmid vector pBluescript. In addition, the cDNAs may be introduced directly into precut Bluescript II SK(+) vectors (Stratagene) using T4 DNA ligase (New England Biolabs), followed by transfection into DH10B cells according to the manufacturer's protocol (GIBCO BRL Products). Once the cDNA inserts are in plasmid vectors, plasmid DNAs are prepared from randomly picked bacterial colonies containing recombinant pBluescript plasmids, or the insert cDNA sequences are amplified via polymerase chain reaction using primers specific for vector sequences flanking the inserted cDNA sequences. Amplified insert DNAs or plasmid DNAs are sequenced in dye-primer sequencing reactions to generate partial cDNA sequences (expressed sequence tags or "ESTs"; see, Adams, et al., (1991) *Science* 252:1651-1656). The resulting ESTs are analyzed using a Perkin Elmer Model 377 fluorescent sequencer.

Full-insert sequence (FIS) data is generated utilizing a modified transposition protocol. Clones identified for FIS are recovered from archived glycerol stocks as single colonies, and plasmid DNAs are isolated via alkaline lysis. Isolated DNA templates are reacted with vector primed M13 forward and reverse oligonucleotides in a PCR-based sequencing reaction and loaded onto automated sequencers. Confirmation of clone identification is performed by sequence alignment to the original EST sequence from which the FIS request is made.

Confirmed templates are transposed via the Primer Island transposition kit (PE Applied Biosystems, Foster City, Calif.) which is based upon the *Saccharomyces cerevisiae* Ty1 transposable element (Devine and Boeke (1994) *Nucleic Acids Res.* 22:3765-3772). The in vitro transposition system places unique binding sites randomly throughout a population of large DNA molecules. The transposed DNA is then used to transform DH10B electro-competent cells (Gibco BRL/Life Technologies, Rockville, Md.) via electroporation. The transposable element contains an additional selectable marker (named DHFR; Fling and Richards (1983) *Nucleic Acids Res.* 11:5147-5158), allowing for dual selection on agar plates of only those subclones containing the integrated transposon. Multiple subclones are randomly selected from each transposition reaction, plasmid DNAs are prepared via alkaline lysis, and templates are sequenced (ABI Prism dye-terminator ReadyReaction mix) outward from the transposition event site, utilizing unique primers specific to the binding sites within the transposon.

Sequence data is collected (ABI Prism Collections) and assembled using Phred/Phrap (P. Green, University of Washington, Seattle). Phred/Phrap is a public domain software program which re-reads the ABI sequence data, re-calls the bases, assigns quality values, and writes the base calls and quality values into editable output files. The Phrap sequence assembly program uses these quality values to increase the accuracy of the assembled sequence contigs. Assemblies are viewed by the Consed sequence editor (D. Gordon, University of Washington, Seattle).

In some of the clones the cDNA fragment corresponds to a portion of the 3'-terminus of the gene and does not cover the entire open reading frame. In order to obtain the upstream information one of two different protocols are used. The first of these methods results in the production of a fragment of DNA containing a portion of the desired gene sequence while the second method results in the production of a fragment containing the entire open reading frame. Both of these methods use two rounds of PCR amplification to obtain fragments from one or more libraries. The libraries some times are chosen based on previous knowledge that the specific gene should be found in a certain tissue and some times are randomly-chosen. Reactions to obtain the same gene may be performed on several libraries in parallel or on a pool of libraries. Library pools are normally prepared using from 3 to 5 different libraries and normalized to a uniform dilution. In the first round of amplification both methods use a vector-specific (forward) primer corresponding to a portion of the vector located at the 5'-terminus of the clone coupled with a gene-specific (reverse) primer. The first method uses a sequence that is complementary to a portion of the already known gene sequence while the second method uses a gene-specific primer complementary to a portion of the 3'-untranslated region (also referred to as UTR). In the second round of amplification a nested set of primers is used for both methods. The resulting DNA fragment is ligated into a pBluescript vector using a commercial kit and following the manufacturer's protocol. This kit is selected from many available from several vendors including Invitrogen (Carlsbad, Calif.), Promega Biotech (Madison, Wis.), and Gibco-BRL (Gaithersburg, Md.). The plasmid DNA is isolated by alkaline lysis method and submitted for sequencing and assembly using Phred/Phrap, as above.

Example 2

Identification of cDNA Clones cDNA clones encoding floral development proteins were identified by conducting BLAST (Basic Local Alignment Search Tool; Altschul, et al., (1993) *J. Mol. Biol.* 215:403-410; see also, the explanation of the BLAST algorithm on the world wide web site for the National Center for Biotechnology Information at the National Library of Medicine of the National Institutes of Health) searches for similarity to sequences contained in the BLAST "nr" database (comprising all non-redundant GenBank CDS translations, sequences derived from the 3-dimensional structure Brookhaven Protein Data Bank, the last major release of the SWISS-PROT protein sequence database, EMBL, and DDBJ databases). The cDNA sequences obtained in Example 1 were analyzed for similarity to all publicly available DNA sequences contained in the "nr" database using the BLASTN algorithm provided by the National Center for Biotechnology Information (NCBI). The DNA sequences were translated in all reading frames and compared for similarity to all publicly available protein sequences contained in the "nr" database using the BLASTX algorithm (Gish and States (1993) *Nat. Genet.* 3:266-272) provided by the NCBI. For convenience, the P-value (probability) of observing a match of a cDNA sequence to a sequence contained in the searched databases merely by chance as calculated by BLAST are reported herein as "pLog" values, which represent the negative of the logarithm of the reported P-value. Accordingly, the greater the pLog value, the greater the likelihood that the cDNA sequence and the BLAST "hit" represent homologous proteins.

ESTs submitted for analysis are compared to the genbank database as described above. ESTs that contain sequences more 5- or 3-prime can be found by using the BLASTn algorithm (Altschul, et al., (1997) *Nucleic Acids Res.* 25:3389-3402.) against the DuPont proprietary database comparing nucleotide sequences that share common or overlapping regions of sequence homology. Where common or overlapping sequences exist between two or more nucleic acid fragments, the sequences can be assembled into a single contiguous nucleotide sequence, thus extending the original fragment in either the 5 or 3 prime direction. Once the most 5-prime EST is identified, its complete sequence can be determined by Full Insert Sequencing as described in Example 1. Homologous genes belonging to different species can be found by comparing the amino acid sequence of a known gene (from either a proprietary source or a public database) against an EST database using the tBLASTn algorithm. The tBLASTn algorithm searches an amino acid query against a nucleotide database that is translated in all 6 reading frames. This search allows for differences in nucleotide codon usage between different species, and for codon degeneracy.

Example 3

Characterization of cDNA Clones Encoding Flowering Locus T (FT) Homologs

The BLASTX search using the EST sequences from clones listed in Table 3 revealed similarity of the polypeptides encoded by the cDNAs to FT and its homologs from *Citrus unshiu* (NCBI GenBank Identifier (GI) No. 4903139), *Arabidopsis thaliana* (NCBI GI Nos. 5002246 and 2190540), *Oryza sativa* (NCBI GI Nos. 5360178 and 5360180) and *Nicotiana tabacum* (NCBI GI No. 5453314). Shown in Table 3 are the BLAST results for individual ESTs ("EST"), the sequences of the entire cDNA inserts comprising the indicated cDNA clones ("FIS"), the sequences of contigs assembled from two or more ESTs ("Contig"), sequences of contigs assembled from an FIS and one or more ESTs ("Contig*"), or sequences encoding an entire protein derived from an FIS, a contig, or an FIS and PCR fragment sequence ("CGS"):

TABLE 3

BLAST Results for Sequences Encoding Polypeptides Homologous to Flowering Locus T (FT) Protein

| | | BLAST Results | |
|---|---|---|---|
| Clone | Status | NCBI GI No. | pLog Score |
| eal1c.pk006.e6 | EST | 4903139 | 65.70 |
| Contig of<br>fds.pk0003.h2<br>fds.pk0026.d10<br>fds1n.pk001.p18 | CGS | 5002246 | 75.00 |
| ids.pk0031.a5 (FIS) | CGS | 5002246 | 61.70 |
| Contig of<br>cbn10.pk0052.f5<br>cbn2.pk0035.f12<br>cco1n.pk0010.h3<br>p0095.cwsas14f<br>p0119.cmtmg45rb<br>p0128.cpicl42r | CGS | 4903139 | 77.00 |
| cc71se-b.pk0003.h10 (FIS) | CGS | 5002246 | 59.15 |
| cco1n.pk0037.d10 (FIS) | CGS | 2190540 | 68.52 |
| Contig of<br>cen3n.pk0004.e9<br>cen3n.pk0047.h7<br>cen3n.pk0093.f1<br>cen3n.pk0165.f1<br>p0120.cdeae63r | CGS | 5002246 | 57.30 |
| p0014.ctush42r (FIS) | CGS | 4903139 | 59.00 |
| p0081.chcad07r (FIS) | CGS | 4903139 | 81.00 |
| p0104.cabak14rb (FIS) | CGS | 5360178 | 93.70 |
| p0118.chsaq04rb (FIS) | CGS | 5360180 | 82.10 |
| rbm1c.pk001.a6 | EST | 5002246 | 46.04 |
| Contig of<br>rl0n.pk0022.h10<br>rl0n.pk0022.h11 | Contig | 4903139 | 43.30 |
| rlr48.pk0001.b1 | EST | 5002246 | 14.52 |
| rls24.pk0017.c7(FIS) | CGS | 5002246 | 64.70 |
| rr1.pk0043.f9(FIS) | CGS | 5360178 | 82.10 |
| rsr9n.pk001.d1 | EST | 2190540 | 35.70 |
| Contig of<br>se3.pk0036.g4<br>se6.pk0039.h6 (FIS) | CGS | 5002246 | 76.00 |
| srr2c.pk002.o7 (FIS) | CGS | 5360180 | 77.52 |
| Contig of<br>ssl.pk0007.a9<br>PCR fragment sequence | CGS | 5453314 | 73.70 |
| wdk2c.pk012.o17 (FIS) | CGS | 5002246 | 62.30 |
| wdk9n1.pk001.o20 (FIS) | CGS | 4903139 | 75.70 |
| cta1n.pk0058.d11b | FIS | 15218709 | 53.40 |
| rbm1c.pk001.a6:fis | CGS | 5002246 | 56.10 |
| rl0n.pk0022.h10:fis | FIS | 14517620 | 36.70 |
| rsr9n.pk001.d1:fis | CGS | 15218709 | 70.39 |

The PCR fragment that was used to extend the nucleotide sequence obtained from clone ssl.pk0007.a9 was obtained via methods (e.g., RACE techniques) well-known to those skilled in the art.

The amino acid sequence of the polypeptide encoded by the insert in clone wdk2c.pk012.o17 is identical to the amino acid sequence of the polypeptide encoded by the nucleotide sequence of a contig assembled from ESTs derived from clones wdk2c.pk008.n3, wdk2c.pk012.o17, and wdk2c.pk017.p21.

FIG. 1 presents an alignment of the amino acid sequences set forth in SEQ ID NOS: 4, 6, 8, 10, 12, 14, 16, 18, 20, 22, 30, 32, 36, 38, 40, 42 and 44 and the *Oryza sativa* sequence (NCBI GI No. 5360178; SEQ ID NO: 51).

The data in Table 4 represents a calculation of the percent identity of the amino sequences set forth in SEQ ID NOS: 4, 6, 8, 10, 12, 14, 16, 18, 20, 22, 30, 32, 36, 38, 40, 42 and 44 and the *Oryza sativa* sequence (NCBI GI No. 5360178; SEQ ID NO: 51).

TABLE 4

Percent Identity of Amino Acid Sequences Deduced From the Nucleotide Sequences of cDNA Clones Encoding Polypeptides Homologous to FT Protein

| SEQ ID NO. | Percent Identity to NCBI GI No. |
|---|---|
| 2 | 69.3 [gi 4903139] |
| 4 | 72.3 [gi 5002246] |
| 6 | 61.3 [gi 5002246] |
| 8 | 74.6 [gi 4903139] |
| 10 | 60.5 [gi 5002246] |
| 12 | 67.2 [gi 2190540] |
| 14 | 60.1 [gi 5002246] |
| 16 | 59.9 [gi 4903139] |
| 18 | 78.0 [gi 4903139] |
| 20 | 94.8 [gi 5360178] |
| 22 | 83.8 [gi 5360180] |
| 24 | 56.2 [gi 5002246] |
| 26 | 64.8 [gi 4903139] |
| 28 | 52.9 [gi 5002246] |
| 30 | 65.9 [gi 5002246] |
| 32 | 83.2 [gi 5360178] |
| 36 | 74.4 [gi 5002246] |
| 38 | 76.3 [gi 5360180] |
| 40 | 74.6 [gi 5453314] |
| 42 | 64.2 [gi 5002246] |
| 44 | 72.9 [gi 4903139] |
| 54 | 60.8 [gi 15218709] |
| 56 | 57.2 [gi 5002246] |
| 58 | 66.3 [gi 14517620] |
| 60 | 69.0 [gi 15218709] |

Sequence alignments and percent identity calculations were performed using the Megalign program of the LASERGENE bioinformatics computing suite (DNASTAR Inc., Madison, Wis.). Multiple alignment of the sequences was performed using the Clustal method of alignment (Higgins and Sharp (1989) *CABIOS*. 5:151-153) with the default parameters (GAP PENALTY=10, GAP LENGTH PENALTY=10). Default parameters for pairwise alignments using the Clustal method were KTUPLE 1, GAP PENALTY=3, WINDOW=5 and DIAGONALS SAVED=5. It will be recognized by one skilled in the art that conserved sequence elements within the encoded polypeptide are useful in identifying homologous enzymes. Two such elements, although not necessarily the only elements, are the sequences Asp-Pro-Asp-Xaa-Pro-Xaa-Pro-Ser-Xaa-Pro found, for example, at positions 70-79 of SEQ ID NO: 4, and Gly-Ile-His-Arg found, for example at positions 115-118 of SEQ ID NO: 4. Sequence alignments and BLAST scores and probabilities indicate that the nucleic acid fragments comprising the instant cDNA clones encode a substantial portion of a polypeptide encoded by a member of TFL1/FT gene family. These sequences represent the first Peruvian lily, balsam pear, garden balsam, corn, soybean, wheat sequences and new rice sequences encoding flowering locus T (FT or TFL) homologs known to Applicant.

Example 4

Characterization of cDNA Clones Encoding Ap3 Homologs

The BLASTX search using the EST sequences from clones listed in Table 5 revealed similarity of the polypeptides encoded by the cDNAs to MADS box proteins (Ap3 homologs) from *Oryza sativa* (NCBI GI Nos. 5295980 and 7446534) and *Medicago sativa* (NCBI GI No. 2827300). Shown in Table 5 are the BLAST results for individual ESTs ("EST"), the sequences of the entire cDNA inserts comprising the indicated cDNA clones ("FIS"), the sequences of contigs assembled from two or more ESTs ("Contig"), sequences of contigs assembled from an FIS and one or more ESTs ("Contig*"), or sequences encoding an entire protein derived from an FIS, a contig, or an FIS and PCR ("CGS"):

TABLE 5

BLAST Results for Sequences Encoding Polypeptides Homologous to Ap3 Protein

| | | BLAST Results | |
|---|---|---|---|
| Clone | Status | NCBI GI No. | pLog Score |
| cta1n.pk0050.f8 (FIS) | CGS | 5295980 | 113.00 |
| ctn1c.pk002.j23 (FIS) | CGS | 7446534 | 109.00 |
| sfl1n.pk001.l16 (FIS) | CGS | 2827300 | 114.00 |

FIG. 2 presents an alignment of the amino acid sequences set forth in SEQ ID NOS: 46, 48 and 50 and the *Oryza sativa* sequence (NCBI GI No. 5295980; SEQ ID NO: 52). The data in Table 6 represents a calculation of the percent identity of the amino acid sequences set forth in SEQ ID NOS: 46, 48 and 50 and the *Oryza sativa* sequence (NCBI GI No. 5295980; SEQ ID NO: 52).

TABLE 6

Percent Identity of Amino Acid Sequences Deduced From the Nucleotide Sequences of cDNA Clones Encoding Polypeptides Homologous to Ap3 Protein

| SEQ ID NO. | Percent Identity to [NCBI GI No.] |
|---|---|
| 46 | 86.6 [gi 5295980] |
| 48 | 91.4 [gi 7446534] |
| 50 | 85.9 [gi 2827300] |

Sequence alignments and percent identity calculations were performed using the Megalign program of the LASERGENE bioinformatics computing suite (DNASTAR Inc., Madison, Wis.). Multiple alignment of the sequences was performed using the Clustal method of alignment (Higgins and Sharp (1989) *CABIOS*. 5:151-153) with the default parameters (GAP PENALTY=10, GAP LENGTH PENALTY=10). Default parameters for pairwise alignments using the Clustal method were KTUPLE 1, GAP PENALTY=3, WINDOW=5 and DIAGONALS SAVED=5. It will be recognized by one skilled in the art that conserved sequence elements within the encoded polypeptide are useful in identifying homologous enzymes. One such element, although not necessarily the only element, is the sequence Arg-Gly-Lys-Ile-Xaa-Ile-Lys-Arg-Ile-Glu-Asn-Xaa-Thr-Asn-Arg-Gln-Val-Thr-Xaa-Ser-Lys-Arg-Arg-Xaa-Gly-Xaa-Xaa-Lys-Lys-Ala found, for example, at positions 3-32 of SEQ ID NO: 46. Sequence alignments and BLAST scores and probabilities indicate that the nucleic acid fragments comprising the instant cDNA clones encode a substantial portion of an Ap3 homolog. These sequences represent the first soybean sequence and new corn sequences encoding Ap3 homologs known to Applicant.

Example 5

Expression of Chimeric Genes in Monocot Cells

A chimeric gene comprising a cDNA encoding the instant polypeptides in sense orientation with respect to the maize 27 kD zein promoter that is located 5' to the cDNA fragment, and the 10 kD zein 3' end that is located 3' to the cDNA fragment, can be constructed. The cDNA fragment of this gene may be generated by polymerase chain reaction (PCR) of the cDNA clone using appropriate oligonucleotide primers. Cloning sites (NcoI or SmaI) can be incorporated into the oligonucleotides to provide proper orientation of the DNA fragment when inserted into the digested vector pML103 as described below. Amplification is then performed in a standard PCR. The amplified DNA is then digested with restriction enzymes NcoI and SmaI and fractionated on an agarose gel. The appropriate band can be isolated from the gel and combined with a 4.9 kb NcoI-SmaI fragment of the plasmid pML103. Plasmid pML103 has been deposited under the terms of the Budapest Treaty at ATCC (American Type Culture Collection, 10801 University Blvd., Manassas, Va. 20110-2209), and bears accession number ATCC 97366. The DNA segment from pML103 contains a 1.05 kb SalI-NcoI promoter fragment of the maize 27 kD zein gene and a 0.96 kb SmaI-SalI fragment from the 3' end of the maize 10 kD zein gene in the vector pGem9Zf(+) (Promega). Vector and insert DNA can be ligated at 15° C. overnight, essentially as described (Maniatis). The ligated DNA may then be used to transform *E. coli* XL1-Blue (Epicurian Coli XL-1 Blue™; Stratagene). Bacterial transformants can be screened by restriction enzyme digestion of plasmid DNA and limited nucleotide sequence analysis using the dideoxy chain termination method (Sequenase™ DNA Sequencing Kit; U.S. Biochemical). The resulting plasmid construct would comprise a chimeric gene encoding, in the 5' to 3' direction, the maize 27 kD zein promoter, a cDNA fragment encoding the instant polypeptides, and the 10 kD zein 3' region.

The chimeric gene described above can then be introduced into corn cells by the following procedure. Immature corn embryos can be dissected from developing caryopses derived from crosses of the inbred corn lines H99 and LH132. The embryos are isolated 10 to 11 days after pollination when they are 1.0 to 1.5 mm long. The embryos are then placed with the axis-side facing down and in contact with agarose-solidified N6 medium (Chu, et al., (1975) *Sci. Sin. Peking* 18:659-668). The embryos are kept in the dark at 27° C. Friable embryogenic callus consisting of undifferentiated masses of cells with somatic proembryoids and embryoids borne on suspensor structures proliferates from the scutellum of these immature embryos. The embryogenic callus isolated from the primary explant can be cultured on N6 medium and sub-cultured on this medium every 2 to 3 weeks.

The plasmid, p35S/Ac (obtained from Dr. Peter Eckes, Hoechst Ag, Frankfurt, Germany) may be used in transformation experiments in order to provide for a selectable marker. This plasmid contains the Pat gene (see, European Patent Publication 0 242 236) which encodes phosphinothricin acetyl transferase (PAT). The enzyme PAT confers resistance to herbicidal glutamine synthetase inhibitors such as phosphinothricin. The pat gene in p35S/Ac is under the control of the 35S promoter from Cauliflower Mosaic Virus (Odell, et al., (1985) *Nature* 313:810-812) and the 3' region of the nopaline synthase gene from the T-DNA of the Ti plasmid of *Agrobacterium tumefaciens*.

The particle bombardment method (Klein, et al., (1987) *Nature* 327:70-73) may be used to transfer genes to the callus culture cells. According to this method, gold particles (1 μm in diameter) are coated with DNA using the following technique. Ten μg of plasmid DNAs are added to 50 μL of a suspension of gold particles (60 mg per mL). Calcium chloride (50 μL of a 2.5 M solution) and spermidine free base (20 μL of a 1.0 M solution) are added to the particles. The suspension is vortexed during the addition of these solutions. After 10 minutes, the tubes are briefly centrifuged (5 sec at 15,000 rpm) and the supernatant removed. The particles are resuspended in 200 μL of absolute ethanol, centrifuged again and the supernatant removed. The ethanol rinse is performed again and the particles resuspended in a final volume of 30 μL of ethanol. An aliquot (5 μL) of the DNA-coated gold particles can be placed in the center of a Kapton™ flying disc (Bio-Rad Labs). The particles are then accelerated into the corn tissue with a Biolistic™ PDS-1000/He (Bio-Rad Instruments, Hercules, Calif.), using a helium pressure of 1000 psi, a gap distance of 0.5 cm and a flying distance of 1.0 cm.

For bombardment, the embryogenic tissue is placed on filter paper over agarose-solidified N6 medium. The tissue is arranged as a thin lawn and covered a circular area of about 5 cm in diameter. The petri dish containing the tissue can be placed in the chamber of the PDS-1000/He approximately 8 cm from the stopping screen. The air in the chamber is then evacuated to a vacuum of 28 inches of Hg. The macrocarrier is accelerated with a helium shock wave using a rupture membrane that bursts when the He pressure in the shock tube reaches 1000 psi.

Seven days after bombardment the tissue can be transferred to N6 medium that contains bialophos (5 mg per liter) and lacks casein or proline. The tissue continues to grow slowly on this medium. After an additional 2 weeks the tissue can be transferred to fresh N6 medium containing bialophos. After 6 weeks, areas of about 1 cm in diameter of actively growing callus can be identified on some of the plates containing the bialophos-supplemented medium. These calli may continue to grow when sub-cultured on the selective medium.

Plants can be regenerated from the transgenic callus by first transferring clusters of tissue to N6 medium supplemented with 0.2 mg per liter of 2,4-D. After two weeks the tissue can be transferred to regeneration medium (Fromm, et al., (1990) *Bio/Technology* 8:833-839).

Example 6

Expression of Chimeric Genes in Dicot Cells

A seed-specific expression cassette composed of the promoter and transcription terminator from the gene encoding the β subunit of the seed storage protein phaseolin from the bean *Phaseolus vulgaris* (Doyle, et al., (1986) *J. Biol. Chem.* 261:9228-9238) can be used for expression of the instant polypeptides in transformed soybean. The phaseolin cassette includes about 500 nucleotides upstream (5') from the translation initiation codon and about 1650 nucleotides downstream (3') from the translation stop codon of phaseolin. Between the 5' and 3' regions are the unique restriction endonuclease sites NcoI (which includes the ATG translation initiation codon), SmaI, KpnI and XbaI. The entire cassette is flanked by HindIII sites.

The cDNA fragment of this gene may be generated by polymerase chain reaction (PCR) of the cDNA clone using appropriate oligonucleotide primers. Cloning sites can be incorporated into the oligonucleotides to provide proper orientation of the DNA fragment when inserted into the expression vector. Amplification is then performed as described above, and the isolated fragment is inserted into a pUC18 vector carrying the seed expression cassette.

Soybean embryos may then be transformed with the expression vector comprising sequences encoding the instant polypeptides. To induce somatic embryos, cotyledons, 3-5 mm in length dissected from surface sterilized, immature seeds of the soybean cultivar A2872, can be cultured in the light or dark at 26° C. on an appropriate agar medium for 6-10 weeks. Somatic embryos which produce secondary embryos are then excised and placed into a suitable liquid medium. After repeated selection for clusters of somatic embryos which multiplied as early, globular staged embryos, the suspensions are maintained as described below.

Soybean embryogenic suspension cultures can be maintained in 35 mL liquid media on a rotary shaker, 150 rpm, at 26° C. with florescent lights on a 16:8 hour day/night schedule. Cultures are subcultured every two weeks by inoculating approximately 35 mg of tissue into 35 mL of liquid medium.

Soybean embryogenic suspension cultures may then be transformed by the method of particle gun bombardment (Klein, et al., (1987) *Nature* (London) 327:70-73, U.S. Pat. No. 4,945,050). A DuPont Biolistic™ PDS1000/HE instrument (helium retrofit) can be used for these transformations.

A selectable marker gene which can be used to facilitate soybean transformation is a chimeric gene composed of the 35S promoter from Cauliflower Mosaic Virus (Odell, et al., (1985) *Nature* 313:810-812), the hygromycin phosphotransferase gene from plasmid pJR225 (from *E. coli*; Gritz, et al., (1983) *Gene* 25:179-188) and the 3' region of the nopaline synthase gene from the T-DNA of the Ti plasmid of *Agrobacterium tumefaciens*. The seed expression cassette comprising the phaseolin 5' region, the fragment encoding the instant polypeptides and the phaseolin 3' region can be isolated as a restriction fragment. This fragment can then be inserted into a unique restriction site of the vector carrying the marker gene.

To 50 μL of a 60 mg/mL 1 μm gold particle suspension is added (in order): 5 μL DNA (1 μg/μL), 20 μL spermidine (0.1 M), and 50 μL $CaCl_2$ (2.5 M). The particle preparation is then agitated for three minutes, spun in a microfuge for 10 seconds and the supernatant removed. The DNA-coated particles are then washed once in 400 μL 70% ethanol and resuspended in 40 μL of anhydrous ethanol. The DNA/particle suspension can be sonicated three times for one second each. Five μL of the DNA-coated gold particles are then loaded on each macro carrier disk.

Approximately 300-400 mg of a two-week-old suspension culture is placed in an empty 60×15 mm petri dish and the residual liquid removed from the tissue with a pipette. For each transformation experiment, approximately 5-10 plates of tissue are normally bombarded. Membrane rupture pressure is set at 1100 psi and the chamber is evacuated to a vacuum of 28 inches mercury. The tissue is placed approximately 3.5 inches away from the retaining screen and bombarded three times. Following bombardment, the tissue can be divided in half and placed back into liquid and cultured as described above.

Five to seven days post bombardment, the liquid media may be exchanged with fresh media, and eleven to twelve days post bombardment with fresh media containing 50 mg/mL hygromycin. This selective media can be refreshed weekly. Seven to eight weeks post bombardment, green, transformed tissue may be observed growing from untransformed, necrotic embryogenic clusters. Isolated green tissue is removed and inoculated into individual flasks to generate new, clonally propagated, transformed embryogenic suspension cultures. Each new line may be treated as an independent transformation event. These suspensions can then be subcultured and maintained as clusters of immature embryos or regenerated into whole plants by maturation and germination of individual somatic embryos.

Example 7

Expression of Chimeric Genes in Microbial Cells

The cDNAs encoding the instant polypeptides can be inserted into the T7 *E. coli* expression vector pBT430. This vector is a derivative of pET-3a (Rosenberg, et al., (1987) *Gene* 56:125-135) which employs the bacteriophage T7 RNA polymerase/T7 promoter system. Plasmid pBT430 was constructed by first destroying the EcoRI and HindIII sites in pET-3a at their original positions. An oligonucleotide adaptor containing EcoRI and HindIII sites was inserted at the BamHI site of pET-3a. This created pET-3aM with additional unique cloning sites for insertion of genes into the expression vector. Then, the NdeI site at the position of translation initiation was converted to an NcoI site using oligonucleotide-directed mutagenesis. The DNA sequence of pET-3aM in this region, 5'-CATATGG, was converted to 5'-CCCATGG in pBT430.

Plasmid DNA containing a cDNA may be appropriately digested to release a nucleic acid fragment encoding the protein. This fragment may then be purified on a 1% low melting agarose gel. Buffer and agarose contain 10 μg/ml ethidium bromide for visualization of the DNA fragment. The fragment can then be purified from the agarose gel by digestion with GELase™ (Epicentre Technologies, Madison, Wis.) according to the manufacturer's instructions, ethanol precipitated, dried and resuspended in 20 μL of water. Appropriate oligonucleotide adapters may be ligated to the fragment using T4 DNA ligase (New England Biolabs (NEB), Beverly, Mass.). The fragment containing the ligated adapters can be purified from the excess adapters using low melting agarose as described above. The vector pBT430 is digested, dephosphorylated with alkaline phosphatase (NEB) and deproteinized with phenol/chloroform as described above. The prepared vector pBT430 and fragment can then be ligated at 16° C. for 15 hours followed by transformation into DH5 electrocompetent cells (GIBCO BRL). Transformants can be selected on agar plates containing LB media and 100 μg/mL ampicillin. Transformants containing the gene encoding the instant polypeptides are then screened for the correct orientation with respect to the T7 promoter by restriction enzyme analysis.

For high level expression, a plasmid clone with the cDNA insert in the correct orientation relative to the T7 promoter can be transformed into *E. coli* strain BL21 (DE3) (Studier, et al., (1986) *J. Mol. Biol.* 189:113-130). Cultures are grown in LB medium containing ampicillin (100 mg/L) at 25° C. At an optical density at 600 nm of approximately 1, IPTG (isopropylthio-β-galactoside, the inducer) can be added to a final concentration of 0.4 mM and incubation can be continued for 3 h at 25° C. Cells are then harvested by centrifugation and re-suspended in 50 μL of 50 mM Tris-HCl at pH 8.0 containing 0.1 mM DTT and 0.2 mM phenyl methylsulfonyl fluoride. A small amount of 1 mm glass beads can be added and the mixture sonicated 3 times for about 5 seconds each time with a microprobe sonicator. The mixture is centrifuged and the protein concentration of the supernatant determined. One µg of protein from the soluble fraction of the culture can be separated by SDS-polyacrylamide gel electrophoresis. Gels can be observed for protein bands migrating at the expected molecular weight.

Example 8

Phylogenetic Analysis of Corn Translational Homologs of the *Arabidopsis* Flowering Proteins FT (Flowering Locus T) and TFL (Terminal Flower)

The relationship of maize and *Arabidopsis* FT-TFL proteins was revealed by phylogenetic analysis. Seven maize FT-TFL putative proteins were included in the phylogenetic analysis as well: *Arabidopsis* FT (GenBank accession number AB027504) and TFL (GenBank accession number U77674), rice Hd3a, heading QTL3 (GenBank accession number AB052942), rice RCN1 (GenBank accession number AF159882), snapdragon CEN, centroradialis (GenBank accession number S81193), tomato SP, self-pruning (GenBank accession number U84140). The mice PEBP protein (GenBank accession number AF300422) was used as an outgroup to root the tree. The phylogenetic tree was constructed by the maximum parsimony methods (FIG. 3). The phylogram clearly delimits two major clades that corresponded to the FT and TFL proteins. Maize proteins ZmFT4 and ZmFT5 form an outgroup with the mice protein mPEBP, which suggests that their functions are not related to the flowering time.

The FT lade consists of five maize proteins with different degrees of amino acid identity. ZmFT1 is closely related to the *Arabidopsis* FT sharing 71% identity and 83% similarity. ZmFT3 is closely related to the rice Hd3a QTL for photoperiod sensitivity (GenBank accession number AB052942) sharing 88% identity and 94% similarity. ZmFT3 shows less than 60% identity to both proteins from rice and *Arabidopsis*.

The TFL lade consists of six members including the snapdragon CEN and tomato SP proteins. This lade shows higher conservation of amino acid sequences than the FT lade. The maize proteins ZmFTL1 and ZmFTL2 are tightly associated with the rice RCN1 (Nakagawa, et al., (2002)). ZmTFL1 is highly homologous to the rice RCN1 sharing 94% identity and 98% similarity. ZmFTL2 is also close to RCN1 sharing 85% identity and 91% similarity. The high level of the amino acid conservation between species indicates that TFL protein structures are under a strong evolution pressure for function. Thus ZmTFL proteins may play roles as repressors of flowering similar to the *Arabidopsis* TFL and rice RCN1.

Example 9

Genomic Sequences of Maize FT-TFL Homologs

To get genomic sequences of ZmFT and ZmTFL genes, BAC (bacterial artificial chromosome) libraries were screened with inserts of EST's SEQ ID NO: 7, 9, 15, 17, 19, 21 (Table 1). HindIII fragments of BAC DNAs were subcloned into a plasmid BluescriptIISK(+) and sequenced at the DuPont sequencing facilities. The genomic sequences of ZmFT1, ZmFT2, ZmFT3, ZmTFL1 and ZmTFL2 are listed in the sequence listing for this specification (Sequence ID NOS: 63, 64, 65, 66 and 67, respectively).

The genomic structures of the ZmFT and ZmTFL sequences are shown in FIG. 4, and are described in detail as follows:

The genomic region of ZmFT1 (SEQ ID NO: 63) is composed of a promoter (1-2211 nt), 5'UTR (2212-2385 nt), exon 1 (2386-3580 nt), exon 2 (2741-2802 nt), exon 3 (9718-9760 nt), exon 4 (9845-10067), 3'UTR (10067-10316).

The genomic region of ZmFT2 (SEQ ID NO: 64) is composed of 5'UTR (1-93), exon1 (94-293), exon2 (468-525), exon3 (765-806), exon 4 (1411-1651), 3'UTR (1652-1840).

The genomic region of ZmFT3 (SEQ ID NO: 65) is composed of a promoter (286-4375 nt), 5'UTR (4376-4542 nt), exon 1 (4543-4743 nt), exon 2 (4894-4953 nt), exon 3 (5688-5728 nt), exon 4 (6166-6396 nt), 3'UTR (6397-6860).

The genomic region of ZmTFL1 (SEQ ID NO: 66) is composed of two copies of ZmTFL1 gene arranged in a perfect tandem. The first copy has a partial promoter (1-562 nt), 5'UTR (486-563 nt), exon 1 (564-763 nt), exon 2 (846-9907 nt), exon 3 (1056-1096 nt), exon 4 (1176-1364 nt), 3'UTR (1395-1611 nt), 3' downstream segment (1612-2435 nt). The second copy begins from 2436 nt and shows the identical structure as the first one. The genomic organization of ZmTFL1 gene exhibits an unusual configuration of a tandem array of two gene copies. The unit length in tandem is 2292 nt, which include a 5'upstream sequence (364 nt), exon/intron genic segment (1116 nt) and 3'downstream sequence (812 nt). A promoter for the second ZmTFL1 copy may be defined between nucleotides 1611 and 2435 (824 nt total length). Almost identical nucleotide sequences of both units suggest a very recent duplication of ZmTFL1 gene in Mo17 genome.

The genomic region of ZmTFL2 (SEQ ID NO: 67) is composed of a promoter (1-1450 nt), 5'UTR (1451-1518 nt), exon 1 (1519-1780 nt), exon 2 (2097-2137 nt), exon 3 (2309-2595 nt), and 3'UTR (2596-2881 nt).

The overall genomic structures of ZmFT1, Zm FT2, ZmFT3 and ZmTFL1 are very similar, each comprising 4 exons and 3 introns. They are similar to the *Arabidopsis* FT (GenBank accession number NC003070) and TFL genes (GenBank accession number NC003076) and the rice gene Hd3a (GenBank accession number AB052942). The genomic structure of ZmTFL2 is different as it contains only 2 introns. The absence of intron 1 results in a fusion of exon1 and exon 2. The coding segments of exons are nearly identical ranging in sizes 195-204 nt (exon1), 61nt (exon2), 41nt (exon3) and 213-238 nt (exon 4). This is consistent with the very close sizes of encoded proteins of 173-177 amino acids. Conversely, intron lengths vary significantly between the ZmFT and ZmTFL genes. Intron1 ranges from 0 to 186 nt, intron 2 ranges from 147 to 6916 nt, and intron 3 ranges from 39 to 604 nt. The ZmFT1 gene possesses the most unusual intron, with its second intron being 6917 nt, which is 7 times longer than a coding sequence. Such a long intron size is very uncommon in plants and raises a possibility of the particular role of this intron in controlling the ZmFT1 gene expression.

Example 10

Map Position of ZmFT and ZmFTL Genes and Correlation with QTL's Loci for Flowering Time All ZmFT and ZmFTL genes have been mapped to chromosomes using the maize-oat addition lines (Kynast, et al., (2001)). Pairs of gene-specific primers (Table 2) were designed to amplify each gene from the 10 samples of the oat DNA each of which carrying a single maize chromosome. Genes were mapped to following chromosomes: ZmFT1-chromosome 8, ZmFT2-chromosome 3, ZmFT3-chromosome 6, ZmTFL1-chromosome 3, ZmTFL2-chromosome 6.

The ZmFT1 gene is mapped to chromosome 8 where two major QTLs for early flowering, vgt1 and vgt2 are located (Vladutu, et al., (1999)). To place ZmFT1 more precisely on chromosome 8, the mapping population SX19 SYN4 derived from B37 and Mo17 was used. PCR primers SEQ ID NO: 6 and SEQ ID NO: 7 (Table 2) were designed. These primers amplify an insertion/deletion polymorphism between B73 and Mo17 in the 5' untranslated region of ZmFT1. The 270 lines from the SX19 SYN4 population were genotyped for the ZmFT1 gene. Co-segregation analysis was performed using marker data and genetic maps assembled from both public and Pioneer sources. Linkage between ZmFT1 and each marker was tested by applying a 2×2 $X^2$ test for independent segregation (one degree of freedom); the threshold for declaring linkage was $X^2>18$. The genome-wide cumulative type I error probability was 0.05 assuming 1500 marker tests.

Significant linkage was detected between ZmFT1 and a group of markers located on chromosome 8; no linkage was detected elsewhere. The nearest marker to ZmFT1 was UMC32b (14 recombinant lines out of 239 lines genotyped). UMC32b is located at 199 cM on the public 2002 IBM map (568 cM total genetic distance for chromosome 8). ZmFT1 was also tightly linked to UMC120a (16/145 recombinants). UMC120a is located at 55 cM on the public 1998 UMC map (183 cM total After converting the observed two-point recombination fractions to single meioisis genetic distances, ZmFT1 lies from 1.1 cM UMC32b (direction not determined) and 2.2 cM below UMC120a.

Vgt1 and Vgt2 are linked QTLs for flowering time and leaf number defined by Vladutu, et al., (1999) on chromosome 8 between markers UMC236 and UMC89a. UMC236 is located at 54cM of UMC 1998 map. UMC89a is located at 327cM of 2002 IBM map. This places ZmFT1 between UMC236 and UMC89a. Therefore ZmFT1 is a candidate gene for either or both QTLs.

Example 11

Temporal and Spatial Expression of ZmFT-TFL Genes During Plant Development

ZmFT genes comprise a family of related genes with a significant homology to each other. To validate their roles in the transition from the vegetative growth to reproductive, their expressions have been assayed throughout corn plant development. The transition to flowering is a complex development event. Internal and external signals entail irreversible changes in a seedling growing point, the shoot apical meristem. During switching to flowering the shoot apical meristem (SAM) stops producing leaves and commits to form influences. In maize, the floral signals are generated in immature leaves (Colasanti, et al., (1998)). Thus two tissues play central roles in the transition to flowering, immature leaves and the shoot apical meristem. If candidate genes are expressed in those tissues, they are very likely to play a role in timing of flowering. The SAM shows morphological changes during the transition to flowering such as elongation and branch primordial. This moment was recorded as the transition point. Seedlings (B73 inbred line) have been grown in a green house under standard conditions. Every 3 days seedlings were examined for morphological changes in the SAM and 3-5 SAMs and several immature leaves were sampled. Samples at 8 time points were collected. Total RNAs were isolated from sampled tissues and RT-PCR has been performed for each of ZmFT-TFL genes. Pairs of gene-specific primers were designed according EST sequences to amplify specifically one cDNA at time (Table 2). Mature leaves, the embryo from 15 days after pollination, kernels and seedling roots were tested for expression of ZmFT genes as well. Out of 6 genes examined, ZmFT1, ZmTFL1 and ZmTFL2 showed expression in the shoot apical meristem in a very specific pattern for each gene. ZmFT2, ZmFT3 and ZmFT4 are expressed neither in the SAM nor in immature leaves, which excluded them from the floral transition genes. ZmFT2 is expressed in mature leaves that still may play some role in flowering. ZmFT3 is expressed only in pedicel, and ZmFT4 is expressed in the embryo. They may function in other pathways not related to the floral transition.

As shown by RT-PCR, ZmFT1 gene is not expressed in the SAM from seedlings during vegetative growth up 26 days after planting. The transition from vegetative to reproductive growth occurs in the SAM around 22-26 days after planting. An RT-PCR band from ZmFT1 mRNA appears in the SAM at 33 days after planting when the floral transition occurred. Thus ZmFT1 gene is expressed in the young inflorescence. ZmTFL1 and ZmTFL2 are expressed in the SAM during vegetative growth at 3-22 days after planting. They cease their expression before the floral transition around 26 days.

ZmFT1 demonstrates a pattern of expression consistent with function as an activator of the flowering. Its transcription is not detected in the SAM during a vegetative growth, but it is activated sharply in the SAM very early after the transition. Conversely, ZmTFL1 and ZmTFL2 are active in the SAM during the vegetative growth and their expressions decline just before the meristem transition to the reproductive growth. This pattern of expression is consistent with their functions as flowering repressors.

Example 12

Expression of ZmTF1 Gene in the Shoot Apical Meristem of the Flowering Mutant Id1 (Indeterminate 1)

The temporal and spatial patterns of ZmFT1 expression are consistent with its function as a floral activator in corn. Id1 (indeterminate) gene is the only maize cloned gene with a clear role in a floral transition (Colasanti, et al., (1998)). The Id1 gene encodes transcription factors and regulates the production of a transmissible signal in the immature leaves that induces the transition of the SAM to reproductive development. To test the possibility whether the ZmFT1 expression is related to the Id1 function, the SAM were sampled from wild type and id1 homozygous siblings after the floral transition. Wild type plants were sampled at 27, 33, 40 and 48 days after planting. Id mutants were sampled also at 66 and 70 days because of delayed flowering phenotypes. RT-PCR analysis has demonstrated that ZmFT1 is expressed in the inflorescence up to 48 days, but it did not expression in the inflorescence of the id1 seedling, even at the later stage of 70 days. Thus these data strongly suggest ZmFT1 is in the same pathway with the Id1 transcription factor. Activation of ZmFT1 transcription requires a floral signal produced in immature leaves under control of the Id1 gene. The absence of this signal in the Id1 homozygous mutant prevents ZmFT1 expression. Thus ZmFT1 is operating down stream from the Id1 gene in the same pathway. The expression patterns of ZmTFL1 and ZmTFL2 are not significantly affected in the Id1 mutant seedlings. Those genes may be placed in independent pathways.

Example 13

Inactivation of ZmFT1 and ZmTFL2 Genes by the Mutator Transposon Insertions

Gene inactivation can be used to confirm the function of ZmFT-TFL genes in flowering. Pioneer proprietary system TUSC (Trait Utility System for Corn) was used to screen ZmFT1, ZmTFL1, and ZmTFL2 genes disrupted by the Mutator transposable element insertion. $F_2$ families segregating for the Mutator insertions were screened by PCR with the Mu specific primer (SEQ ID NO: 24) and gene specific primers SEQ ID NO: 21, 22, 23 (Table 2). Positive signals were found for the Mutator insertions in ZmFT1 and ZmTFL2, not in ZmTFL1. The Mu insertion sites were sequenced from PCR products. TUSC plants were grown and crossed to different inbred lines to segregate away non-related mutations created by Mu-activity. Flowering phenotypic analysis known to those of skill in the art will demonstrate which genes exhibit and/or modify flowering function.

All publications and patent applications mentioned in the specification are indicative of the level of those skilled in the art to which this invention pertains. All publications and patent applications are herein incorporated by reference to the same extent as if each individual publication or patent application was specifically and individually indicated to be incorporated by reference.

This invention may be embodied in many different forms and should not be construed as limited to the embodiments set forth herein; rather, these embodiments are provided so that this disclosure will be thorough and complete, and will fully convey the scope of the invention to those skilled in the art. Like numbers refer to like elements throughout.

Many modifications and other embodiments of the invention will come to mind to one skilled in the art to which this invention pertains having the benefit of the teachings presented in the foregoing descriptions and the associated drawings. Therefore, it is to be understood that the invention is not to be limited to the specific embodiments disclosed and that modifications and other embodiments are intended to be included within the scope of the appended claims. Although specific terms are employed herein, they are used in a generic and descriptive sense only and not for purposes of limitation.

What is claimed is:

1. An isolated polynucleotide comprising:

(a) a nucleotide sequence encoding a polypeptide of SEQ ID NO: 20, having floral development activity, or (b) the complement of the nucleotide sequence, wherein the complement and the nucleotide sequence contain the same number of nucleotides and are 100% complementary.

2. The polynucleotide of claim 1, wherein the amino acid sequence of the polypeptide comprises the amino acid sequence of SEQ ID NO: 20.

3. The polynucleotide of claim 1 wherein the nucleotide sequence comprises the nucleotide sequence of SEQ ID NO: 19.

4. A vector comprising the polynucleotide of claim 1.

5. A recombinant DNA construct comprising the polynucleotide of claim 1 operably linked to a regulatory sequence.

6. A method for transforming a cell, comprising transforming a cell with the polynucleotide of claim 1.

7. An isolated cell comprising the recombinant DNA construct of claim 5.

8. A method for producing a plant comprising transforming a plant cell with the polynucleotide of claim 1 and regenerating a plant from the transformed plant cell.

9. A plant comprising the recombinant DNA construct of claim 5.

10. A seed comprising the recombinant DNA construct of claim 5.

* * * * *

SEQUENCE LISTING

```
<160> NUMBER OF SEQ ID NOS: 68

<210> SEQ ID NO 1
<211> LENGTH: 492
<212> TYPE: DNA
<213> ORGANISM: Alstroemeria caryophylla

<400> SEQUENCE: 1

attgatttct agctagctcc tttgcttgca atagatatat aatgagcgga gaaagcgaaa      60

ccctggtgat tggtagggtg gtgggggacg tgttggaccc ctacactaaa accacggcgc     120

tcaggatcag gtatggatcg aaagaggtga cgtgcgggca cgagctaaag ccatcgcagg     180

tcgtcataca gccaagggtg gaggttggag ggaaggatct caggaccttt tacacacttg     240

tgatggtaga ccctgatgct ccgagcccaa gcaacccaca ccttagggcg tatctacatt     300

ggctggtgac tgacctcccg ggaactactg gagctagctt cgggcaagag gtgatgaggt     360

acgagagccc aaggccaaca ttagggattc accgcttcgt cttcgtgctg ttccggcagc     420

tcgggcggca gacggtgcag gtgcccaccc ccgggaggcg ccagaacttc aacacaaggg     480

gctttgcaag ag                                                         492


<210> SEQ ID NO 2
<211> LENGTH: 150
<212> TYPE: PRT
<213> ORGANISM: Astroemeria caryophylla

<400> SEQUENCE: 2

Met Ser Gly Glu Ser Glu Thr Leu Val Ile Gly Arg Val Val Gly Asp
 1               5                  10                  15

Val Leu Asp Pro Tyr Thr Lys Thr Thr Ala Leu Arg Ile Arg Tyr Gly
            20                  25                  30

Ser Lys Glu Val Thr Cys Gly His Glu Leu Lys Pro Ser Gln Val Val
        35                  40                  45

Ile Gln Pro Arg Val Glu Val Gly Gly Lys Asp Leu Arg Thr Phe Tyr
```

-continued

```
    50                  55                  60

Thr Leu Val Met Val Asp Pro Asp Ala Pro Ser Pro Ser Asn Pro His
65                  70                  75                  80

Leu Arg Ala Tyr Leu His Trp Leu Val Thr Asp Leu Pro Gly Thr Thr
                85                  90                  95

Gly Ala Ser Phe Gly Gln Glu Val Met Arg Tyr Glu Ser Pro Arg Pro
            100                 105                 110

Thr Leu Gly Ile His Arg Phe Val Phe Val Leu Phe Arg Gln Leu Gly
        115                 120                 125

Arg Gln Thr Val Gln Val Pro Thr Pro Gly Arg Arg Gln Asn Phe Asn
    130                 135                 140

Thr Arg Gly Phe Ala Arg
145                 150


<210> SEQ ID NO 3
<211> LENGTH: 615
<212> TYPE: DNA
<213> ORGANISM: Momordica charantia
<220> FEATURE:
<221> NAME/KEY: misc_feature
<222> LOCATION: 567, 591, 593
<223> OTHER INFORMATION: n = A,T,C or G

<400> SEQUENCE: 3

gtttgtggcg ctagcctttg tgatctctca tggctatgtc cgtggaccct ctggtggtcg     60

gccgagtgat cggagacgtg gtcgacatgt ttgtgccaac tgctaacctg gcagtctact    120

tcaactccaa acatgttact aatggttgcg acattaagcc ttctcttgcg gttaacccac    180

caaggctcgt cattccgggc catcctcgcg acctttacac tttggtgatg acagatccag    240

atgctccgag tcctagcgaa cctcatatga gagaatgggt ccattggata attgtagaca    300

ttcccggagg ctcaacaatg acccaaggga aggagattct gccgtacacc ggcccacgtc    360

cacccatcgg aatccaccgc tacatccttt tactgttcaa gcaaaagggt cctgtggggt    420

tgatcgagca accaccgagc cgcgcaaact tcagcactcg cctgtttgct aagcacctcg    480

acctggacct gccggtggcg gccacctact tcaactctca gaaggaacca gccaccaaaa    540

agttcgcaat gtaatctgaa ccaagtngtc aacccaaacc aaaaaaaaat ngnagtcatc    600

cacgggcaaa atttc                                                      615


<210> SEQ ID NO 4
<211> LENGTH: 174
<212> TYPE: PRT
<213> ORGANISM: Momordica charantia

<400> SEQUENCE: 4

Met Ala Met Ser Val Asp Pro Leu Val Val Gly Arg Val Ile Gly Asp
 1               5                  10                  15

Val Val Asp Met Phe Val Pro Thr Ala Asn Leu Ala Val Tyr Phe Asn
            20                  25                  30

Ser Lys His Val Thr Asn Gly Cys Asp Ile Lys Pro Ser Leu Ala Val
        35                  40                  45

Asn Pro Pro Arg Leu Val Ile Pro Gly His Pro Arg Asp Leu Tyr Thr
    50                  55                  60

Leu Val Met Thr Asp Pro Asp Ala Pro Ser Pro Ser Glu Pro His Met
65                  70                  75                  80

Arg Glu Trp Val His Trp Ile Ile Val Asp Ile Pro Gly Gly Ser Thr
                85                  90                  95
```

```
Met Thr Gln Gly Lys Glu Ile Leu Pro Tyr Thr Gly Pro Arg Pro Pro
            100                 105                 110

Ile Gly Ile His Arg Tyr Ile Leu Leu Leu Phe Lys Gln Lys Gly Pro
        115                 120                 125

Val Gly Leu Ile Glu Gln Pro Pro Ser Arg Ala Asn Phe Ser Thr Arg
    130                 135                 140

Leu Phe Ala Lys His Leu Asp Leu Asp Leu Pro Val Ala Ala Thr Tyr
145                 150                 155                 160

Phe Asn Ser Gln Lys Glu Pro Ala Thr Lys Lys Phe Ala Met
                165                 170


<210> SEQ ID NO 5
<211> LENGTH: 859
<212> TYPE: DNA
<213> ORGANISM: Impatiens balsamia

<400> SEQUENCE: 5

gcacgagagc tcatctttcc cagttttgct ccccttttg gctaaaatgt ctcagatctc      60

tgcctccatt gaccctctca ttatgtgcag aatcatagga gatgtggttg atgtgtttgt    120

tcccaccacg gctatgaatg tctactttgg gaacaagcat gttaccaatg gctgtaacat    180

caagccttcc atggcttatg atgccccaaa tgtcactatt tctgggatgc ctcatgagct    240

ttacactctt gtgatgacag atccagatgc tccaagtcca agtgagccct ccatgaggga    300

atgggtccac tgggttgtga ccaacattcc cgggggcagc agtgcggctc aagggaaaga    360

gctggtgtcc tacatgggtc catgcccagc tattgggatt catcgctaca ttttgatcct    420

gtaccgtcag tccatatatg tggaccagaa cattgagaag cctaacatca taaccagggc    480

caacttcagc accagggctt tctctcatca cctttgcctg ggagttcctg tggccactgt    540

ttacttcaat gctcagaagg agcccctgaa ccagcgcaag aatgtgtgaa ggaacggccc    600

tggagcggcg agagaacgtg gagcaagcta cttcgtttgt cttttccttt tagtataagt    660

aatatcatgc attagcatga ccctaagaat aattgatgtt gtgggatatg tgtgttttac    720

catctctttg tttggttatg ttatgcattt ccctttaggc tttaatgttt gtatgcattt    780

ccctttggct taatatttca atgcatttcc ctcaaaaaaa aaaaaaaaaa aaaaaaaaaa    840

aaaaaaaaaa aaaaaaaaa                                                  859


<210> SEQ ID NO 6
<211> LENGTH: 180
<212> TYPE: PRT
<213> ORGANISM: Impatiens balsamia

<400> SEQUENCE: 6

Met Ser Gln Ile Ser Ala Ser Ile Asp Pro Leu Ile Met Cys Arg Ile
 1               5                  10                  15

Ile Gly Asp Val Val Asp Val Phe Val Pro Thr Thr Ala Met Asn Val
            20                  25                  30

Tyr Phe Gly Asn Lys His Val Thr Asn Gly Cys Asn Ile Lys Pro Ser
        35                  40                  45

Met Ala Tyr Asp Ala Pro Asn Val Thr Ile Ser Gly Met Pro His Glu
    50                  55                  60

Leu Tyr Thr Leu Val Met Thr Asp Pro Asp Ala Pro Ser Pro Ser Glu
65                  70                  75                  80

Pro Ser Met Arg Glu Trp Val His Trp Val Val Thr Asn Ile Pro Gly
                85                  90                  95
```

-continued

Gly Ser Ser Ala Ala Gln Gly Lys Glu Leu Val Ser Tyr Met Gly Pro
100 105 110

Cys Pro Ala Ile Gly Ile His Arg Tyr Ile Leu Ile Leu Tyr Arg Gln
115 120 125

Ser Ile Tyr Val Asp Gln Asn Ile Glu Lys Pro Asn Ile Ile Thr Arg
130 135 140

Ala Asn Phe Ser Thr Arg Ala Phe Ser His His Leu Cys Leu Gly Val
145 150 155 160

Pro Val Ala Thr Val Tyr Phe Asn Ala Gln Lys Glu Pro Leu Asn Gln
165 170 175

Arg Lys Asn Val
180

<210> SEQ ID NO 7
<211> LENGTH: 1078
<212> TYPE: DNA
<213> ORGANISM: Zea mays

<400> SEQUENCE: 7
ggcgcgccgg ccggccggtc gattccccca ctccactcgc cgcccgcggc tgggctgcgc 60
tgcgcatcga cgacggacga cgacacaatc acccccaccc cccgtccaat cagcagcgga 120
cgagggacga ccacggcccc ccgtctgccg cacgcgcgcc cgctctgcca gctgctgcta 180
ctactgctaa acctcgccca ccagtcgcgt gaggaaatag caacctgctg agctcgctcg 240
ttcgctcgct cgcctgcctt cttccctggg caagctagct agctaggatc gaggaggagc 300
tctgcccggc catgcagcgt ggggatccgc tggtggtggg ccgcatcatc ggcgacgtgg 360
tggacccctt cgtgcgccgg gtgccgctcc gcgtcgccta cgccgcgcgc gaggtctcca 420
acggctgcga gctcaggccc tccgccatcg ccgaccagcc gcgcgtcgag gtcggcggac 480
ccgacatgcg caccttctac accctcgtga tggtagatcc tgatgcgccg agccccagcg 540
atcccaacct cagggagtac ctgcactggc tggtcactga tattccggcg acgactggag 600
tatcttttgg gaccgaggtc gtgtgctacg agagcccacg gccggtgctg gggatccacc 660
gggtcgtgtt tctgctcttc cagcagctcg gccggcagac ggtgtacgcc ccggggtggc 720
ggcagaactt cagcacccgc gacttcgccg agctctacaa cctcggcttg ccggtcgccg 780
ccgtctactt caactgccag agggagtccg gaaccggtgg gagaagaatg tgatctcgac 840
ccggccgggt ggaaattaat aagatgacgg gtaatcgggt atatgtatat atttatatat 900
atatgtatat gtacgtgtat ttgatctggt ggcctttggt tatattgggt ggggtgtatt 960
tgatatatta tctgtggcag attggcgcat tctctggcgc atatttgata gctacatgta 1020
tctatttata cagatataaa gcgagcaata atatgcatat gagagggttc agccaaaa 1078

<210> SEQ ID NO 8
<211> LENGTH: 173
<212> TYPE: PRT
<213> ORGANISM: Zea mays

<400> SEQUENCE: 8

Met Gln Arg Gly Asp Pro Leu Val Val Gly Arg Ile Ile Gly Asp Val
1 5 10 15

Val Asp Pro Phe Val Arg Arg Val Pro Leu Arg Val Ala Tyr Ala Ala
20 25 30

Arg Glu Val Ser Asn Gly Cys Glu Leu Arg Pro Ser Ala Ile Ala Asp
35 40 45

```
Gln Pro Arg Val Glu Val Gly Gly Pro Asp Met Arg Thr Phe Tyr Thr
    50                  55                  60

Leu Val Met Val Asp Pro Asp Ala Pro Ser Pro Ser Asp Pro Asn Leu
65                  70                  75                  80

Arg Glu Tyr Leu His Trp Leu Val Thr Asp Ile Pro Ala Thr Thr Gly
                85                  90                  95

Val Ser Phe Gly Thr Glu Val Val Cys Tyr Glu Ser Pro Arg Pro Val
            100                 105                 110

Leu Gly Ile His Arg Val Val Phe Leu Leu Phe Gln Gln Leu Gly Arg
        115                 120                 125

Gln Thr Val Tyr Ala Pro Gly Trp Arg Gln Asn Phe Ser Thr Arg Asp
    130                 135                 140

Phe Ala Glu Leu Tyr Asn Leu Gly Leu Pro Val Ala Ala Val Tyr Phe
145                 150                 155                 160

Asn Cys Gln Arg Glu Ser Gly Thr Gly Gly Arg Arg Met
                165                 170


<210> SEQ ID NO 9
<211> LENGTH: 929
<212> TYPE: DNA
<213> ORGANISM: Zea mays

<400> SEQUENCE: 9

gcacgagaag aaaccgaacg agggtttagc tagcaaaata aacagaagca agcaagctag      60

ctagagctaa ggatcgagat cgagatcgac cgaccgacga cgatcagcat ggcgcgcttc     120

gtggatccgc tggtggtggg gcgggtgatc ggcgaggtgg tggacctgtt cgtgccttcc     180

atctccatga ccgtcgccta tgatggctcc aaggacatca gcaacggctg cctcctcaag     240

ccgtccgcca ccgccgcgcc gccgctcgtc cgcatctccg gccgccgcaa cgacctctac     300

acgctgatca tgacggaccc cgatgcgcct agccccagca acccgaccat gagagagtac     360

ctccactgga tagtgattaa cataccagga ggaacagatg ctactaaagg tgaggaggtg     420

gtggagtaca tgggcccgcg gccgccggtg ggcatccacc gctacgtgct ggtgctgttc     480

gagcagaaga cgcgcgtgca cgcggaggcc cccggcgacc gcgccaactt caagacgcgc     540

gcgttcgcgg cggcgcacga gctcggcctc cccactgccg tcgtctactt caacgcgcag     600

aaggagcccg ccagccgccg ccgctagcta gcagctcctc tctgaggcat gccagatgca     660

tgcgtgtgcg tgcaggtgca accaccgcac tgccggcggc tacgtatgac cggtgaataa     720

aaagttttac tgcaccgtaa gcatgctcgc cctgttgcta ttggtatatg ttagcagtgt     780

ggcagtctgt atgtagtagc tattcgcttg catctatgca ctctatgtta gtatgcgtac     840

gtgtggttcc ggaacttttg gagtcttatc taaatactat tgagtaaaac tccagtagtt     900

cactcttaaa caaaaaaaaa aaaaaaaaa                                       929


<210> SEQ ID NO 10
<211> LENGTH: 172
<212> TYPE: PRT
<213> ORGANISM: Zea mays

<400> SEQUENCE: 10

Met Ala Arg Phe Val Asp Pro Leu Val Val Gly Arg Val Ile Gly Glu
 1               5                  10                  15

Val Val Asp Leu Phe Val Pro Ser Ile Ser Met Thr Val Ala Tyr Asp
            20                  25                  30
```

-continued

```
Gly Ser Lys Asp Ile Ser Asn Gly Cys Leu Leu Lys Pro Ser Ala Thr
        35                  40                  45

Ala Ala Pro Pro Leu Val Arg Ile Ser Gly Arg Arg Asn Asp Leu Tyr
    50                  55                  60

Thr Leu Ile Met Thr Asp Pro Asp Ala Pro Ser Pro Ser Asn Pro Thr
65                  70                  75                  80

Met Arg Glu Tyr Leu His Trp Ile Val Ile Asn Ile Pro Gly Gly Thr
                85                  90                  95

Asp Ala Thr Lys Gly Glu Glu Val Val Glu Tyr Met Gly Pro Arg Pro
            100                 105                 110

Pro Val Gly Ile His Arg Tyr Val Leu Val Leu Phe Glu Gln Lys Thr
        115                 120                 125

Arg Val His Ala Glu Ala Pro Gly Asp Arg Ala Asn Phe Lys Thr Arg
    130                 135                 140

Ala Phe Ala Ala Ala His Glu Leu Gly Leu Pro Thr Ala Val Val Tyr
145                 150                 155                 160

Phe Asn Ala Gln Lys Glu Pro Ala Ser Arg Arg Arg
                165                 170


<210> SEQ ID NO 11
<211> LENGTH: 899
<212> TYPE: DNA
<213> ORGANISM: Zea mays

<400> SEQUENCE: 11

ttcaagccaa gttagcttgc ctcgaagatt gccaatcata gctagccatg tcaagggacc      60

cacttgttgt aggcaacgta gttggagata tcttggaccc atttatcaaa tcagcatcac     120

tcagagtcct atacaacaat agagaactga ctaatggatc tgagttcagg ccatcgcaag     180

tagcttatga accaaggatt gagattgctg gatatgacat gaggaccctt tacactttgg     240

taatggtgga tcctgactca ccaagtccaa gcaatccaac aaaaagagag taccttcact     300

ggttggtgac agatattcca gaatcaacag atgtgagctt tggaaatgag gtagtaagct     360

atgaaagccc aaagccaagt gctggaatac atcgcttcgt ctttgttctg gtccgccaat     420

ctgtcaggca aactatttat gcgccaggat ggagacaaaa tttcaacaca agagacttct     480

cagcactcta taatctagga ccacctgtgg cctcagtgtt cttcaactgc caaagggaga     540

atgggtgcgg tggcagacga tatattagat gatactcact ccgttctttt ttatttgtcg     600

cgttttagtt taaaaataaa ctagcggacg acaaatattc gagaacggag gtagtattag     660

aataacctcc tctacatgag gactgacgga attctgtatg aggccaagca caccgaatgg     720

gtagtaaacg ctggacctta atttctagac tactttccca cctctacaag atttgactat     780

gctagaaacg aatttcactt accatgtgaa atgtgataaa tatattccaa ctatatgttc     840

ctgcctcctt gataatgaat actactcagc attggttttg taaaaaaaaa aaaaaaaaa      899


<210> SEQ ID NO 12
<211> LENGTH: 174
<212> TYPE: PRT
<213> ORGANISM: Zea mays

<400> SEQUENCE: 12

Met Ser Arg Asp Pro Leu Val Val Gly Asn Val Val Gly Asp Ile Leu
 1               5                  10                  15

Asp Pro Phe Ile Lys Ser Ala Ser Leu Arg Val Leu Tyr Asn Asn Arg
            20                  25                  30
```

-continued

```
Glu Leu Thr Asn Gly Ser Glu Phe Arg Pro Ser Gln Val Ala Tyr Glu
        35                  40                  45

Pro Arg Ile Glu Ile Ala Gly Tyr Asp Met Arg Thr Leu Tyr Thr Leu
    50                  55                  60

Val Met Val Asp Pro Asp Ser Pro Ser Pro Ser Asn Pro Thr Lys Arg
65                  70                  75                  80

Glu Tyr Leu His Trp Leu Val Thr Asp Ile Pro Glu Ser Thr Asp Val
                85                  90                  95

Ser Phe Gly Asn Glu Val Val Ser Tyr Glu Ser Pro Lys Pro Ser Ala
            100                 105                 110

Gly Ile His Arg Phe Val Phe Val Leu Val Arg Gln Ser Val Arg Gln
        115                 120                 125

Thr Ile Tyr Ala Pro Gly Trp Arg Gln Asn Phe Asn Thr Arg Asp Phe
    130                 135                 140

Ser Ala Leu Tyr Asn Leu Gly Pro Pro Val Ala Ser Val Phe Phe Asn
145                 150                 155                 160

Cys Gln Arg Glu Asn Gly Cys Gly Gly Arg Arg Tyr Ile Arg
                165                 170


<210> SEQ ID NO 13
<211> LENGTH: 893
<212> TYPE: DNA
<213> ORGANISM: Zea mays

<400> SEQUENCE: 13

ggccgtagat agtaagtaga tcacgcagcg cagtagctct ggattaatta ataataattg     60

ctcgtgcgtg tgtccagagc cgccatggct gcccatgtgg acccgctggt tgtggggagg    120

gtgatcggcg acgtggtgga cttgttcgtg ccgacggtgg ccgtgtcggc gcgcttcggc    180

gccaaggacc tcaccaacgg ctgcgagatc aagccatccg tcgccgcggc cgctcccgcc    240

gtcctcatcg ccggcagggc caacgacctc ttcaccctgg ttatgactga cccagatgct    300

ccgagcccta gcgagccaac gatgagggag ttgctccact ggctggtggt taacatacca    360

ggtggagcag atgcttctca aggcggtgag acggtggtgc cgtacgtggg cccgcgcccg    420

ccggtgggta tccaccgcta cgtgctggtg gtgtaccagc agaaggcccg cgtcacggct    480

ccgccgtcgc tggcgccggc gacggaggcg acgcgcgcac ggttcagcaa ccgcgccttc    540

gccgaccgcc atgacctagg cctccctgtc gccgccatgt tcttcaacgc gcagaaggag    600

acagctagtc gccgccgcca ctactgagac aggctgatcg tcgtccaacg gcaattacgt    660

acccagcaaa gcttaagcca gccgctgcag tcactcatct catcgagaag aagacaatct    720

tcctagtcgc tgttcttgcc aagtactagt accttgttaa ttattatgta agctaaaccc    780

gtgtgcctgt gattatattg ggacgtgtct cgctttaata caaccgctca acttgtggcg    840

tttaattatt ttatttatta gatataccaa ggtgtcatca agtcacttgc ctt           893


<210> SEQ ID NO 14
<211> LENGTH: 180
<212> TYPE: PRT
<213> ORGANISM: Zea mays

<400> SEQUENCE: 14

Met Ala Ala His Val Asp Pro Leu Val Val Gly Arg Val Ile Gly Asp
 1               5                  10                  15

Val Val Asp Leu Phe Val Pro Thr Val Ala Val Ser Ala Arg Phe Gly
            20                  25                  30
```

-continued

```
Ala Lys Asp Leu Thr Asn Gly Cys Glu Ile Lys Pro Ser Val Ala Ala
        35                  40                  45

Ala Ala Pro Ala Val Leu Ile Ala Gly Arg Ala Asn Asp Leu Phe Thr
    50                  55                  60

Leu Val Met Thr Asp Pro Asp Ala Pro Ser Pro Ser Glu Pro Thr Met
65                  70                  75                  80

Arg Glu Leu Leu His Trp Leu Val Val Asn Ile Pro Gly Gly Ala Asp
                85                  90                  95

Ala Ser Gln Gly Gly Glu Thr Val Val Pro Tyr Val Gly Pro Arg Pro
            100                 105                 110

Pro Val Gly Ile His Arg Tyr Val Leu Val Val Tyr Gln Gln Lys Ala
        115                 120                 125

Arg Val Thr Ala Pro Pro Ser Leu Ala Pro Ala Thr Glu Ala Thr Arg
    130                 135                 140

Ala Arg Phe Ser Asn Arg Ala Phe Ala Asp Arg His Asp Leu Gly Leu
145                 150                 155                 160

Pro Val Ala Ala Met Phe Phe Asn Ala Gln Lys Glu Thr Ala Ser Arg
                165                 170                 175

Arg Arg His Tyr
            180


<210> SEQ ID NO 15
<211> LENGTH: 837
<212> TYPE: DNA
<213> ORGANISM: Zea mays

<400> SEQUENCE: 15

ccacgcgtcc ggtactgtga gagtaaggct aaagtcgccg gataatataa gaccagcaat     60

aacaagctag tttgccctcg ttctccaaca aaatgtctga tgtggagccg ctggttctgg    120

ctcatgtcat acgagatgtg ttggattcat ttgcaccaag tatcgggctc agaataacct    180

acaacagcag gttacttcta tcaggtgttg agctgaaacc atccgcggtt gtgaataagc    240

caagagttga tgttgggggc accgacctca gggtgttcta cacattggta ttagtggatc    300

cagatgcccc aagcccaagc aatccatcac tgagggagta tctgcactgg atggtgatag    360

acattcctgg aacaactgga gccagctttg gtcaggagct catgttttac gagaggccag    420

agccgaggtc cggcatacac cgcatggtgt tcgtgctgtt ccggcagctc ggcaggggga    480

cggtgtttgc accagacatg cggcacaact tcaactgcaa gagcttcgcc cgtcagtacc    540

acctggacgt cgtggctgcc acgtatttca actgccaaag ggaggcagga tccgggggca    600

gaaggttcag gccggagagc tcgtaaggaa tgaagcatgc acagaagaag actgcagcgc    660

tttcgcatgc atatgatcta tcgtcgtcct gcggaatata tatatagtaa ccgttgttat    720

atggaataat gtgcatgaaa ttggtatcag atgcaccgac ccgtacgtac gtaattaatg    780

tttgttatta cacgcagaca tataatatac atactcattc acaaaaaaaa aaaaaaa       837


<210> SEQ ID NO 16
<211> LENGTH: 177
<212> TYPE: PRT
<213> ORGANISM: Zea mays

<400> SEQUENCE: 16

Met Ser Asp Val Glu Pro Leu Val Leu Ala His Val Ile Arg Asp Val
 1               5                  10                  15

Leu Asp Ser Phe Ala Pro Ser Ile Gly Leu Arg Ile Thr Tyr Asn Ser
            20                  25                  30
```

```
Arg Leu Leu Leu Ser Gly Val Glu Leu Lys Pro Ser Ala Val Val Asn
        35                  40                  45

Lys Pro Arg Val Asp Val Gly Gly Thr Asp Leu Arg Val Phe Tyr Thr
    50                  55                  60

Leu Val Leu Val Asp Pro Asp Ala Pro Ser Pro Ser Asn Pro Ser Leu
65                  70                  75                  80

Arg Glu Tyr Leu His Trp Met Val Ile Asp Ile Pro Gly Thr Thr Gly
                85                  90                  95

Ala Ser Phe Gly Gln Glu Leu Met Phe Tyr Glu Arg Pro Glu Pro Arg
            100                 105                 110

Ser Gly Ile His Arg Met Val Phe Val Leu Phe Arg Gln Leu Gly Arg
        115                 120                 125

Gly Thr Val Phe Ala Pro Asp Met Arg His Asn Phe Asn Cys Lys Ser
    130                 135                 140

Phe Ala Arg Gln Tyr His Leu Asp Val Val Ala Ala Thr Tyr Phe Asn
145                 150                 155                 160

Cys Gln Arg Glu Ala Gly Ser Gly Gly Arg Arg Phe Arg Pro Glu Ser
                165                 170                 175

Ser


<210> SEQ ID NO 17
<211> LENGTH: 1191
<212> TYPE: DNA
<213> ORGANISM: Zea mays

<400> SEQUENCE: 17

ccacgcgtcc ggtagtacct tggccaaacg acttagctat caagctcgac cgaagctaag     60

ctaccaagct agtagccttc ttggtcacgt accggccgtt gttgattgca gcggtcaagc    120

acacacaagc taggcagcta gctagctaga gctagggtcg tcggatagat cgacatggcc    180

ggcagggaca gggagccgct ggtggttggt agggtggtcg gcgacgtgct ggaccccttc    240

gtccggacca ccaacctcag ggtcagctac ggggccagga ccgtgtccaa cggctgcgag    300

ctcaagccgt ccatggtggt gcaccagccc agggtcgagg tcgggggacc tgacatgagg    360

accttctaca ccctcgtgat ggtggacccg gatgctccga gcccaagcga cccgaacctt    420

agggagtacc tacactggct ggtgacggat attccgggaa ctactggggc agcatttggg    480

caagaggtga tctgctacga gagccctcgg ccgaccatgg ggatccaccg cttcgtgctg    540

gtgctgttcc agcagctggg gcggcagacg gtgtacgccc cgggctggcg ccagaacttc    600

aacaccaggg acttcgccga gctctacaac ctgggcccgc ccgtcgccgc cgtctacttc    660

aactgccagc gtgaggccgg ctctgggggc aggaggatgt actcgtgatc ggatgcatgg    720

ttacatacca tgcacactac tcactccatc gtctccatac atgtagacgg acgatggtgc    780

atgcatcgat cgtcaactac tcaacaatta cgaactagaa atacacgcgt atatatacat    840

atataaatat gcatatatac cggtactgta catgtcgccg tacacgcgca ggtggctgct    900

gctagcttgc tataccggcc ggtggtactg agcaggcagc atgcgctata tacttgcttg    960

gcgacgacgt gcagtgtgtg tatacaataa tgagcggccg gccggctagc agggcgacga   1020

gccgtggctt tagcaataca tataccatgc aggcatgtgt gtgtgcagtg cgtgccaagg   1080

tacggtaacg tattaattat tgtgcacata cacatatgta tacgtacata tgcgtaaata   1140

tgaatgtgta cgtatacata tgcatgctgg ttaattaaaa aaaaaaaaaa a            1191
```

-continued

<210> SEQ ID NO 18
<211> LENGTH: 177
<212> TYPE: PRT
<213> ORGANISM: Zea mays

<400> SEQUENCE: 18

```
Met Ala Gly Arg Asp Arg Glu Pro Leu Val Val Gly Arg Val Val Gly
 1               5                  10                  15

Asp Val Leu Asp Pro Phe Val Arg Thr Thr Asn Leu Arg Val Ser Tyr
            20                  25                  30

Gly Ala Arg Thr Val Ser Asn Gly Cys Glu Leu Lys Pro Ser Met Val
        35                  40                  45

Val His Gln Pro Arg Val Glu Val Gly Gly Pro Asp Met Arg Thr Phe
    50                  55                  60

Tyr Thr Leu Val Met Val Asp Pro Asp Ala Pro Ser Pro Ser Asp Pro
65                  70                  75                  80

Asn Leu Arg Glu Tyr Leu His Trp Leu Val Thr Asp Ile Pro Gly Thr
                85                  90                  95

Thr Gly Ala Ala Phe Gly Gln Glu Val Ile Cys Tyr Glu Ser Pro Arg
            100                 105                 110

Pro Thr Met Gly Ile His Arg Phe Val Leu Val Leu Phe Gln Gln Leu
        115                 120                 125

Gly Arg Gln Thr Val Tyr Ala Pro Gly Trp Arg Gln Asn Phe Asn Thr
    130                 135                 140

Arg Asp Phe Ala Glu Leu Tyr Asn Leu Gly Pro Pro Val Ala Ala Val
145                 150                 155                 160

Tyr Phe Asn Cys Gln Arg Glu Ala Gly Ser Gly Gly Arg Arg Met Tyr
                165                 170                 175

Ser
```

<210> SEQ ID NO 19
<211> LENGTH: 902
<212> TYPE: DNA
<213> ORGANISM: Zea mays

<400> SEQUENCE: 19

```
ccacgcgtcc ggtattcttg agtgcattcg cttgctccat tcagtcagag cattccttgt      60

gcaaaattca aatacctgtc acaccaacca tgtctaggtc tgtggagcct ctcatagtcg     120

ggcgggtgat tggagaagtt ctcgactcct ttaacccatg tgtcaagatg atagtaacct     180

acaactcaaa caaacttgta ttcaatggcc atgagatcta cccatcagca attgtatcta     240

aacctagggt agaggttcaa gggggtgatt tgcggtcttt cttcacattg gttatgacag     300

acccagatgt tccaggacca agtgatccat atctaaggga gcaccttcat tggatcgtga     360

ctgatatacc tgggacaaca gatgcctcct ttgggcgaga ggtcataagc tatgagagcc     420

caagacctaa catcggtatc cacaggttca tttttgtgct cttcaagcag aagggtaggc     480

aaactgtaac cgtgccatcc ttcagagatc atttcaacac ccggcagttt gctgaggaaa     540

atgaccttgg cctcccagta gctgctgtct acttcaatgc acagagagaa actgcagcta     600

ggagacgttg aaaattccag ctcttattgt ccacctgatg ataataaagg ccttctgatc     660

ttctttctag gaagccaatg aacttattct acattaaatt ctcctgagcc ctaccgtata     720

aataaaccag atgcgttttg ctgattgtat tagtattaga atgctttgta cgtggcaaga     780

atgagaatta caaatggtca atgcttgtgg taaaatttga tgtgtaaaaa aaaaaaaaaa     840

aaaaaaaaaa aaaaaaaaaa aaaaaaaaaa aaaaaaaaaa aaaaaaaaaa aaaaaaaaaa     900
```

```
gg                                                                902

<210> SEQ ID NO 20
<211> LENGTH: 173
<212> TYPE: PRT
<213> ORGANISM: Zea mays

<400> SEQUENCE: 20

Met Ser Arg Ser Val Glu Pro Leu Ile Val Gly Arg Val Ile Gly Glu
 1               5                  10                  15

Val Leu Asp Ser Phe Asn Pro Cys Val Lys Met Ile Val Thr Tyr Asn
            20                  25                  30

Ser Asn Lys Leu Val Phe Asn Gly His Glu Ile Tyr Pro Ser Ala Ile
        35                  40                  45

Val Ser Lys Pro Arg Val Glu Val Gln Gly Gly Asp Leu Arg Ser Phe
    50                  55                  60

Phe Thr Leu Val Met Thr Asp Pro Asp Val Pro Gly Pro Ser Asp Pro
65                  70                  75                  80

Tyr Leu Arg Glu His Leu His Trp Ile Val Thr Asp Ile Pro Gly Thr
                85                  90                  95

Thr Asp Ala Ser Phe Gly Arg Glu Val Ile Ser Tyr Glu Ser Pro Arg
            100                 105                 110

Pro Asn Ile Gly Ile His Arg Phe Ile Phe Val Leu Phe Lys Gln Lys
        115                 120                 125

Gly Arg Gln Thr Val Thr Val Pro Ser Phe Arg Asp His Phe Asn Thr
    130                 135                 140

Arg Gln Phe Ala Glu Glu Asn Asp Leu Gly Leu Pro Val Ala Ala Val
145                 150                 155                 160

Tyr Phe Asn Ala Gln Arg Glu Thr Ala Ala Arg Arg Arg
                165                 170


<210> SEQ ID NO 21
<211> LENGTH: 980
<212> TYPE: DNA
<213> ORGANISM: Zea mays

<400> SEQUENCE: 21

ccacgcgtcc gcgcacatag ggaacagaag ctactagctc cagcacaaaa cacctactgc     60

ttcaactgta ccgttagaca tgtcaagggt gttggagcct ctcattgtgg ggaaagtgat    120

tggtgaggtc ctggaccatt tcaaccccac ggtgaagatg gtggtcacct acaactccaa    180

caagcaggtg ttcaacgggc acgagttctt cccttcggca gtggccgcca agccgcgtgt    240

tgaggtccaa gggggcgacc tcaggtcctt cttcacgttg gtgatgaccg accccgatgt    300

tcctggacct agtgatccat acttgaggga gcaccttcac tggattgtca ctgatattcc    360

tgggactacc gatgcttctt ttgggaaaga ggtggtgagc tacgagatcc caaagccaaa    420

cattggcatc cacaggttca tctttgtgct gttccggcag aagagccggc aagcggtgaa    480

cccgccgtcg tcgaaggacc gcttcagcac ccgccagttc gctgaggaga acgacctcgg    540

cctccccgtc gccgccgtct acttcaacgc gcagcgcgag accgccgccc gccgacgcta    600

accgtacggc tcaacgtacg aaagaagacc atcctacgac gcttgcaatt agctgggcaa    660

gcaaagcttt ttttttcatc ctgagtcgat ctttacgtat gtatgtttgt ttaaataaaa    720

aggtagctaa tcagctgctt ggctgtgacc ccacgagcta gcagctacaa cctactggta    780

catgctgcac attttagctg atttatgaag gtgacaatat gattggtagg gttgcaatgt    840
```

```
tgactgggca tagtgtaaca acttaagcaa tggccatggg cgagtacgtg tcgagtggtg    900

aagttgaagg gaagtttata ttaaaagcaa ggccatgtct tgtattacct tgcctaaaaa    960

aaaaaaaaaa aaaaaaaaag                                                980


<210> SEQ ID NO 22
<211> LENGTH: 173
<212> TYPE: PRT
<213> ORGANISM: Zea mays

<400> SEQUENCE: 22

Met Ser Arg Val Leu Glu Pro Leu Ile Val Gly Lys Val Ile Gly Glu
 1               5                  10                  15

Val Leu Asp Asn Phe Asn Pro Thr Val Lys Met Thr Ala Thr Tyr Gly
            20                  25                  30

Ala Asn Lys Gln Val Phe Asn Gly His Glu Phe Phe Pro Ser Ala Val
        35                  40                  45

Ala Gly Lys Pro Arg Val Glu Val Gln Gly Gly Asp Leu Arg Ser Phe
    50                  55                  60

Phe Thr Leu Val Met Thr Asp Pro Asp Val Pro Gly Pro Ser Asp Pro
65                  70                  75                  80

Tyr Leu Arg Glu His Leu His Trp Ile Val Thr Asp Ile Pro Gly Thr
                85                  90                  95

Thr Asp Ala Ser Phe Gly Arg Glu Val Val Ser Tyr Glu Ser Pro Arg
            100                 105                 110

Pro Asn Ile Gly Ile His Arg Phe Ile Leu Val Leu Phe Arg Gln Lys
        115                 120                 125

Arg Arg Gln Ala Val Ser Pro Pro Pro Ser Arg Asp Arg Phe Ser Thr
    130                 135                 140

Arg Gln Phe Ala Glu Asp Asn Asp Leu Gly Leu Pro Val Ala Ala Val
145                 150                 155                 160

Tyr Phe Asn Ala Gln Arg Glu Thr Ala Ala Arg Arg Arg
                165                 170


<210> SEQ ID NO 23
<211> LENGTH: 405
<212> TYPE: DNA
<213> ORGANISM: Oryza sativa
<220> FEATURE:
<221> NAME/KEY: misc_feature
<222> LOCATION: 346, 365
<223> OTHER INFORMATION: n = A,T,C or G

<400> SEQUENCE: 23

ggagagatcg atggcccgtt tcgtggatcc gctggtggtg ggacgggtga tcggggaggt     60

ggtggatttg ttcgttccat ccatctccat gaccgccgcc tacggcgaca gggacatcag    120

caacggctgc ctcgtccgcc catccgccgc cgactaccct cccctcgtcc gcatctccgg    180

ccgccgcaac gacctctaca ccctgatcat gacggacccg gacgcaccta gccctagcga    240

cccatccatg agggagtttc tccactggat cgtggttaac ataccggggg gaacagatgc    300

atctaaaggt gaggagatgg tggagtacat ggggccacgg gcgacngtgg ggataaacaa    360

gtacnttgct ggtgctgtac aacaaaaagc gcgctttctg ggacg                    405


<210> SEQ ID NO 24
<211> LENGTH: 128
<212> TYPE: PRT
<213> ORGANISM: Oryza sativa
```

```
<220> FEATURE:
<221> NAME/KEY: VARIANT
<222> LOCATION: 119
<223> OTHER INFORMATION: Xaa = Any Amino Acid

<400> SEQUENCE: 24

Met Ala Arg Phe Val Asp Pro Leu Val Val Gly Arg Val Ile Gly Glu
 1               5                  10                  15

Val Val Asp Leu Phe Val Pro Ser Ile Ser Met Thr Ala Ala Tyr Gly
            20                  25                  30

Asp Arg Asp Ile Ser Asn Gly Cys Leu Val Arg Pro Ser Ala Ala Asp
        35                  40                  45

Tyr Pro Pro Leu Val Arg Ile Ser Gly Arg Arg Asn Asp Leu Tyr Thr
    50                  55                  60

Leu Ile Met Thr Asp Pro Asp Ala Pro Ser Pro Ser Asp Pro Ser Met
65                  70                  75                  80

Arg Glu Phe Leu His Trp Ile Val Val Asn Ile Pro Gly Gly Thr Asp
                85                  90                  95

Ala Ser Lys Gly Glu Glu Met Val Glu Tyr Met Gly Pro Arg Ala Thr
            100                 105                 110

Val Gly Ile Asn Lys Tyr Xaa Ala Gly Ala Val Gln Gln Lys Ala Arg
        115                 120                 125


<210> SEQ ID NO 25
<211> LENGTH: 419
<212> TYPE: DNA
<213> ORGANISM: Oryza sativa
<220> FEATURE:
<221> NAME/KEY: misc_feature
<222> LOCATION: 221, 277, 368
<223> OTHER INFORMATION: n = A,T,C or G

<400> SEQUENCE: 25

cttacaccta atcccagcaa cccaaccttg agggaatacc tgcactggat ggtgactgat      60

atcccatcat cgacggacga tagctttggg cgggagatcg taacatacga aagcccaagc     120

cccaccatgg gcatccaccg catcgtgatg gtgttgtatc agcagcttgg gcgcggcacg     180

gtgttcgcgc cgcagtgggt ccagaacttc aacctgcgca ntttcgcgcg ccgtttcaac     240

ctcggcaagc cggtggccgc catgtacttc aactgcnagc gcccgacagg cacaggtggg     300

aggaggccaa ctgattgatc aatatcgtcg atttcgtctt ctagctcttg tacatgttga     360

gtgttganca atataatggc cactcatgca tatatatata tatatatata tatatatat      419


<210> SEQ ID NO 26
<211> LENGTH: 105
<212> TYPE: PRT
<213> ORGANISM: Oryza sativa
<220> FEATURE:
<221> NAME/KEY: VARIANT
<222> LOCATION: 74, 93
<223> OTHER INFORMATION: Xaa = Any Amino Acid

<400> SEQUENCE: 26

Leu Thr Pro Asn Pro Ser Asn Pro Thr Leu Arg Glu Tyr Leu His Trp
 1               5                  10                  15

Met Val Thr Asp Ile Pro Ser Ser Thr Asp Asp Ser Phe Gly Arg Glu
            20                  25                  30

Ile Val Thr Tyr Glu Ser Pro Ser Pro Thr Met Gly Ile His Arg Ile
        35                  40                  45

Val Met Val Leu Tyr Gln Gln Leu Gly Arg Gly Thr Val Phe Ala Pro
```

-continued

```
    50                  55                  60

Gln Trp Val Gln Asn Phe Asn Leu Arg Xaa Phe Ala Arg Arg Phe Asn
65                  70                  75                  80

Leu Gly Lys Pro Val Ala Ala Met Tyr Phe Asn Cys Xaa Arg Pro Thr
                85                  90                  95

Gly Thr Gly Gly Arg Arg Pro Thr Asp
            100                 105


<210> SEQ ID NO 27
<211> LENGTH: 400
<212> TYPE: DNA
<213> ORGANISM: Oryza sativa
<220> FEATURE:
<221> NAME/KEY: misc_feature
<222> LOCATION: 3, 171, 172, 200, 230, 233, 249, 270, 300, 317, 331,
      351, 354, 355, 361, 386, 391, 392
<223> OTHER INFORMATION: n = A,T,C or G

<400> SEQUENCE: 27

aancacagtc acacacacac agcagaagaa gaagaaaccg aacgagggtt tagctagcaa     60

aataaacaga agcaagcaag ctagctagag ctaaggatcg agatcgagat cgaccgaccg    120

acgacgatca actagcatgg cgcgcttcgt ggatccgctg gtggtggggc nngtgatcgg    180

cgaggtggtg gacctgttcn tgccttccat ctccatgacc gtcgcctatn atngccccaa    240

ggacatcanc aacggctgcc tcctcaagcn gtccgccacc gccgcgccgc cggtcgtccn    300

catctccggc cgccgcnacg acctctacac nctgatgcat gacggacccc natnngccta    360

nccccagcaa cccgaccatg agggantacc nncactggat                          400


<210> SEQ ID NO 28
<211> LENGTH: 87
<212> TYPE: PRT
<213> ORGANISM: Oryza sativa
<220> FEATURE:
<221> NAME/KEY: VARIANT
<222> LOCATION: 12, 22, 32, 33, 38, 45, 55, 61, 72, 73, 75, 83, 85
<223> OTHER INFORMATION: Xaa = Any Amino Acid

<400> SEQUENCE: 28

Met Ala Arg Phe Val Asp Pro Leu Val Val Gly Xaa Val Ile Gly Glu
 1               5                  10                  15

Val Val Asp Leu Phe Xaa Pro Ser Ile Ser Met Thr Val Ala Tyr Xaa
            20                  25                  30

Xaa Pro Lys Asp Ile Xaa Asn Gly Cys Leu Leu Lys Xaa Ser Ala Thr
        35                  40                  45

Ala Ala Pro Pro Val Val Xaa Ile Ser Gly Arg Arg Xaa Asp Leu Tyr
    50                  55                  60

Thr Leu Met Met Thr Asp Pro Xaa Xaa Pro Xaa Pro Ser Asn Pro Thr
65                  70                  75                  80

Met Arg Xaa Tyr Xaa His Trp
                85


<210> SEQ ID NO 29
<211> LENGTH: 1226
<212> TYPE: DNA
<213> ORGANISM: Oryza sativa

<400> SEQUENCE: 29

ggcataagta tatatctgac aaattcagag aaattcagag agtcaccgcg agagcttaag     60

ctagctagct agccggccat ggcatcgcat gtggacccgc tggtggtggg gagggtgatc    120
```

-continued

```
ggcgacgtgg tggacctgtt cgtgccgacg acggccatgt cggtgcggtt cgggaccaag    180

gacctcacca acggctgcga gatcaagccg tccgtcgccg ccgcgccgcc cgccgtgcag    240

atcgccggca gggtcaacga gctcttcgct ctggtcatga ctgatccaga tgctcctagc    300

cccagcgagc cgactatgag agagtggctt cactggctgg tggttaacat accaggtgga    360

acagatcctt ctcaagggga tgtggtggtg ccgtacatgg ggccacggcc gccggtgggg    420

atccaccgct acgtgatggt gctgttccag cagaaggcgc gcgtggcggc gccgccgccc    480

gacgaggacg ccgcgcgcgc caggttcagc acgcgcgcct tcgccgaccg ccacgacctc    540

ggcctccccg tcgccgccct ctacttcaac gcccagaagg agcccgccaa ccgccgccgc    600

cgctactagc ctccctcccc tcgctcggcg tcgcccatcc atccatccat ggacggcgac    660

ggcgacctag ctagctaata agccatcggt cggccatgct cgccgtccaa actatcatgc    720

accatatcat gtcgtcgttt atgtggttaa ttaattattt ccggcgtttt attactgtgt    780

ggtgccgtac atggggccac ggccgccggt ggggatccac cgctacgtga tggtgctgtt    840

ccagcagaag gcgcgcgtgg cggcgccgcc gcccgacgag gacgccgcgc gcgccaggtt    900

cagcacgcgc gccttcgccg accgccacga cctcggcctc cccgtcgccg ccctctactt    960

caacgcccag aaggagcccg ccaaccgccg ccgccgctac tagcctccct cccctcgctc   1020

ggcgtcgccc atccatccat ccatggacgg cgacggcgac ctagctagct aataagccat   1080

cggtcggcca tgctcgccgt ccaaactatc atgcaccata tcatgtcgtc gtttatgtgg   1140

ttaattaatt atttccggcg ttttattact gtgtggtgat taaaaaaaaa aaaaaaaaaa   1200

aaaaaaaaaa aaaaaaaaaa aaaaaa                                        1226
```

```
<210> SEQ ID NO 30
<211> LENGTH: 176
<212> TYPE: PRT
<213> ORGANISM: Oryza sativa

<400> SEQUENCE: 30

Met Ala Ser His Val Asp Pro Leu Val Val Gly Arg Val Ile Gly Asp
1               5                   10                  15

Val Val Asp Leu Phe Val Pro Thr Thr Ala Met Ser Val Arg Phe Gly
            20                  25                  30

Thr Lys Asp Leu Thr Asn Gly Cys Glu Ile Lys Pro Ser Val Ala Ala
        35                  40                  45

Ala Pro Pro Ala Val Gln Ile Ala Gly Arg Val Asn Glu Leu Phe Ala
    50                  55                  60

Leu Val Met Thr Asp Pro Asp Ala Pro Ser Pro Ser Glu Pro Thr Met
65                  70                  75                  80

Arg Glu Trp Leu His Trp Leu Val Val Asn Ile Pro Gly Gly Thr Asp
                85                  90                  95

Pro Ser Gln Gly Asp Val Val Val Pro Tyr Met Gly Pro Arg Pro Pro
            100                 105                 110

Val Gly Ile His Arg Tyr Val Met Val Leu Phe Gln Gln Lys Ala Arg
        115                 120                 125

Val Ala Ala Pro Pro Pro Asp Glu Asp Ala Ala Arg Ala Arg Phe Ser
    130                 135                 140

Thr Arg Ala Phe Ala Asp Arg His Asp Leu Gly Leu Pro Val Ala Ala
145                 150                 155                 160

Leu Tyr Phe Asn Ala Gln Lys Glu Pro Ala Asn Arg Arg Arg Arg Tyr
                165                 170                 175
```

<210> SEQ ID NO 31
<211> LENGTH: 1295
<212> TYPE: DNA
<213> ORGANISM: Oryza sativa

<400> SEQUENCE: 31

```
gcacgagatt gcctgcacct agccacatca tatattcaga gagagagctg agagagcagt      60
acaagagtgt atactacact tagcagctca tcagttatta gttcactagt tcagccactg     120
accatcgaat caattcaggt gagataatct tgagatagat atacggccat gtcgagggtg     180
ctggagcctc tcattgtggg gaaggtgatc ggcgaggtgc tggacaactt caaccccacg     240
gtgaagatga cggccaccta cggcgccaac aagcaggtgt tcaacggcca cgagttcttc     300
ccctccgccg tcgccggcaa gccgcgcgtc gaggtccagg gcggcgacct caggtccttc     360
ttcacattgg tgatgactga ccctgatgtg ccagggccta gtgatccata cctgagggag     420
catcttcact ggattgttac tgatattcct gggactactg atgcctcttt tgggagggag     480
gtggtgagct acgagagccc gcggccaaac atcggcatcc acaggttcat cctggtgctg     540
ttccggcaga agcgccggca ggcggtgagc ccgccgccgt cgagggaccg cttcagcacc     600
cgccagttcg ccgaggacaa cgacctcggc ctccccgtcg ccgccgtcta cttcaacgcg     660
cagcgcgaga ccgccgctcg ccgccgctaa tggctaccga cgacggcgac gacgacgacg     720
accctgacac cgcgacgacc gatcttgcat ggacaaaaca atataatcga gcttaattaa     780
ttactactac ttctactggc attttctatt agttttccta tttcccctac attaatttca     840
ctgtcaaata aggcacactg tgattagctg cagctagcta gctttgctcg tgtgtgtgag     900
ctagctagct cgtagctaca gggcaggcct acagactacc agttcgtgct tgtttgcatg     960
cacattatca gattatccta gttgatttgt gaattaatca aggtgatcat aggattgtga    1020
gtgagcaatc gcaatcgcaa tgtgcaagct atggttgact agcagcagtg agagatctct    1080
agctagctac actagttgaa gcaatggcca tccatggcag gagagtccta gcatcccccc    1140
tgcatatatg cctacctact attcaactgc tgttcttcga ttcaattcgc tggtgcttgc    1200
agtgtacttt gtttgatcct gtgatcacta cttcttgcca cttgtttttg taatccgatc    1260
ggtgtcactt tttctgtaaa aaaaaaaaaa aaaaa                                1295
```

<210> SEQ ID NO 32
<211> LENGTH: 173
<212> TYPE: PRT
<213> ORGANISM: Oryza sativa

<400> SEQUENCE: 32

```
Met Ser Arg Val Leu Glu Pro Leu Ile Val Gly Lys Val Ile Gly Glu
 1               5                  10                  15

Val Leu Asp Asn Phe Asn Pro Thr Val Lys Met Thr Ala Thr Tyr Gly
            20                  25                  30

Ala Asn Lys Gln Val Phe Asn Gly His Glu Phe Phe Pro Ser Ala Val
        35                  40                  45

Ala Gly Lys Pro Arg Val Glu Val Gln Gly Gly Asp Leu Arg Ser Phe
    50                  55                  60

Phe Thr Leu Val Met Thr Asp Pro Asp Val Pro Gly Pro Ser Asp Pro
65                  70                  75                  80

Tyr Leu Arg Glu His Leu His Trp Ile Val Thr Asp Ile Pro Gly Thr
                85                  90                  95
```

```
Thr Asp Ala Ser Phe Gly Arg Glu Val Val Ser Tyr Glu Ser Pro Arg
            100                 105                 110

Pro Asn Ile Gly Ile His Arg Phe Ile Leu Val Leu Phe Arg Gln Lys
        115                 120                 125

Arg Arg Gln Ala Val Ser Pro Pro Pro Ser Arg Asp Arg Phe Ser Thr
    130                 135                 140

Arg Gln Phe Ala Glu Asp Asn Asp Leu Gly Leu Pro Val Ala Ala Val
145                 150                 155                 160

Tyr Phe Asn Ala Gln Arg Glu Thr Ala Ala Arg Arg Arg
                165                 170


<210> SEQ ID NO 33
<211> LENGTH: 567
<212> TYPE: DNA
<213> ORGANISM: Oryza sativa
<220> FEATURE:
<221> NAME/KEY: misc_feature
<222> LOCATION: 401, 411, 428, 435, 437, 455, 475, 524, 536, 543
<223> OTHER INFORMATION: n = A,T,C or G

<400> SEQUENCE: 33

ctcaagttag cttcttagca cagcctcttc ttgctcaact cctgaagatc atcaatcttc      60

actagccatg tcaagggacc cacttgtcgt aggacatgtt gttggggata tcttagaccc     120

attcaacaaa tcagcatcac tcaaggtcct atacaacaac aaggaattaa caaatgggtc     180

tgagctcaaa ccgtcacagg tagcaaatga accaaggatt gaaattgctg gccgcgacat     240

aaggaacctt tacactctgg tgatggtgga tcctgactcg ccaagtccaa gcaacccaac     300

aaaaagagaa taccttcatt gggttgggtg acaagacatt ccaagaatcg gcaaatgcta     360

attatggaaa tgaagtttgt cagttatgaa aagcccaaaa ncaaactgca nggatacatc     420

cgttttgncc ttaanantaa ttccgccaat atgtncaaca agactaatta tgcancaaga     480

tgggggaaca aaatttcaat acaaagagaa tttttccgca acgntaaaac cttggncctc     540

ccngtgggaa caatggttct caaattg                                         567


<210> SEQ ID NO 34
<211> LENGTH: 87
<212> TYPE: PRT
<213> ORGANISM: Oryza sativa

<400> SEQUENCE: 34

Met Ser Arg Asp Pro Leu Val Val Gly His Val Val Gly Asp Ile Leu
 1               5                  10                  15

Asp Pro Phe Asn Lys Ser Ala Ser Leu Lys Val Leu Tyr Asn Asn Lys
            20                  25                  30

Glu Leu Thr Asn Gly Ser Glu Leu Lys Pro Ser Gln Val Ala Asn Glu
        35                  40                  45

Pro Arg Ile Glu Ile Ala Gly Arg Asp Ile Arg Asn Leu Tyr Thr Leu
    50                  55                  60

Val Met Val Asp Pro Asp Ser Pro Ser Pro Ser Asn Pro Thr Lys Arg
65                  70                  75                  80

Glu Tyr Leu His Trp Val Gly
                85


<210> SEQ ID NO 35
<211> LENGTH: 850
<212> TYPE: DNA
<213> ORGANISM: Glycine max
```

<400> SEQUENCE: 35

```
atggcagcct ccgtggatcc cctagtggtt ggtcgcgtga tcggcgatgt ggtagacatg     60

ttcattcctt cagtcaacat gtccgtttac tttgggtcga agcacgtcac aaatggctgt    120

gacatcaagc catccattgc catcagccct cctaagctca ccctcaccgg caacatggat    180

aacctctaca cactggttat gactgatcct gacgcaccta gccccagtga accaagcatg    240

cgcgagtgga tacattggat cttagttgac atacctggag gaacaaaccc atttcgcgga    300

aaagagattg tttcatatgt gggaccaaga ccacctattg gaatacatcg ctatatcttt    360

gtgttgtttc aacagaaagg acctttaggt cttgtggagc aaccaccaac tcgagcaagc    420

ttcaacactc gttattttgc caggcaattg gacttgggac ttccagtggc cactgtctac    480

ttcaactctc aaaaagaacc tgctgttaag aggcgctgaa tctagctata ttgtaaccat    540

cagtgtctct cttgagatat gcatggttgg aatatacttt taagatatca gaactatata    600

aaatctatga ctagtgcgta aataatgcag ggagagggtg tgtgtaaagt aatatagttg    660

tccaagacat gagtggtgcc gaccatttcc ccggctttga taactttttt tctctatata    720

tatacctctc tttcactcta tcaaatatat aaagttaatc tttattaaaa aaaaaaaaaa    780

aaaaaaaaaa aaaaaaaaaa aaaaaaaaaa aaaaaaaaaa aaaaaaaaaa aaaaaaaaaa    840

aaaaaaaaaa                                                           850
```

<210> SEQ ID NO 36
<211> LENGTH: 172
<212> TYPE: PRT
<213> ORGANISM: Glycine max

<400> SEQUENCE: 36

```
Met Ala Ala Ser Val Asp Pro Leu Val Val Gly Arg Val Ile Gly Asp
 1               5                  10                  15

Val Val Asp Met Phe Ile Pro Ser Val Asn Met Ser Val Tyr Phe Gly
            20                  25                  30

Ser Lys His Val Thr Asn Gly Cys Asp Ile Lys Pro Ser Ile Ala Ile
        35                  40                  45

Ser Pro Pro Lys Leu Thr Leu Thr Gly Asn Met Asp Asn Leu Tyr Thr
    50                  55                  60

Leu Val Met Thr Asp Pro Asp Ala Pro Ser Pro Ser Glu Pro Ser Met
65                  70                  75                  80

Arg Glu Trp Ile His Trp Ile Leu Val Asp Ile Pro Gly Gly Thr Asn
                85                  90                  95

Pro Phe Arg Gly Lys Glu Ile Val Ser Tyr Val Gly Pro Arg Pro Pro
            100                 105                 110

Ile Gly Ile His Arg Tyr Ile Phe Val Leu Phe Gln Gln Lys Gly Pro
        115                 120                 125

Leu Gly Leu Val Glu Gln Pro Pro Thr Arg Ala Ser Phe Asn Thr Arg
    130                 135                 140

Tyr Phe Ala Arg Gln Leu Asp Leu Gly Leu Pro Val Ala Thr Val Tyr
145                 150                 155                 160

Phe Asn Ser Gln Lys Glu Pro Ala Val Lys Arg Arg
                165                 170
```

<210> SEQ ID NO 37
<211> LENGTH: 969
<212> TYPE: DNA
<213> ORGANISM: Glycine max -continued

<400> SEQUENCE: 37

```
gcacgagcat aacaattgta ttcctccctt ccttagctcc actacctctt ctctcttcct     60
ccttgttcct tcctcttaca atggcaagaa tgcctttaga gcctctaata gtggggagag    120
tcataggaga agttcttgat tcttttacca caagcacaaa aatgattgtg agttacaaca    180
agaatcaagt ctacaatggc catgaactct tcccttccac tgtcaacacc aagcccaagg    240
ttgagattga gggtggtgat atgaggtcct tctttacact gatcatgact gaccctgatg    300
ttcctggccc tagtgaccct tatctgagag agcacttgca ctggatagtg acagatattc    360
caggcacaac agatgccaca tttgggaaag agttggtgag ctatgagatc ccaaagccta    420
atattgggat ccataggttt gtgtttgtcc tgttcaagca aaagcgtaga cagtgtgtta    480
ctccacccac ttcaagggac cacttcaaca cacgcaaatt cgcagcagag aacgaccttg    540
ccctccctgt ggctgctgtc tacttcaatg cacagaggga aacggctgca agaagacgct    600
agctatagct gctgattttg ccactgcttc aaccaaacta gtattgtatt gtattgaata    660
aagcgataaa aaaaggtaca agtacaagga gtttcagtag tggaattaag ttgatcctca    720
catgtggctt caaataactt gcaggaaggg aagataatta atcattttct agtttgaccc    780
gtgtgtatgc tacgttttat tttactttcc atctgttgtg taaacattat actactacgt    840
gtattattat tacctcgtgg gactactatg aggtgtgatc ttatatatag aaataagagg    900
tttggtacgc aaaaaaaaaa aaaaaaaaaa aaaaaaaaaa aaaaaaaaaa aaaaaaaaaa    960
aaaaaaaaa                                                            969
```

<210> SEQ ID NO 38
<211> LENGTH: 173
<212> TYPE: PRT
<213> ORGANISM: Glycine max

<400> SEQUENCE: 38

```
Met Ala Arg Met Pro Leu Glu Pro Leu Ile Val Gly Arg Val Ile Gly
 1               5                  10                  15

Glu Val Leu Asp Ser Phe Thr Thr Ser Thr Lys Met Ile Val Ser Tyr
            20                  25                  30

Asn Lys Asn Gln Val Tyr Asn Gly His Glu Leu Phe Pro Ser Thr Val
        35                  40                  45

Asn Thr Lys Pro Lys Val Glu Ile Glu Gly Gly Asp Met Arg Ser Phe
    50                  55                  60

Phe Thr Leu Ile Met Thr Asp Pro Asp Val Pro Gly Pro Ser Asp Pro
65                  70                  75                  80

Tyr Leu Arg Glu His Leu His Trp Ile Val Thr Asp Ile Pro Gly Thr
                85                  90                  95

Thr Asp Ala Thr Phe Gly Lys Glu Leu Val Ser Tyr Glu Ile Pro Lys
            100                 105                 110

Pro Asn Ile Gly Ile His Arg Phe Val Phe Val Leu Phe Lys Gln Lys
        115                 120                 125

Arg Arg Gln Cys Val Thr Pro Pro Thr Ser Arg Asp His Phe Asn Thr
    130                 135                 140

Arg Lys Phe Ala Ala Glu Asn Asp Leu Ala Leu Pro Val Ala Ala Val
145                 150                 155                 160

Tyr Phe Asn Ala Gln Arg Glu Thr Ala Ala Arg Arg Arg
                165                 170
```

<210> SEQ ID NO 39

```
<211> LENGTH: 836
<212> TYPE: DNA
<213> ORGANISM: Glycine max
<220> FEATURE:
<221> NAME/KEY: misc_feature
<222> LOCATION: 622
<223> OTHER INFORMATION: n = A,T,C or G

<400> SEQUENCE: 39

gttttagagc atattttctt catttttctt gcattccttc tctttgcaat tgatgtctag     60

gctaatggaa caaccacttg ttgtgggaag agtgatagga gaagtggttg acattttcag    120

cccaagtgta agaatgaatg ttacatattc cactaagcaa gttgctaatg gtcatgagtt    180

aatgccttct actattatgg ccaagccacg cgttgagatt ggtggtgatg acatgaggac    240

tgcttatacc ttgatcatga cagacccaga tgctccaagt cctagtgatc cacatctgag    300

ggaacatctc cactggacgg ttacagatat ccctggcacc acagatgtct cttttggtaa    360

agagatagtg ggctatgaga gtccaaaacc agtaatagga atccacaggt atgtgttcat    420

tttgttcaag cagagaggaa gacagacagt caggcctcct tcttcaagag accatttcaa    480

cacaaggagg ttctcagaag agaatggcct tggcctacca gttgctgtag tttacttcaa    540

tgctcaaaga gagactgccg caagaaggag gtgattcctg aagaagaaga agaagaagaa    600

gaaaggttgc agcagtaaat anaattaatt ttgtttcaac cttaatcatc tcataatgag    660

atttgtttcc tttggttttc ttaggggttg gcatggttga gtaaggaaga taggtgtgtt    720

gatgaatctc tcacacatca atgtttcttg tccatttctt tgggtcacaa cgaggaactg    780

taggtagtgt gtcaacagag tgtatctgat gacttaacgt cactggaaag gtgagg        836


<210> SEQ ID NO 40
<211> LENGTH: 173
<212> TYPE: PRT
<213> ORGANISM: Glycine max

<400> SEQUENCE: 40

Met Ser Arg Leu Met Glu Gln Pro Leu Val Val Gly Arg Val Ile Gly
 1               5                  10                  15

Glu Val Val Asp Ile Phe Ser Pro Ser Val Arg Met Asn Val Thr Tyr
            20                  25                  30

Ser Thr Lys Gln Val Ala Asn Gly His Glu Leu Met Pro Ser Thr Ile
        35                  40                  45

Met Ala Lys Pro Arg Val Glu Ile Gly Gly Asp Asp Met Arg Thr Ala
    50                  55                  60

Tyr Thr Leu Ile Met Thr Asp Pro Asp Ala Pro Ser Pro Ser Asp Pro
65                  70                  75                  80

His Leu Arg Glu His Leu His Trp Thr Val Thr Asp Ile Pro Gly Thr
                85                  90                  95

Thr Asp Val Ser Phe Gly Lys Glu Ile Val Gly Tyr Glu Ser Pro Lys
            100                 105                 110

Pro Val Ile Gly Ile His Arg Tyr Val Phe Ile Leu Phe Lys Gln Arg
        115                 120                 125

Gly Arg Gln Thr Val Arg Pro Pro Ser Ser Arg Asp His Phe Asn Thr
    130                 135                 140

Arg Arg Phe Ser Glu Glu Asn Gly Leu Gly Leu Pro Val Ala Val Val
145                 150                 155                 160

Tyr Phe Asn Ala Gln Arg Glu Thr Ala Ala Arg Arg Arg
                165                 170
```

-continued

<210> SEQ ID NO 41
<211> LENGTH: 893
<212> TYPE: DNA
<213> ORGANISM: Triticum aestivum

<400> SEQUENCE: 41

```
ttcggcacga ggggagatcc agctagctag ctggctagtt ttgctgttgc tgctcgacct     60

catcgccatc ctccggctat ggcagcccat gtggatcccc ttgtggttgg gagggtgatc    120

ggtgacgtgg tggacatgtt cgtgcccacc atgccggtga ccgtgcgctt cgggacgaag    180

gacctgacga acggctgcga gatcaagccg tccatcgccg acgcggcgcc ctcgatccag    240

atagccggcc gggccggcga tctcttcacc ctggttatga ctgatccgga cgcaccgagc    300

cccagcgagc caaccatgaa ggagtggctt cactggctgg tggttaacat acctggtgga    360

tcagatcctt ctcaagggga ggaggtggtg ccctacatgg gtccgaagcc gccgttgggc    420

atccaccgct acgtgctggt gctgttccag cagaaggcgc gtgtgctggc gccggctccc    480

ggcggcgaca cagcagcgtc ggccatgcgc gcgcggttca gcacccgtgc cttcgcagag    540

cgccatgacc tggggctccc cgtcgccgcc atgtacttca acgcgcagaa ggagccggcc    600

aaccgccgcc gccgctacta gctcgtcgcc gccggccgat caaacccgct gctgcctgct    660

ggtgctgcct gctggtccgt ctgtgtgtgc gtgcatgcgc gcgggcccaa taaattaacc    720

atatcgatct tgtcgttctc atgaacaatc tgggcttgta ttgtgtggta ctctttgttt    780

gtttttttctt gcgggtgcgt gtggtactct ttggaccata tacatattta ccgctttctc    840

tcttcgttgt attcattgat tatgtgtgag atccaaaaaa aaaaaaaaaa aac           893
```

<210> SEQ ID NO 42
<211> LENGTH: 180
<212> TYPE: PRT
<213> ORGANISM: Triticum aestivum

<400> SEQUENCE: 42

```
Met Ala Ala His Val Asp Pro Leu Val Val Gly Arg Val Ile Gly Asp
1               5                   10                  15

Val Val Asp Met Phe Val Pro Thr Met Pro Val Thr Val Arg Phe Gly
            20                  25                  30

Thr Lys Asp Leu Thr Asn Gly Cys Glu Ile Lys Pro Ser Ile Ala Asp
        35                  40                  45

Ala Ala Pro Ser Ile Gln Ile Ala Gly Arg Ala Gly Asp Leu Phe Thr
    50                  55                  60

Leu Val Met Thr Asp Pro Asp Ala Pro Ser Pro Ser Glu Pro Thr Met
65                  70                  75                  80

Lys Glu Trp Leu His Trp Leu Val Val Asn Ile Pro Gly Gly Ser Asp
                85                  90                  95

Pro Ser Gln Gly Glu Glu Val Val Pro Tyr Met Gly Pro Lys Pro Pro
            100                 105                 110

Leu Gly Ile His Arg Tyr Val Leu Val Leu Phe Gln Gln Lys Ala Arg
        115                 120                 125

Val Leu Ala Pro Ala Pro Gly Gly Asp Thr Ala Ala Ser Ala Met Arg
    130                 135                 140

Ala Arg Phe Ser Thr Arg Ala Phe Ala Glu Arg His Asp Leu Gly Leu
145                 150                 155                 160

Pro Val Ala Ala Met Tyr Phe Asn Ala Gln Lys Glu Pro Ala Asn Arg
                165                 170                 175
```

-continued

```
Arg Arg Arg Tyr
            180


<210> SEQ ID NO 43
<211> LENGTH: 886
<212> TYPE: DNA
<213> ORGANISM: Triticum aestivum

<400> SEQUENCE: 43

gcacgaggcc gccttcatta acatatcgcc acttgcgccg gcggccggcg gagaagggcg      60

ccagtggtga caggaggaag aagatggtgg ggagcggcat gcatgcccag cgcggggacc     120

cgctggtggt ggggcgcgtg atcggcgacg tggtggaccc gttcgtgcgg cgggtggcgc     180

tgcgggtcgg ctacgcgtcc agggacgtgg ccaacggctg cgagctgagg ccgtccgcca     240

tcgccgaccc gccgcgcgtc gaggtcggcg gcccggacat gcgcaccttc tacacgctgg     300

tgatggtgga tccggatgct ccaagtccca gcgatcccag ccttagggag tacttgcact     360

ggctggtcac cgacatcccg gcgacgacag gagtgtcttt tgggaccgag gtggtgtgct     420

acgagggccc gcggccggtg ctcgggatcc accggctggt gttcctgctc ttccagcagc     480

tgggccgcca gacggtgtac gccccggggt ggcggcagaa cttcagcacc cgcgacttcg     540

ccgagctcta caacctcggc ctgcccgtcg ccgccgtcta cttcaactgc cagagggaga     600

ccggaaccgg cgggagaagg atgtgatgat caactccttg tataatacca gtacttaagt     660

agtataagtg acgacacaag atgatgatga tgatgaggtc gtatgggtgg tggtttatac     720

agggcgaaat ggagaaagaa ttgtaatgtt gaagaaataa taactatgcg tgcgactttt     780

ttgatccgat gccggtgcga tactacaaag attaaaaaga tgttaggatc caaaaaaaaa     840

aaaaaaaaaa aaaaaaaaaa aaaaaaaaaa aaaaaaaaaa aaaaaa                    886


<210> SEQ ID NO 44
<211> LENGTH: 180
<212> TYPE: PRT
<213> ORGANISM: Triticum aestivum

<400> SEQUENCE: 44

Met Val Gly Ser Gly Met His Ala Gln Arg Gly Asp Pro Leu Val Val
 1               5                  10                  15

Gly Arg Val Ile Gly Asp Val Val Asp Pro Phe Val Arg Arg Val Ala
            20                  25                  30

Leu Arg Val Gly Tyr Ala Ser Arg Asp Val Ala Asn Gly Cys Glu Leu
        35                  40                  45

Arg Pro Ser Ala Ile Ala Asp Pro Pro Arg Val Glu Val Gly Gly Pro
    50                  55                  60

Asp Met Arg Thr Phe Tyr Thr Leu Val Met Val Asp Pro Asp Ala Pro
65                  70                  75                  80

Ser Pro Ser Asp Pro Ser Leu Arg Glu Tyr Leu His Trp Leu Val Thr
                85                  90                  95

Asp Ile Pro Ala Thr Thr Gly Val Ser Phe Gly Thr Glu Val Val Cys
            100                 105                 110

Tyr Glu Gly Pro Arg Pro Val Leu Gly Ile His Arg Leu Val Phe Leu
        115                 120                 125

Leu Phe Gln Gln Leu Gly Arg Gln Thr Val Tyr Ala Pro Gly Trp Arg
    130                 135                 140

Gln Asn Phe Ser Thr Arg Asp Phe Ala Glu Leu Tyr Asn Leu Gly Leu
145                 150                 155                 160
```

-continued

```
Pro Val Ala Ala Val Tyr Phe Asn Cys Gln Arg Glu Thr Gly Thr Gly
                165                 170                 175

Gly Arg Arg Met
            180


<210> SEQ ID NO 45
<211> LENGTH: 1257
<212> TYPE: DNA
<213> ORGANISM: Zea mays

<400> SEQUENCE: 45

ctcgctcaga cagctctgct agctgcatcc tcctaactct ccaggtctct ctctcctctc      60

ccaactccca agtcccatcc ggatcgagac gctggaggcg gagcgccccc ccgggacggc     120

ggcggcgacg atggggcgcg gcaagatcga gatcaagcgg atcgagaacg ccaccaaccg     180

ccaggtgacc tactccaagc gccggacggg gatcatgaag aaggcgcgcg agctcaccgt     240

gctctgcgac gcccaggtcg ccatcatcat gttctcctcc accggcaagt accacgagtt     300

ctgcagcccc ggaaccgaca tcaagaccat ctttgaccgg taccagcagg ccatcgggac     360

cagcctatgg atcgagcagt atgagaatat gcagcgcacg ctgagccatc tcaaggacat     420

caatcgtggt ctgcgcacag agattaggca aaggatgggc gaggatctgg acagtctgga     480

cttcgacgag ctgcgcggcc tcgagcaaaa cgtcgacgcg gctctcaagg aggttcgcca     540

taggaagtac catgtgatca gcacgcagac tgatacctac aagaaaaagg tgaagcactc     600

gcacgaggcg tacaagaacc tgcagcagga gctaggcatg cgggaggacc cggcgttcgg     660

gtacgtggac aacacgggcg ccggcgtcgc ctgggacggc gcggcggcgg cgctgggcgg     720

cgccccgccg gacatgtacg ccttccgcgt ggtgcccagc cagcccaacc tgcacggcat     780

ggcctacggc ttccacgacc tccgcctggg ctagcgcatc catcaccatg ctgggtggtg     840

ctgctcgatc ctactgcatg gcaatgcaag ctggttggtt agttcgctca tgcatcgtcc     900

gtcaacaaag caagtaagca atgcaatgca accgaggtac tgtaatagcc aataaaatct     960

actgcatact gcaaacccaa ttactggtag cttagctacc gcgtgtgtac gaatcaaccg    1020

attaattacc gcgcccttag cttgcatgtc gtcgtcgtct gtgcttttgg cgttcgtaga    1080

catgtgtgta ttgtatgcat gggtcctgtt catctgcatc catgcatgtt gtttatgatt    1140

gtaattgttg tgtgaaatgg ctgtactttg ttatgatcac gtgaaattat atctacattc    1200

gtgggaaaaa aaaaaaaaaa aaaaaaaaaa aaaaaaaaaa aaaaaaaaaa aaaaaaa       1257


<210> SEQ ID NO 46
<211> LENGTH: 227
<212> TYPE: PRT
<213> ORGANISM: Zea mays

<400> SEQUENCE: 46

Met Gly Arg Gly Lys Ile Glu Ile Lys Arg Ile Glu Asn Ala Thr Asn
 1               5                  10                  15

Arg Gln Val Thr Tyr Ser Lys Arg Arg Thr Gly Ile Met Lys Lys Ala
            20                  25                  30

Arg Glu Leu Thr Val Leu Cys Asp Ala Gln Val Ala Ile Ile Met Phe
        35                  40                  45

Ser Ser Thr Gly Lys Tyr His Glu Phe Cys Ser Pro Gly Thr Asp Ile
    50                  55                  60

Lys Thr Ile Phe Asp Arg Tyr Gln Gln Ala Ile Gly Thr Ser Leu Trp
65                  70                  75                  80
```

-continued

```
Ile Glu Gln Tyr Glu Asn Met Gln Arg Thr Leu Ser His Leu Lys Asp
                85                  90                  95

Ile Asn Arg Gly Leu Arg Thr Glu Ile Arg Gln Arg Met Gly Glu Asp
            100                 105                 110

Leu Asp Ser Leu Asp Phe Asp Glu Leu Arg Gly Leu Glu Gln Asn Val
        115                 120                 125

Asp Ala Ala Leu Lys Glu Val Arg His Arg Lys Tyr His Val Ile Ser
    130                 135                 140

Thr Gln Thr Asp Thr Tyr Lys Lys Lys Val Lys His Ser His Glu Ala
145                 150                 155                 160

Tyr Lys Asn Leu Gln Gln Glu Leu Gly Met Arg Glu Asp Pro Ala Phe
                165                 170                 175

Gly Tyr Val Asp Asn Thr Gly Ala Gly Val Ala Trp Asp Gly Ala Ala
            180                 185                 190

Ala Ala Leu Gly Gly Ala Pro Pro Asp Met Tyr Ala Phe Arg Val Val
        195                 200                 205

Pro Ser Gln Pro Asn Leu His Gly Met Ala Tyr Gly Phe His Asp Leu
    210                 215                 220

Arg Leu Gly
225
```

<210> SEQ ID NO 47
<211> LENGTH: 1089
<212> TYPE: DNA
<213> ORGANISM: Zea mays

<400> SEQUENCE: 47

```
ccacgcgtcc gaccgcaccg gcaccaccac caaccgagcg gctccaggct cctgctcagg     60

aaggggagaa gaggcgagcc ttccttggga agtcgcagga ggagagaagg ggaacaaaga    120

tggggcgcgg caagatcgag atcaagcgga tcgagaactc caccaaccgc caggtgacct    180

tctccaagcg ccgcaacggg atcctcaaga aggcgcggga gatcagcgtg ctctgcgacg    240

ccgaggtcgg cgtcgtcgtc ttctccagcg ccggcaagct ttacgactac tgctccccga    300

agacatcgct atcaaaaatc ctggagaagt accagaccaa ctctggaaag atactgtggg    360

gtgagaagca caagagcctt agtgcagaga ttgaccgtat aaagaaagag aacgacacca    420

tgcagatcga gctcaggcac ctgaaaggtg aagatctaaa ctcgctgcaa cccaaagacc    480

tgatcatgat cgaggaggca cttgataatg gactgacgaa cctgaatgag aaactgatgg    540

agcactggga aaggcgtgtg acaaacacta agatgatgga agacgagaac aaattgctgg    600

ccttcaaact ccaccagcaa gatatcgcgc tgagcggcag catgagagag cttgagctgg    660

gttaccatcc tgaccgggac ctggcggccc agatgccaat caccttccgc gtgcagccca    720

gccatcccaa cttgcaggag aacaattaga ctgctggatg ccctcgttcc actcgccgag    780

gatttcaccc agccaccacc gctggcttgt atgccctcgt gcgctggcaa ctgtatcttt    840

atctttccgg tatgtttgga tgaacgtata atgtgtgtca gtgtcggtcg catgacgtgc    900

cgatgtcgtg catctctctc tctctctgcc agagcagcgg aactctgcac cgtgagtaac    960

ttaattggta ccgtatgatc tgccggacag tgaatagttt atgtgagtgg gtcaaaccat   1020

aatgtgtagt atttgtgtcg aactgtcaat ggcacgtatt tggattttca ctaaaaaaaa   1080

aaaaaaaag                                                            1089
```

<210> SEQ ID NO 48
<211> LENGTH: 209

-continued

<212> TYPE: PRT
<213> ORGANISM: Zea mays

<400> SEQUENCE: 48

```
Met Gly Arg Gly Lys Ile Glu Ile Lys Arg Ile Glu Asn Ser Thr Asn
 1               5                  10                  15

Arg Gln Val Thr Phe Ser Lys Arg Arg Asn Gly Ile Leu Lys Lys Ala
            20                  25                  30

Arg Glu Ile Ser Val Leu Cys Asp Ala Glu Val Gly Val Val Val Phe
        35                  40                  45

Ser Ser Ala Gly Lys Leu Tyr Asp Tyr Cys Ser Pro Lys Thr Ser Leu
    50                  55                  60

Ser Lys Ile Leu Glu Lys Tyr Gln Thr Asn Ser Gly Lys Ile Leu Trp
65                  70                  75                  80

Gly Glu Lys His Lys Ser Leu Ser Ala Glu Ile Asp Arg Ile Lys Lys
                85                  90                  95

Glu Asn Asp Thr Met Gln Ile Glu Leu Arg His Leu Lys Gly Glu Asp
            100                 105                 110

Leu Asn Ser Leu Gln Pro Lys Asp Leu Ile Met Ile Glu Glu Ala Leu
        115                 120                 125

Asp Asn Gly Leu Thr Asn Leu Asn Glu Lys Leu Met Glu His Trp Glu
    130                 135                 140

Arg Arg Val Thr Asn Thr Lys Met Met Glu Asp Glu Asn Lys Leu Leu
145                 150                 155                 160

Ala Phe Lys Leu His Gln Gln Asp Ile Ala Leu Ser Gly Ser Met Arg
                165                 170                 175

Glu Leu Glu Leu Gly Tyr His Pro Asp Arg Asp Leu Ala Ala Gln Met
            180                 185                 190

Pro Ile Thr Phe Arg Val Gln Pro Ser His Pro Asn Leu Gln Glu Asn
        195                 200                 205

Asn
```

<210> SEQ ID NO 49
<211> LENGTH: 926
<212> TYPE: DNA
<213> ORGANISM: Glycine max

<400> SEQUENCE: 49

```
gcacgaggct atggctagag gaaagatcca gatcaagagg atagagaaca acaccaaccg      60

ccaggtcact tactctaaac gacggaatgg ccttttcaag aaggccaacg agcttaccgt     120

tctctgcgat gccaaggttt ctattattat gttctccagc actggaaaac tccaccagta     180

catcagcccc tccacctcaa caaagcagtt cttcgatcaa taccagatga ctctgggagt     240

tgatctctgg aactctcatt acgagaatat gcaagagaac ttgaagaaac tgaaagaggt     300

gaataggaat cttcgtaagg agattaggca gagaatggga gattgtctga acgagctggg     360

catggaagat ctcaagctcc ttgaggaaga aatggacaag gccgccaagg ttgttcgtga     420

gcgtaagtat aaggtgataa caaatcagat tgacacccag aggaaaaagt ttaataacga     480

gaaagaagtg cacaacaggc tcctgcatga cttggatgca aaagcagaag atccacgttt     540

tgcattgata gataatggag gggagtatga gtctgtgatc ggattctcaa atttaggtcc     600

acgcatgttc gcattgagca tacaaccaag ccatcctagt gcccatagcg gaggagcagg     660

ctctgatctt accacttacc ctttactttt ctagtacgca attgcttaag ctctctccat     720

cagaaatacc atattcactc aaatttcaat aagaatgact tgttgcagtt tgtacttaac     780
```

-continued

```
cacaaaacaa tctcacgaat cttctccgtg gaacgcatgt gtgaattatt caattgcaac    840

tactgttatc tgtattttct ttttgcctaa tcatatacca taaacatgaa gttgtgcttc    900

cttttaaaaa aaaaaaaaaa aaaaaa                                         926


<210> SEQ ID NO 50
<211> LENGTH: 227
<212> TYPE: PRT
<213> ORGANISM: Glycine max

<400> SEQUENCE: 50

Met Ala Arg Gly Lys Ile Gln Ile Lys Arg Ile Glu Asn Asn Thr Asn
 1               5                  10                  15

Arg Gln Val Thr Tyr Ser Lys Arg Arg Asn Gly Leu Phe Lys Lys Ala
            20                  25                  30

Asn Glu Leu Thr Val Leu Cys Asp Ala Lys Val Ser Ile Ile Met Phe
        35                  40                  45

Ser Ser Thr Gly Lys Leu His Gln Tyr Ile Ser Pro Ser Thr Ser Thr
    50                  55                  60

Lys Gln Phe Phe Asp Gln Tyr Gln Met Thr Leu Gly Val Asp Leu Trp
65                  70                  75                  80

Asn Ser His Tyr Glu Asn Met Gln Glu Asn Leu Lys Lys Leu Lys Glu
                85                  90                  95

Val Asn Arg Asn Leu Arg Lys Glu Ile Arg Gln Arg Met Gly Asp Cys
            100                 105                 110

Leu Asn Glu Leu Gly Met Glu Asp Leu Lys Leu Leu Glu Glu Glu Met
        115                 120                 125

Asp Lys Ala Ala Lys Val Val Arg Glu Arg Lys Tyr Lys Val Ile Thr
    130                 135                 140

Asn Gln Ile Asp Thr Gln Arg Lys Lys Phe Asn Asn Glu Lys Glu Val
145                 150                 155                 160

His Asn Arg Leu Leu His Asp Leu Asp Ala Lys Ala Glu Asp Pro Arg
                165                 170                 175

Phe Ala Leu Ile Asp Asn Gly Gly Glu Tyr Glu Ser Val Ile Gly Phe
            180                 185                 190

Ser Asn Leu Gly Pro Arg Met Phe Ala Leu Ser Ile Gln Pro Ser His
        195                 200                 205

Pro Ser Ala His Ser Gly Gly Ala Gly Ser Asp Leu Thr Thr Tyr Pro
    210                 215                 220

Leu Leu Phe
225


<210> SEQ ID NO 51
<211> LENGTH: 173
<212> TYPE: PRT
<213> ORGANISM: Oryza sativa

<400> SEQUENCE: 51

Met Ser Arg Ser Val Glu Pro Leu Val Val Gly Arg Val Ile Gly Glu
 1               5                  10                  15

Val Leu Asp Thr Phe Asn Pro Cys Met Lys Met Ile Val Thr Tyr Asn
            20                  25                  30

Ser Asn Lys Leu Val Phe Asn Gly His Glu Leu Tyr Pro Ser Ala Val
        35                  40                  45

Val Ser Lys Pro Arg Val Glu Val Gln Gly Gly Asp Leu Arg Ser Phe
    50                  55                  60
```

```
Phe Thr Leu Val Met Thr Asp Pro Asp Val Pro Gly Pro Ser Asp Pro
65                  70                  75                  80

Tyr Leu Arg Glu His Leu His Trp Ile Val Thr Asp Ile Pro Gly Thr
                85                  90                  95

Thr Asp Ala Ser Phe Gly Arg Glu Val Ile Ser Tyr Glu Ser Pro Lys
            100                 105                 110

Pro Asn Ile Gly Ile His Arg Phe Ile Phe Val Leu Phe Lys Gln Lys
        115                 120                 125

Arg Arg Gln Thr Val Ile Val Pro Ser Phe Arg Asp His Phe Asn Thr
    130                 135                 140

Arg Arg Phe Ala Glu Glu Asn Asp Leu Gly Leu Pro Val Ala Ala Val
145                 150                 155                 160

Tyr Phe Asn Ala Gln Arg Glu Thr Ala Ala Arg Arg Arg
                165                 170


<210> SEQ ID NO 52
<211> LENGTH: 224
<212> TYPE: PRT
<213> ORGANISM: Oryza sativa

<400> SEQUENCE: 52

Met Gly Arg Gly Lys Ile Glu Ile Lys Arg Ile Glu Asn Ala Thr Asn
 1               5                  10                  15

Arg Gln Val Thr Tyr Ser Lys Arg Arg Thr Gly Ile Met Lys Lys Ala
            20                  25                  30

Arg Glu Leu Thr Val Leu Cys Asp Ala Gln Val Ala Ile Ile Met Phe
        35                  40                  45

Ser Ser Thr Gly Lys Tyr His Glu Phe Cys Ser Pro Ser Thr Asp Ile
    50                  55                  60

Lys Gly Ile Phe Asp Arg Tyr Gln Gln Ala Ile Gly Thr Ser Leu Trp
65                  70                  75                  80

Ile Glu Gln Tyr Glu Asn Met Gln Arg Thr Leu Ser His Leu Lys Asp
                85                  90                  95

Ile Asn Arg Asn Leu Arg Thr Glu Ile Arg Gln Arg Met Gly Glu Asp
            100                 105                 110

Leu Asp Gly Leu Glu Phe Asp Glu Leu Arg Gly Leu Glu Gln Asn Val
        115                 120                 125

Asp Ala Ala Leu Lys Glu Val Arg His Arg Lys Tyr His Val Ile Thr
    130                 135                 140

Thr Gln Thr Glu Thr Tyr Lys Lys Lys Val Lys His Ser Tyr Glu Ala
145                 150                 155                 160

Tyr Glu Thr Leu Gln Gln Glu Leu Gly Leu Arg Glu Glu Pro Ala Phe
                165                 170                 175

Gly Phe Val Asp Asn Thr Gly Gly Gly Trp Asp Gly Gly Ala Gly Ala
            180                 185                 190

Gly Ala Ala Ala Asp Met Phe Ala Phe Arg Val Val Pro Ser Gln Pro
        195                 200                 205

Asn Leu His Gly Met Ala Tyr Gly Gly Asn His Asp Leu Arg Leu Gly
    210                 215                 220


<210> SEQ ID NO 53
<211> LENGTH: 613
<212> TYPE: DNA
<213> ORGANISM: Zea mays
<220> FEATURE:
<221> NAME/KEY: misc_feature
```

<222> LOCATION: 613
<223> OTHER INFORMATION: n = A,T,C or G

<400> SEQUENCE: 53

```
tacttctcgg cgtcggcgct gctccgagtg atgtacggcg ggcgcgagat gacctgcggg     60

tcggagctca ggccgtcgca ggtggcgagc gagccgacgg tgcacatcac ggggggccgc    120

gacgggaggc cggtgctcta cacactggtg atgctggacc ccgatgcgcc cagcccaagc    180

aacccctcca agcgggagta tctccattgg ttggtgactg acataccaga aggagctggt    240

gccaatcatg ggaacgaggt ggtggcgtac gagagccccc ggccatcggc ggggatccac    300

cgattcgtgt tcatcgtgtt ccggcaggcg gtccggcagg cgatctacgc gcctgggtgg    360

cgcgccaact tcaacaccag ggacttcgcc gcctgctaca gcctcggacc gcctgtcgcc    420

gccacctact tcaactgcca gagggagggc ggctgcggtg gtcggaggta caggtgatga    480

atcgagagag agcatgcatc ccaacaaggc ggtgatgaca cgtgacccat cctatgacaa    540

gttatatata ttagcacata ccacaaaaat aaacaataca tatatatatg tctccatctc    600

tatctgcaat atn                                                       613
```

<210> SEQ ID NO 54
<211> LENGTH: 158
<212> TYPE: PRT
<213> ORGANISM: Zea mays

<400> SEQUENCE: 54

```
Tyr Phe Ser Ala Ser Ala Leu Leu Arg Val Met Tyr Gly Gly Arg Glu
1               5                   10                  15

Met Thr Cys Gly Ser Glu Leu Arg Pro Ser Gln Val Ala Ser Glu Pro
            20                  25                  30

Thr Val His Ile Thr Gly Gly Arg Asp Gly Arg Pro Val Leu Tyr Thr
        35                  40                  45

Leu Val Met Leu Asp Pro Asp Ala Pro Ser Pro Ser Asn Pro Ser Lys
    50                  55                  60

Arg Glu Tyr Leu His Trp Leu Val Thr Asp Ile Pro Glu Gly Ala Gly
65                  70                  75                  80

Ala Asn His Gly Asn Glu Val Val Ala Tyr Glu Ser Pro Arg Pro Ser
                85                  90                  95

Ala Gly Ile His Arg Phe Val Phe Ile Val Phe Arg Gln Ala Val Arg
            100                 105                 110

Gln Ala Ile Tyr Ala Pro Gly Trp Arg Ala Asn Phe Asn Thr Arg Asp
        115                 120                 125

Phe Ala Ala Cys Tyr Ser Leu Gly Pro Pro Val Ala Ala Thr Tyr Phe
    130                 135                 140

Asn Cys Gln Arg Glu Gly Gly Cys Gly Gly Arg Arg Tyr Arg
145                 150                 155
```

<210> SEQ ID NO 55
<211> LENGTH: 945
<212> TYPE: DNA
<213> ORGANISM: Oryza sativa

<400> SEQUENCE: 55

```
gcacgaggga gagatcgatg gcccgtttcg tggatccgct ggtggtggga cgggtgatcg     60

gggaggtggt ggatttgttc gttccatcca tctccatgac cgccgcctac ggcgacaggg    120

acatcagcaa cggctgcctc gtccgcccat ccgccgccga ctaccctccc ctcgtccgca    180
```

-continued

```
tctccggccg ccgcaacgac ctctacaccc tgatcatgac ggacccggac gcacctagcc    240

ctagcgaccc atccatgagg gagtttctcc actggatcgt ggttaacata ccggggggaa    300

cagatgcatc taaaggtgag gagatggtgg agtacatggg gccacggccg acggtgggga    360

tacacaggta cgtgctggtg ctgtacgagc agaaggcgcg cttcgtggac ggcgcgctga    420

tgccgccggc ggacaggccc aacttcaaca caagagcatt cgcggcgtac catcagctcg    480

gcctccccac cgccgtcgtc cacttcaact cccagaggga gcccgccaac cgccgccgct    540

aatagtaata gcctactatc tctatctatc tatccataat gaagaaagca agcacgcctg    600

cggatgcggc cggccggccc tactatatta ttacaataat atagtttttg aataattaag    660

ctagctagct ctcaactcaa gtatacttac tggaactcga ctgcgttgcg tacgcatgtc    720

ctcatcatac gtacgaacgt gcgtgtccac gtactgtgta ctagctagcg agtactctct    780

ccatatatat cttcctccac cgtcgtgtgg tacgttttaa caacgtacat gcatgcatgg    840

ataatgcagg ctctatatat atatatataa tactactgta ctgtactgta tgctttaatt    900

aattttgtgg tttgctctca aaaaaaaaaa aaaaaaaaaa aaaaa                    945
```

```
<210> SEQ ID NO 56
<211> LENGTH: 174
<212> TYPE: PRT
<213> ORGANISM: Oryza sativa

<400> SEQUENCE: 56

Met Ala Arg Phe Val Asp Pro Leu Val Val Gly Arg Val Ile Gly Glu
 1               5                  10                  15

Val Val Asp Leu Phe Val Pro Ser Ile Ser Met Thr Ala Ala Tyr Gly
            20                  25                  30

Asp Arg Asp Ile Ser Asn Gly Cys Leu Val Arg Pro Ser Ala Ala Asp
        35                  40                  45

Tyr Pro Pro Leu Val Arg Ile Ser Gly Arg Arg Asn Asp Leu Tyr Thr
    50                  55                  60

Leu Ile Met Thr Asp Pro Asp Ala Pro Ser Pro Ser Asp Pro Ser Met
65                  70                  75                  80

Arg Glu Phe Leu His Trp Ile Val Val Asn Ile Pro Gly Gly Thr Asp
                85                  90                  95

Ala Ser Lys Gly Glu Glu Met Val Glu Tyr Met Gly Pro Arg Pro Thr
            100                 105                 110

Val Gly Ile His Arg Tyr Val Leu Val Leu Tyr Glu Gln Lys Ala Arg
        115                 120                 125

Phe Val Asp Gly Ala Leu Met Pro Pro Ala Asp Arg Pro Asn Phe Asn
    130                 135                 140

Thr Arg Ala Phe Ala Ala Tyr His Gln Leu Gly Leu Pro Thr Ala Val
145                 150                 155                 160

Val His Phe Asn Ser Gln Arg Glu Pro Ala Asn Arg Arg Arg
                165                 170


<210> SEQ ID NO 57
<211> LENGTH: 639
<212> TYPE: DNA
<213> ORGANISM: Oryza sativa

<400> SEQUENCE: 57

gcacgagctt acacctaatc ccagcaaccc aaccttgagg gaatacctgc actggatggt     60

gactgatatc ccatcatcga cggacgatag ctttgggcgg gagatcgtaa catacgaaag    120
```

-continued

```
cccaagcccc accatgggca tccaccgcat cgtgatggtg ttgtatcagc agcttgggcg    180

cggcacggtg ttcgcgccgc aggtgcgtca gaacttcaac ctgcgcagct tcgcgcgccg    240

tttcaacctc ggcaagccgg tggccgccat gtacttcaac tgccagcgcc cgacaggcac    300

aggtgggagg aggccaacct gatctgatca atatcgatcg atcttcgatc ttctagctct    360

tgtacatgtt gagtgttgac caatataatg gccactcatg catatatata tatatgcagt    420

gtgtctagcc agctgcatgc aactttgtct acgtgcttat ataattaaac aaatgcatat    480

atagccggcc gtatcataaa gttcctagct ataaaagcta tagaataaat gtcgccccac    540

ttggtcagtt ggtgtacatg acggctccta agtgtgctat catgaatatg ctaataatag    600

cagtttagta tatcatcccc gcaaaaaaaa aaaaaaaaa                           639
```

<210> SEQ ID NO 58
<211> LENGTH: 104
<212> TYPE: PRT
<213> ORGANISM: Oryza sativa

<400> SEQUENCE: 58

```
Leu Thr Pro Asn Pro Ser Asn Pro Thr Leu Arg Glu Tyr Leu His Trp
 1               5                  10                  15

Met Val Thr Asp Ile Pro Ser Ser Thr Asp Asp Ser Phe Gly Arg Glu
            20                  25                  30

Ile Val Thr Tyr Glu Ser Pro Ser Pro Thr Met Gly Ile His Arg Ile
        35                  40                  45

Val Met Val Leu Tyr Gln Gln Leu Gly Arg Gly Thr Val Phe Ala Pro
    50                  55                  60

Gln Val Arg Gln Asn Phe Asn Leu Arg Ser Phe Ala Arg Arg Phe Asn
65                  70                  75                  80

Leu Gly Lys Pro Val Ala Ala Met Tyr Phe Asn Cys Gln Arg Pro Thr
                85                  90                  95

Gly Thr Gly Gly Arg Arg Pro Thr
            100
```

<210> SEQ ID NO 59
<211> LENGTH: 1004
<212> TYPE: DNA
<213> ORGANISM: Oryza sativa

<400> SEQUENCE: 59

```
gcacgagctc aagttagctt cttagcacag cctcttcttg ctcaactcct gaagatcatc     60

aatcttcact agccatgtca agggacccac ttgtcgtagg acatgttgtt ggggatatct    120

tagacccatt caacaaatca gcatcactca aggtcctata caacaacaag gaattaacaa    180

atgggtctga gctcaaaccg tcacaggtag caaatgaacc aaggattgaa attgctggcc    240

gcgacataag gaacctttac actctggtga tggtggatcc tgactcgcca agtccaagca    300

acccaacaaa aagagaatac cttcattggt tggtgacaga cattccagaa tcggcaaatg    360

ctagttatgg aaatgaagtt gtcagttatg aaagcccaaa accaactgca gggatacatc    420

gttttgtctt tatattattt cgccaatatg tacaacagac tatttatgca ccaggatgga    480

gaccaaattt caatacaaga gatttttccg cactgtataa tcttggacct cctgtggcag    540

cagtgttctt caattgccag agggagaacg gatgtggagg cagacggtac attagataaa    600

agtcaggatc attcatagcc ctctacaaga agaggtgata ttcatgtgag aagatgaatg    660

gggtcaggca catcgcaacg tgctggtcaa tggtggacct tttaatgtat cttcatttaa    720
```

-continued

```
gaactactac ctttgatacg tatccaggca ctaaacaagg tgctttacga atgaatttag    780

cttcagatct catcttggag aacactttat ctggttcttc aggaacgaaa tcctactgat    840

tctgcaccca acaactgttg tccatgtcat gttcaaaagc gactatcaaa gcaacaaatt    900

gagtgcatca ttgaagaatg caactgataa cacgtcatgt tctttaaaaa agaaagcatc    960

ctaggcttac tgagaacttt gcataaaaaa aaaaaaaaaa aaaa                    1004


<210> SEQ ID NO 60
<211> LENGTH: 174
<212> TYPE: PRT
<213> ORGANISM: Oryza sativa

<400> SEQUENCE: 60

Met Ser Arg Asp Pro Leu Val Val Gly His Val Val Gly Asp Ile Leu
 1               5                  10                  15

Asp Pro Phe Asn Lys Ser Ala Ser Leu Lys Val Leu Tyr Asn Asn Lys
            20                  25                  30

Glu Leu Thr Asn Gly Ser Glu Leu Lys Pro Ser Gln Val Ala Asn Glu
        35                  40                  45

Pro Arg Ile Glu Ile Ala Gly Arg Asp Ile Arg Asn Leu Tyr Thr Leu
    50                  55                  60

Val Met Val Asp Pro Asp Ser Pro Ser Pro Ser Asn Pro Thr Lys Arg
65                  70                  75                  80

Glu Tyr Leu His Trp Leu Val Thr Asp Ile Pro Glu Ser Ala Asn Ala
                85                  90                  95

Ser Tyr Gly Asn Glu Val Val Ser Tyr Glu Ser Pro Lys Pro Thr Ala
            100                 105                 110

Gly Ile His Arg Phe Val Phe Ile Leu Phe Arg Gln Tyr Val Gln Gln
        115                 120                 125

Thr Ile Tyr Ala Pro Gly Trp Arg Pro Asn Phe Asn Thr Arg Asp Phe
    130                 135                 140

Ser Ala Leu Tyr Asn Leu Gly Pro Pro Val Ala Ala Val Phe Phe Asn
145                 150                 155                 160

Cys Gln Arg Glu Asn Gly Cys Gly Gly Arg Arg Tyr Ile Arg
                165                 170


<210> SEQ ID NO 61
<211> LENGTH: 175
<212> TYPE: PRT
<213> ORGANISM: Arabidopsis thaliana

<400> SEQUENCE: 61

Met Ser Ile Asn Ile Arg Asp Pro Leu Ile Val Ser Arg Val Val Gly
 1               5                  10                  15

Asp Val Leu Asp Pro Phe Asn Arg Ser Ile Thr Leu Lys Val Thr Tyr
            20                  25                  30

Gly Gln Arg Glu Val Thr Asn Gly Leu Asp Leu Arg Pro Ser Gln Val
        35                  40                  45

Gln Asn Lys Pro Arg Val Glu Ile Gly Gly Glu Asp Leu Arg Asn Phe
    50                  55                  60

Tyr Thr Leu Val Met Val Asp Pro Asp Val Pro Ser Pro Ser Asn Pro
65                  70                  75                  80

His Leu Arg Glu Tyr Leu His Trp Leu Val Thr Asp Ile Pro Ala Thr
                85                  90                  95

Thr Gly Thr Thr Phe Gly Asn Glu Ile Val Cys Tyr Glu Asn Pro Ser
            100                 105                 110
```

-continued

```
Pro Thr Ala Gly Ile His Arg Val Val Phe Ile Leu Phe Arg Gln Leu
        115                 120                 125

Gly Arg Gln Thr Val Tyr Ala Pro Gly Trp Arg Gln Asn Phe Asn Thr
    130                 135                 140

Arg Glu Phe Ala Glu Ile Tyr Asn Leu Gly Leu Pro Val Ala Ala Val
145                 150                 155                 160

Phe Tyr Asn Cys Gln Arg Glu Ser Gly Cys Gly Gly Arg Arg Leu
                165                 170                 175


<210> SEQ ID NO 62
<211> LENGTH: 179
<212> TYPE: PRT
<213> ORGANISM: Oryza sativa

<400> SEQUENCE: 62

Met Ala Gly Ser Gly Arg Asp Arg Asp Pro Leu Val Val Gly Arg Val
 1               5                  10                  15

Val Gly Asp Val Leu Asp Ala Phe Val Arg Ser Thr Asn Leu Lys Val
            20                  25                  30

Thr Tyr Gly Ser Lys Thr Val Ser Asn Gly Cys Glu Leu Lys Pro Ser
        35                  40                  45

Met Val Thr His Gln Pro Arg Val Glu Val Gly Gly Asn Asp Met Arg
    50                  55                  60

Thr Phe Tyr Thr Leu Val Met Val Asp Pro Asp Ala Pro Ser Pro Ser
65                  70                  75                  80

Asp Pro Asn Leu Arg Glu Tyr Leu His Trp Leu Val Thr Asp Ile Pro
                85                  90                  95

Gly Thr Thr Ala Ala Ser Phe Gly Gln Glu Val Met Cys Tyr Glu Ser
            100                 105                 110

Pro Arg Pro Thr Met Gly Ile His Arg Leu Val Phe Val Leu Phe Gln
        115                 120                 125

Gln Leu Gly Arg Gln Thr Val Tyr Ala Pro Gly Trp Arg Gln Asn Phe
    130                 135                 140

Asn Thr Lys Asp Phe Ala Glu Leu Tyr Asn Leu Gly Ser Pro Val Ala
145                 150                 155                 160

Ala Val Tyr Phe Asn Cys Gln Arg Glu Ala Gly Ser Gly Gly Arg Arg
                165                 170                 175

Val Tyr Pro


<210> SEQ ID NO 63
<211> LENGTH: 13400
<212> TYPE: DNA
<213> ORGANISM: Zea mays

<400> SEQUENCE: 63

atattatttt cactcgcgag ctgctaaaga aaagcgccag tgataataat gtttccacag      60

gcgttttctt aagcagcccg ccagtgaaaa ttcagttttg tttgaaaatt tgaaaaaagg     120

caggaaactt atactggcgg gcagctaaag aaaaccgcca gtgataataa tctttccact     180

ggcggtgtga taacgaatgc ggacacaata tttattctta ggcggggctg cttaaaacac     240

cgccagtgat aataatattt ccacatgcgg tttcttaagc aaaccgccag tgctaatgat     300

atttacactg gcgggctgct aaataaaacc gtcagtgcta aagatattta cactgacggc     360

tgacgaacaa ccgcctgtga aaaagcccga tttctactgg cacctagcac tggcggcact     420

gaaaaacgcc agtgcaaata gctttaggac cgccactata gagcttctgt gtactagtgc     480
```

```
tgccttattc cctccaccac ccggccttgt cacgctcgtt gtcgagtact agaaaatctt    540
gtgtgttgtt gacgttattt ggctcattct tgagcttttc tgaacgaacc agtggactgc    600
tcgtccacgg ctcgatcggc gtaattagag atgttgtaac gggtcacgtc tacaacctag    660
tctaattagg ataaaagtgc acactgaaca catgattagc gcatgtcacc caataataac    720
ctcgatcgtt cgccctccac cggaatcgaa gccaggacag gacaggcacc gcaggagatc    780
gacacgtcaa cccatcttgt tttttctacg accgctatta ttatttacca cttgcttact    840
tagtacttac tgtgcggtgc ggggtaattg gtaaacgggt gtcgacgtcc cgggcgcgta    900
cgtcgtgttg cggttactgt taccgcgccg tggtcgtggt gggccagcaa agtctggcgg    960
gcggccaatg ggaactcgac agagcggggg agacatgacg gggctgatag ctgtacgtcc   1020
tccaatccca tgcacccggc cacccatccg ctccgctgtc tcgtcagccg tcagctacct   1080
ctctagctgc tcgctcctca agcagtcaag cttctcaatg gaacagtatc tatctatccc   1140
tacagtgggc agtggtgcca tacatggcca aaagttttag cactatatga caccaaccag   1200
caagtttaat aatatagctc aggacaggtt ttaggatggt aatatgtcgt atatagttaa   1260
ctaaaaacct actcatataa taactctcca tagagacaaa ttattgtaga aaccgtagcc   1320
ggattaaagc tgcagcaaac cgcaacgaac atggaagctg cctatttttt ctccctccac   1380
ttctcttatt tttatgtcac cataaatctg acgtgatatc tcttatacta ctccgtctat   1440
atcaacttat tatacttgct ctaacaccta gtattgtcgg tgcctatcta taccgtcaaa   1500
aaatttgaaa tagtgtaaag attacaaata taatgtaaaa atatgaatat ttataccaat   1560
atagatcgga tctatcatat ttaaaattat aagaaatcat aattcataat cacatgtaca   1620
caacataaat cacctttaca taccatcggt tagtctaagc actttgtcgt gttgtgttcg   1680
tgctaggcca ttgtgatggg gtgacaacat cggtacgaca ttggatctcg tactgtattg   1740
acacatgtac tgtgtgaatc gtgttgtatc atgctgcaac actatgaatc gtgttgtatt   1800
tagtgtcaac ttatttagca cgactcactc gaccatctgg atcatgtatc taaaaaatta   1860
gctggctaaa aactaacaga tattagctac tccttactaa tcctgggcag ggcaggagga   1920
ggggcagggg ccccccctccc tttcctagac gagctagcaa acagcggtca gcagcaggga   1980
cagtccattt ccgtctgacc cgcccgcggc cgttccccca ccccgccttt ccttgcaccc   2040
acccagcaag cagagcccac cggatggacg gacgccccgc gcgccggccg gccggtcgat   2100
tcccccactc cactcgccgc ccgcggctgg gctgcgctgc gcatcgacga cggacgacga   2160
cacaatcacc cccacccccc gtccaatcag cagcggacga gggacgacca cggccccccg   2220
tctgccgcac gcgcgcccgc tctgccagct gctgctacta ctgctaaacc tcgcccacca   2280
gtcgcgtgag gaaatagcaa cctgcttgag ctcgttcgct cgctcgcctg ccttcttccc   2340
tgggcaagct agctagctag gatcgaggag gagctctgcc cggccatgca gcgtggggat   2400
ccgctggtgg tgggccgcat catcggcgac gtggtggacc ccttcgtgcg ccgggttccg   2460
ctccgcgtcg cctacgccgc gcgcgaggtc tccaacggct gcgagctcag gccctccgcc   2520
atcgccgacc agccgcgcgt cgaggtcggc ggacccgaca tgcgcacctt ctacaccctc   2580
gtacgtaaca gtccgttcac tcgatcttct cattatatcc atccactgca tccctactat   2640
agacagacag tacatgcgtg cgtcggtgcg tgttgtacac gattccaagc catcagccag   2700
cttaacccgc atgcctgaat ctgactaatt ctgatctgca ggtgatggta gatcctgatg   2760
cgccgagccc cagcgatccc aacctcaggg agtacctgca ctggtaatct actactagta   2820
```

-continued

```
gctagctagc cgcatatccg tttccatcca tccacgtact agtctacaaa acaaactgca   2880
tgcttcgttg ctttgcttct ctgcagcaag catggcctta gaataaacga tctcggtaca   2940
tatatattta tctatttatc agtctaagat attttaaatc ttactacata tttttttaa    3000
atgaacctat attcttaatc gtatataaag taagtataat tacatactca tatactttat   3060
atgcacttgc atatttttta tcatactatt gtagataatt tagtgcgacc atatacttta   3120
tttatatgta cttcatggag acatatatat atcataaatg tacatatata agaaactatt   3180
tcttaaaaat gcaaaataat tttcatatat acatacatat atacattgca tatggtaaca   3240
cacgtactgt ccacttcccg tctctttcag catgctacaa cacacgtact gtcaggatct   3300
tgtctacatt ctccacctcg tacggtaggt agtactgtgt actagcatga tataaataaa   3360
ctaatccaga gtccaccagc ctccctttcc agttctagag atcaataata tatgcaagca   3420
aactactatt tagttgtgaa tgacattaga tatctacctg ggcgcatttg tagaaacatt   3480
atcccgatta agagtaaaga tgttactaac tgccctgatc acagatacaa tatcaaatat   3540
ctattcgaca tgttctttac gctatatatg tgtagttagt tcgttctcga atatttgtcg   3600
ctggctggtt catttttcaa ctaaaacgtg acaaataaat tagaacgaag agagtactgt   3660
attagaatgt tagtttatgc aatttcaagt atttgtacag aactgtggaa gatatcgacg   3720
catgttgctg ccacatgatc tgatgtatta ctagctagct tttaaggcac acaatagcaa   3780
ccatgccttt tattttccca ggcaaattat ttgagatggt aactcattcc agacatcttt   3840
taggctagtg gtatgcatta gatttcgtta acaccaatac ccatatacca tctgtgtaga   3900
aaaaatgaag tagataatct gtagatgcac caatatcata acctacgtgt ctgccgtcca   3960
taattctttg gaaacttcaa attcctaaac catgagtaat cgtataagag catcaccata   4020
tcatatatct atccggtctc ctatactaaa aaaatactac ctccgttctc gaatatttgt   4080
cgcccgctag ttcatttttg aactaaaacg tgacaaataa aaaagaacgg agggagtaac   4140
attttaaaag aggatgtgca ttttagaaca tgaggtgcta caaaagatct tctatctcat   4200
ttcctatatc tataatttta agagatattc taagagatgc attatttctc ctaaataaaa   4260
gaaacaaccc tcccttatct atccctaaag aaatatagga agcaaatttt aggtaatcta   4320
ctacaatagt gccctcttaa ctcttatatc ctaaattaat tttaagatgc tcttttaaaa   4380
taacgtattt gagatgcaat ataagtgtgt gtttggttta ggagccacat gggatagtta   4440
acctctatcc taattttttt agttgggtgg acctcatctc acacgtttgg ttagagggat   4500
ggggtcattc taggttttct gtttggttca ttggaaaata gatgtagatt gagaatctaa   4560
cacatggatc ccacgtgtca ttctctttct cttcccttct ctaccttctt ccctaatcat   4620
gctcatcata ccccccatca tgtcacgtgg ttggaacgct tgtaccacac cgcccaattg   4680
ccatgactcc tacatcgtgc cctgcatcca tagtttttaa gctacactac tcatcgtgtc   4740
gtccatgttt gccacaacca aatcgtcacc cctcactagc accaacgggt gctcgagctt   4800
ggcttgcacc accggagttg ggtctgtgtg ccaccaccac ccctcatcga tcatcatcgt   4860
gctcaccctc gagctcgacc catcatcgct ctgctacgtc cggacatgcc cctgatgtgg   4920
gttcatttgc tccacttgaa tcgaatgaat tggatgaatc catatctatg aggaatattc   4980
tttttgcggg atgaacccaa ccccctagtc tctcaaaaat ggattcgacc ctacttgacc   5040
taatgatacc tttgaaccaa acacacacta aaatatttgg tggagatgct ttaaccattg   5100
gttttatatt tgtactcaag gcagactagt ggatgcaatt actttatact cctactcgaa   5160
acatgagcaa ttgccttaat ggcatggcac caagaaacat agaatacatc tttgagctag   5220
```

-continued

```
tcccaagaaa gaataggtcg gttgcctgtg agttcaatgg tgggaattgg atcaggtctt   5280
tgagaagcaa gatcacattg ttggttcaaa ttgaggaatt catctccctt tggattagac   5340
tccaagattt ttatcttcaa ccgcaggttc cgaactccat tacatggaaa tggagccttg   5400
acaatgtctt catagttaat ttagcctaca aagtgcaatc catcaaatct tgcagccaca   5460
tcaaatctag tcttgcaatg gaaggcaagg gttgatgacc caacatgtaa ggtttttcct   5520
tggattcttc tacaggacaa actcctcact gtgaacaatc ttgccactag ggttggcca    5580
caccattcga gtcgctccct ctacaatctt gccactaggg gatggccaca ccatccgagt   5640
cacaccctct acaattggtc cctagagact aagggtgggc attttaaaac caaaaaccaa   5700
acccgaactc gaacccgaat aaaccaaatt atcgatctat ttgggttttg aggttcaggt   5760
ttggttccta catgtactat attttgaggt atgagtttgg gttcgttttc tagcctttaa   5820
aacctaaata gaccgaataa cccgaaattt aaaaaactat tagtatgtga tgatattatt   5880
atgtgattta tgaacttatt agctaaaaat tatgatgaca tcttaatgat ggtatatata   5940
tctctatatg ctatttttta tagtaacatg ttgtaataat agtacttcaa attaactatt   6000
tattatattt atatttatat taacaaaaga cactagtctc tctactattt gatctatacg   6060
gtggatgaat agaccgaacc aaaattgtgt gtctattcag gttcgattcc caaaattatt   6120
tttgaaaatt ttggttctca tttttttaga actcgaaatt ttaaaaacta aatagactga   6180
atcaaatcac ccttatagac tgaatgccca accctactag agattggcct tctctctatt   6240
tccattgccc tttcgcctgt tgtgcaggat tatattctag cttgggaagg tatgaccctc   6300
cctgcctagg cagacttggc tcactcctct aacattaagg actggtggga agcagcgtcc   6360
tccccactcc caaaaaccca aaaccgtgag ttcaacgaca tcgtggtata cactctatgg   6420
aacctatgga aggagagaaa ccagaggatc ttcaaaaata gctctctaaa ccctatccag   6480
gtagccttga ggatcaaaga ggatgtttta agttttaggt gggctatatc taccctataa   6540
ttgggttgtt gcagtctctt agcaactacc tgctctatgt gggtctgctg gaaatgttcc   6600
tcccaccgtg tgtgttaggc gatgttgtat ccggtcttcg gaccttgttt cttgttttct   6660
aaactctttc cccattaatg gatatgcaga gttcctgcat ttcattcaaa acaatatcga   6720
aacatgggac atgagtgtat tttaaacatt gaactttatt atctttgatc aataattggc   6780
ccaattgtat aaaaagttta tagtacaaaa cttgtaacat tatatttgtg tacataaata   6840
ccttcttcag catctggtcc accaaagaat caaccttaat ctacctagga ggcaataaat   6900
gaacacaaca tccacaaaac ttggacaaga atgcataggg atctacttgt taaaacatgt   6960
agtagaacac acatatagta aaacacacat gagatggaaa tgtgttgcgt gttgtcctct   7020
tcttgatcac atgagcatct ccgacaaggt gcatcaaaat agtgtaccaa aaatcaaaat   7080
actacattta aagtgtttag gacactaaaa acaaattaag ctacaacagt taagccccac   7140
attatatatt ttagaaaata attacattat taggaaagaa aaggttgaag atgatgtaga   7200
aaacaagaat aggacactaa tctagggtgt agtatgtttg gatcacttac tgatgtgccc   7260
tatatttttt gataaaaatt gtaaatagga tattggtgtt gtttttttatg agttaaaccc  7320
tatatttcaa agtaggaaat tgttttaagg cactaggtat gttctaagtg tggaatccct   7380
ctccacctaa ctaggttgtc ctttttcagc atctattggt ggatagccaa ccacaaaaaa   7440
ataaaattga catttttttag aggcctaagg gcaaagaaaa actaaaacaa cgaaggagta  7500
acgagctgat tttgtgaagc actaactaga agatgacaat ttcggtcagt tgctcgttcc   7560
```

-continued

```
gagcgagtca ccgaaaaatt tgtctcgaaa gtcccctttta cgactagttt gaaaacttaa   7620
atcccttctg ggattttcgg gaattaagga gaaaattaag gctaatttcc atccctcaaa   7680
tccccaggaa tcccgaaggg atttaagttt ccaaactagc ccttagatag aaggtctcct   7740
gtatatatat gtcaaggtat ttggacaaag caccattaaa agagcacctt gtatatcttt   7800
tttctgaata cgcaggagag ttgtgtatta gtatattaag aagagtaaag gtctgggaac   7860
agatcaaaat acaaggacac tactcataga ggacgaaaac acaaaaacat aaagagactc   7920
gtttatggcc caaaacacga cagcaacgat ctagccgtta gagagtaggc gcaggccaca   7980
agctagagcc ccttgtatat ccatgagcca acttaagggt gtgttcggaa gcaaagtatt   8040
ttaaaactat gattttagaa tactggtttt aaattgttat gacacaacta tgatattttt   8100
tacatctctt taagcgatac ttatttgtag acaaagtatc tcaaaccatg atatctagta   8160
tgcatatgtt agaagctagc tataaacaaa aactttggtt tagagtggag tttcaagtac   8220
tctaaaaata ctataaatac tataggaact actaaatcat gttatttaaa atagaatttt   8280
ttacagagta gttaaacgcc tcttagcaac aaaaaaaccc atagtactta ctccttgtca   8340
tgacacttca gtgccgcagg gctagagccc aatggagtca aagttgggct ccccaacgaa   8400
gccatatcac tatatacatt ttccgttcat caactagcta gctagctcaa cgaccatttt   8460
tctaatgggt ttttcttttt ctaaagaaaa ttagttcatt ttcttttggc agaagttcac   8520
atctcgataa aatttatatt tatggttagc ttggcaacac cattttattt tcaagaggtt   8580
tttattttat caagaaaaat tagttcattt tctcttggaa aaataaaaat ccattagaaa   8640
aatggggttg tcaaactagt ccttatttag ttttccattg ttaatttact accggagtaa   8700
tttgagcgat gtggagaatt gaacttgaat ggcatttgac tgtaattagt tagtactgtc   8760
tcataaggaa aatatttttc tttagaaaaa gatactgaag caggctatat ttcttcaaca   8820
aaagaaaaga ataaaactga aagactcaaa gcgctaacat acaataatga cataaagctg   8880
attgatagga cagattatta gaagatccgt gcacacttgt tttggtgttg acaccgcgcg   8940
cctagcttta agtagctgct agttaatttg attttgtaac tgttcaaggc gagaattcaa   9000
atattatcta atgaattaat gatgatacgc cgcatcacct gaaacacaag agttctttga   9060
acagtggcga ccaatatctt ggattcttct gctgtatttt gtttctatag attcacctgc   9120
aaatatcatc tttatcacaa tcgtacctgt aactcaaatg catctatagt tacaaagtca   9180
ccggccagcc tatacacata tgctgatgtg caaaacggca agaccttgct agcattatat   9240
tttggggaca tactaaagat ttcctgggtc agtccagtcc aattacagca acttctctta   9300
gaatcttgaa ctcgcgatat accacactga caaacaaaca aatcttatgt acaagcatgc   9360
aagcgagcct cttggtctgt aagatcacga tctaactgta gataagatcg tgattcgtta   9420
agaggtcatc tataaatcta cgtgagctag tggtggaaat gtttaagtgt taaatgtaat   9480
taatggttag atcataatct aacgaaccag caacctcgct tgcacataag accttacagt   9540
actaggttcg tacgtgacct ttcatgtata tagcacacat acatgtacga gtctactata   9600
cgtgttacag cacatatata tacatctaac agatttctcg aacctgagcc atgatctgat   9660
gatagcatcc catatacaaa gatgtgccaa ctcaaagtcg ctttgatctt ctgttgcagg   9720
ctggtcactg atattccggc gacgactgga gtatcttttg gtatgtacta gtacacagta   9780
ggaaccatga acgagcttaa ccaaagtgct agctaatgcc atgcttggac atccatgaac   9840
gcgcagggac cgaggtcgtg tgctacgaga gcccacggcc ggtgctgggg atccaccggg   9900
tcgtgtttct gctcttccag cagctcggcc ggcagacggt gtacgccccg gggtggcggc   9960
```

-continued

```
agaacttcag cacccgcgac ttcgccgagc tctacaacct cggcttgccg gtcgccgccg  10020
tctacttcaa ctgccagagg gagtccggaa ccggtgggag aagaatgtga tctcgacccg  10080
gctgggtgga aattaataag atgacgggta atcgggtata tgtatatatt tatatatata  10140
tatatatgta tatgtacgtg tatttgatct ggtggccttt tgttacattt gggtgaggtg  10200
tatttgatat tatctgtgga agattggcgc attctctggc gcatatttga tagctacatg  10260
tatctattta tacagatata aagcgagcaa taatatgcat atgagagggt tcagccacat  10320
cagtcaatac tctctccttt atactgtgat gatgactact tatctgaatc atctgattac  10380
aactacatgc ttgcttgcta gctcactggt cgagctgctg gatgcagcca tgcatgcaga  10440
gaaatgaacc cacacatgcc gagggagacg agcagctgct tcctctcgcc atttaatggt  10500
ttggccaaca cacagataaa tcatttgggg gacaagggca aggatcaaga tgatggattg  10560
gggaagaaca cgggtgtgcc ttcacttccc ttccttcctt ccttcctttc tttctttctt  10620
tctttttct ttgagagaga acgagaagaa tgcgggccgt agttgcactc gagaccccgc  10680
ccaacggcct gctacgggcc attaaatcga acattccatg cgaacgcaaa aaaaaaagga  10740
cccaagttag cacaactcgc ggggggttc ggcccagcac actcctagag tcagaactga  10800
aattcctagc acatgcttca tcacccaaca aaagaatcag agcattaaga gcgtagtaca  10860
gatcaacgat tattagcaac accaagacca taagtacttg catccgagtt atgtacattc  10920
tatactgttc tctaaggtct gagtgcacat ggaaagatga gagctatcct gtccagcttc  10980
agcttgcagc actatggcgg tacctggcag ctgagccata cttctgataa gaggccaaat  11040
accggacgaa aaatgaggaa gcggcaacca gggggtacaa atgctgagat tatcatgaag  11100
ggaacggcga tggctcctca gctggaagct tgtccgcggg ctttagctcc cagttgcgtg  11160
gattggtgtc cgtcgaatca gacttggaaa tgtacagcgc cttgttgtgg aacttgtgaa  11220
gtgttttccg gtgtccgatg cttacgtagg taatgccggc agcttcaatc tgactgtata  11280
gatgagcctg tgacacaact aaagctagtc agagttgaca tcaaagtagg tgcgggtaca  11340
ctggttcttg gtccatgcaa aaaggatgtc ctacagcaac accaaccctt ttcttttctt  11400
ctactctgtg atggggtgaa agcatttgtg cgactgtgtg gactatgaat aacaagcagg  11460
caaaaaaaca agtatagcag tgtaactaga gttcagttac ctcgtttgct tcatcgagtg  11520
cgcttgtcga ctcgtccagc aggaccaaag tgggtgtagc aagtaatagc cgggcgaacg  11580
cgagacgctg ctgctccccc agcgaaagaa cactggccca gtcatgggta gagtccaagc  11640
cgttgaaacg aggcaatatg taacccagct tgacgtcctc aaggacttcg atcagttcag  11700
ctgtcgaggg cacctcggat ttggcaccga ccagatctga tgtggagact tcggacagaa  11760
aaggaagagg atctgctgat cattttgaaa ggaaaaaaaa ggatttagga taaatgcata  11820
tgcatgtttc aagaaaacgc tgccacgagc actttcacac gtacacttgg tagtttttt  11880
cccctgaaca cactccaaac agatttaagt agttttgttc gacatcgtac aactaacgag  11940
aagggctacc tgagttttta tcatcattat ctggtgagtg ttgaacctct tcagtccacg  12000
taggatagag caactgttga cgaagtgtcc ccagaaccat atacggcctt tgtgggacga  12060
agaatatgcc attatctctt ctttgcttgg aactttgcaa cgattcttct tcgcccttta  12120
aattcatgct ggatggttta tcagaacttg gatttggttt ttgaagctgc gtagaacctc  12180
tcacgtggta tatgatctcc ccagttccac tagtccagag gccggccaaa gcacgtaaca  12240
gcgacgtctt cccacttcca ctaggtccca tcacctaaag tgaaaaaaaa agcatagcac  12300
```

-continued

```
ctcagcgatg agtcaagtgt acagagataa catttgtttt gccgaatgcg caagtagtta  12360
aagaaatgga ataccagtag gtggtccttg tcttttagtt ccatagtgag gccagtaata  12420
agaacatttc cacttcttgg tgttaacaat gtcaagttac gaatttccag aaccatgcat  12480
ggatcagact gtgttagtga tccattagaa ctaggaacac aaggaccgct gcttctgaaa  12540
acaatgttga tcccatcaat gctatcacgt tgagatgata gagaggactc gtttccatcc  12600
aatagatcat caaactcacc tatattacaa agaatttaca gttaaccacg ttaatagagg  12660
gggtatagag gcaggaaggg aggaagggag ggaggggaga agtcacctag acgatcgata  12720
actgctgaga atgcactaat tgactgaaat tggaaaacaa tgagagagaa atcactaaga  12780
atatgattga aagcagacac cgattggttt attactccaa actcaatttt ccctgagaag  12840
tacattggag caacaactgc agctggcaga atctgaatca aatatcgata accattggtg  12900
aaaaactcca gattccgaga agctatcagc aattcctgat acataataaa ataaaatata  12960
tgaactggcc aacctggaaa aatatttaac agtaggaatt tatggctaaa tatgaagata  13020
cagagcagct gcattgtgat aagtcagtag tagagcacat aaagagccag ttactcttac  13080
agtaaaaaga actcaaccaa cctacaaaga attgtggcgt gtaaataaga ataaaatagg  13140
cacccaaatt tgagttgaag aggactcgaa tctgggtggt agggatgtag acccacacct  13200
ccccaggctc agttcctcac ctgccacagt atcaccatta ttagcagttt gttggagtat  13260
atcagaatca acaacttgta tttgattatt acaaaagaaa atttattgcc caagaggtat  13320
gatttacatg attatcagat cttagtcgca gagaaaacca gggtatagaa atacaagtga  13380
tctgctttac taatggcaaa                                              13400
```

<210> SEQ ID NO 64
<211> LENGTH: 1840
<212> TYPE: DNA
<213> ORGANISM: Zea mays

<400> SEQUENCE: 64

```
ccacgcgtcc ggtactgtga gagtaaggct aaagtcgccg gataatataa gaccagcaat     60
aacaagctag tttgccctcg ttctccaaca aaatgtctga tgtggagccg ctggttctgg    120
ctcatgtcat acgagatgtg ttggattcat ttgcaccaag tatcgggctc agaataacct    180
acaacagcag gttacttcta tcaggtgttg agctgaaacc atccgcggtt gtgaataagc    240
caagagttga tgttgggggc accgacctca gggtgttcta cacattggta agcgaataaa    300
atacgatgtg tgcttgtgtt ctgtcatgtg tggagccatg gcagcatcca ctaacaatta    360
acctcttata tattgtcaat gtgactacac aacacctgaa aatttaaaca gctcaatatc    420
tcttgtgctc tagctaactt attggttctt catttacata aggtattagt ggatccagat    480
gccccaagcc caagcaatcc atcactgagg gagtatctgc actggtaagt ttgttcatta    540
ttagttcttt attagtcaaa tggcaggttt gtttgaaatg tatttagctt tcccagtgaa    600
ctaaatagct ttgagtgtgt tgtcctagca cgacacatgc acatgttata tatatatata    660
tgttctcacc ttttccttgt tttaatgtat catagacatt tcttccttgt tctcaccttt    720
ttagacattt cccagtgaat ctaaatttgt gctgcatatg taggatggtg atagacattc    780
ctggaacaac tggagccagc tttggtatga tcccatgaaa tcatattttc cgtctggatt    840
ccttcgcttt tagcatatat catctatgat cgaaaaagat cctcggctgt gctaactgac    900
tcacaatcaa caaaagtgat ctatcacctt ttagcggttc caatgaccct aactcagaaa    960
aacgtttttt ttagaagtca tacatatata tagagagaaa aatctagatt cataccaaac   1020
```

-continued

```
aaggctaaag tttttcttag cattgtgaac agaattggag ttcatatata attaaacata   1080

aatgctaatg ctaatgggag atgtttggtt cgaggaatca cttcatccaa aatgagatgt   1140

tacatcatag gtccgatcca tttctcaaat ttggtgtgat aacctcattc cttatatttg   1200

tactaattaa atatgagaaa tgaggtgatg atagatcaac tcattccatt tcacaaacca   1260

aacaaaaaaa ataaaaagtg gaagatgatg aactagcttg ttccttaaat caaacaccct   1320

aaacaaaaaa agagaagtgg aagatgatag actagctcgt tctttaaaca aacacactaa   1380

atatatacta gaccatctct tgctgcaggt caggagctca tgttttacga gaggccagag   1440

ccgaggtccg gcatacaccg catggtgttc gtgctgttcc ggcagctcgg caggggggacg   1500

gtgtttgcac cagacatgcg gcacaacttc aactgcaaga gcttcgcccg tcagtaccac   1560

ctggacgtcg tggctgccac gtatttcaac tgccaaaggg aggcaggatc cgggggcaga   1620

aggttcaggc cggagagctc gtaaggaatg aagcatgcac agaagaagac tgcagcgctt   1680

tcgcatgcat atgatctatc gtcgtcctgc ggaatatata tatagtaacc gttgttatat   1740

ggaataatgt gcatgaaatt ggtatcagat gcaccgaccc gtacgtacgt aattaatgtt   1800

tgttattaca cgcagacata taatatacat actcattcac                         1840
```

```
<210> SEQ ID NO 65
<211> LENGTH: 7160
<212> TYPE: DNA
<213> ORGANISM: Zea mays

<400> SEQUENCE: 65
```

```
ttcgatatca agcttatgaa attatctaca actcctttta ccaacctaaa gtttaattct     60

gttgataaaa ttgcctaaaa cttaagagaa cagattatgc atagaattat gagactaaaa    120

aactgctata atcaaactgc aataactttc tgatctgatg tctgattgag ggcccgttca    180

tttctactgg aagagaccag gattagttcc aaatctccaa aacttatagt aattattgaa    240

ggaatccaag ccagatttat tccacccctt cattccatgc gaaatgaata ggccctgagg    300

tgttcttcgc ggccacagaa agatctataa attgtctata actcatagat agactttttg    360

ttttttgag gccactaaga ccacaaaaaa ctgccaagaa cagaaattgt caaatctgtc    420

attctgtaga aactaaattc gaggtcaaaa cctaacccca catctaatcc aacctctaat    480

cctttaatcc ccatgatcga caacctccaa aagcacataa ttatagggag gaacaaggat    540

cccatcctta cctagggttt ccccaagaaa atctacaaga agagatgggg tagaacatct    600

ccttgatcct ctgttcctct tcaattcaac gtgctcctcc tcttctcgat ccttgctaca    660

taggggaaga tcaagggagg aggaagcaat ggagggcggc tgcaatcgga ggagaggggc    720

ggccagccaa gggggaaaag ggaggggcgg ccaagccaag ggagaaaaag ggggggtggc    780

ggccaagaga gggaaaaagg gaaaaggggt ggccacctag ggttttgtgg gagaaagaaa    840

agacgcctca tatgaattat gactttgcat ccaacggccc acaacccttt ccctcatcca    900

cgcaccgaaa atcaactttt gggcaacatt tttttgggat attacacaat tctggcagat    960

gcttcgggat ttctgaatag gtctcctaga cctcggtcag tggtgaccct tactctgtgc   1020

gcctctaagt agtgccttag tttgcgcgaa gccatgatga ccgagtaggc tatcttctct   1080

agctctgtca tactgcactt ggaactggtg agtacctcgg aaacagaata tatcgggcat   1140

tgttgggtct taccgtgttt gcacctttct tgtaccagag ttgcgctgac cacgctgggt   1200

gacgttgtga tgtgaggtag cgcggggtcc gggctagtga gtgtcgctag atcagattta   1260
```

-continued

```
atattgtttt aaggactcaa aggctgcagt ctcctctggg ccctaggcaa agtccttggc   1320
tccgcgcagc gttttcagga aaatggaagg ttttgctcga tggaagtagc accctaaaat   1380
tctttttagg gaaactactg taatatttaa ataaatgggt ttcctaatat gggattgact   1440
aaaaaggtta tcatcacatg aattaaattg atattttgtg ggactatata gcagggataa   1500
ggagtcatat tgcatagtga gggacttgat agactgattt cacaaaattg ctcttggtgt   1560
caggatcacc tagatggttt gctggtgatt ggagtgtggt gatcacctag agagattgtg   1620
gatgactcgg ctcgggatgt gtatatgatt gtgagctatt gaccatatgc ccgagcagca   1680
aaaaaccacc tcgtagagag cacttggtcc ttgcacggac taaggaggaa tgacacccat   1740
gtgcaggtta tccaacaagg attaatgggg agtgttaact ctctaagacc tcgcgaaaaa   1800
tcttgagtct tctaaaccct tgttttactt ttcgcaaata aatttgtgca atttacttta   1860
ataatttaca ttcttataat tgttacaata gtatagggtt agaatttggg cgcaaaatct   1920
tttgtataca cattaggcac tcagtttaag tttggaatgc aattacaata ttattatcga   1980
cagacatttt agagaaattc aattcacccc atcttaggta tcatgatcct ttcacaagcc   2040
attattgcta atgtggaggc cataataggg cgacaagatt tggatgccaa ttgagaggct   2100
ggtgatggcc aatttgaggc tataatggag ttccgatgaa cttgaccatg tccttggcaa   2160
acaccatgct tgactaatga ggatggttta ttttccatac tattgatcct tgattcatag   2220
ttgttcggtg gtggtgggtg tgcttgtttg aggagctcat cgctcgtgtc ctatcgacca   2280
tcacattgat ctaatgctct ccactccact cgtaatcaca gtcaagaaag agcacataga   2340
catgttcgtc gaatgatgga tcttggtagc tactattaca agggcggtgg actggtggtg   2400
tggttagcca ccaaggtagg gagtgttcta gtatagtgcg aagatgaaag taaaagggag   2460
gcattaggga gacaatatga ttattgtggt ggtacgacct tgtgatcgat gaccataagg   2520
caccaactcc tccaaagcac gtgagtcttg actatttaag gtttctttat ttaatcaact   2580
ttgctctttc taggttgtgt gggctgacca actaattcat ttgggcagtg ggccaactat   2640
agtggtcttg ggctactgga atctaggttt gatgtggctc gtgagctggc tcattggcga   2700
ttcaagctaa gatgttacct caactcgtta cgaaataaga tcaagccaaa ccattaaggg   2760
tccatttgat tggagagcca catgagcaga gcagttccat tccatatttg aagagcatat   2820
atagtggctc cattccaaat tatgagactg gagtggaatc attatatttt ttgtttgggt   2880
ccatatagca aacagaggga gaagtgaaac gatgagattc caccaatttt tttagagcga   2940
gatcatcccg aatctaatgg gaatattctc gatttagagt ggctccaccc caccctctct   3000
attcgttccc caaccaaaca cataattgag cggctccatc gcacctcgct ctccaaccaa   3060
acagaccgta acaaatcgaa ccgagcgagt tatcgagttt tttatccaac ccttattagt   3120
accatgatct taacctaata caagtgtgtg tcgtgtgtaa gttataccct ttatttatgg   3180
caagagatct gacatggttg atgcttgcgt tgccatcttt catcctttca gaccacacac   3240
gggggcaggt ggggctcgag cctcctatcg ctcccgagcc aatagtgcct ccatccccat   3300
atagcttccc gtaaaattac atcctatatt tctcattata tattttatga ttttcatcgt   3360
tcatcgatgt ttcaatatat aactacttta aactatgata tttgtatgtt gtgagcggtt   3420
tagtgagatt atgtctctgt tgatcatagt tcagcctctc ctaaaaattt tcctggctcc   3480
gtcttcgttg agcgcgcatc ctttgcatcg ccagcgtacc gtgcagcaaa caaaagggcg   3540
gcgaagctag ctttagttta tgcggcagat ggatcggaaa tcggataggg tgaccccagc   3600
acagcaccag cagatagcgg caatgaagaa taataccagc aggcggacat tattgtagca   3660
```

-continued

```
gtatatgcac aagaaacacc ctacacatac atatgctgcc cggccgggca aatcagtgtt   3720
ttgcacaggc actgtgaaaa aaaaacacta aaaaaggtga ccatgaaact tgcgcctggt   3780
tggcagacat actctcgaca gattagttgg ggctagcgct acggaactga tcgtcgagaa   3840
gctagcatgc agcagctgcg cgcttaagat tcagattgag atggacagat agacgtgtac   3900
gtacgtgcgg tctgcaggag ctagctgagg agaagctagc tagctagcta gctgctatgg   3960
tagccactgc ttttgggccg cgcgggggtc aaaagcgcgc gcgcgatgcg gatgccccgg   4020
ccccgcgcgc atccagcata ctagttctgc atataccgag tgtgtatagc tagtgtcatc   4080
aggtccacac aagaagaatt ggagatagag aaaatgactg gagattctat gggggacatg   4140
tgcagatgtg ctactagcag actcagacag cagcagcagc agcaacaaaa actattagga   4200
acagcacagc agctagccac acagtagtaa accttaactc atatcagcca atagcatgca   4260
gaagcagcaa gttggtgacg gtaccatgca tcatatatac tcctgatgag cttgacgtac   4320
ccgccaccgg ccactatata aactggccat cgatcatcag ctagctagcc agcagcaggt   4380
agtaccttgg ccaaaacgac ttagctatca agctcgaccg acgaccgaag ctaagctacc   4440
aagctactag tagtcttctt ggtcacgttg ttgattgcag cggtcgagca cacacaagct   4500
agctagctag ccgctagagc tagggtcgtc ggatagatcg acatggccgg cagggacagg   4560
gagccgctgg tggttggtag ggtggtcggc gacgtgctgg acccccttcgt ccggaccacc   4620
aacctcaggg tcagctacgg ggccaggacc gtgtccaacg gctgcgagct caagccgtcc   4680
atggtggtgc accagccaag ggtcgaggtc gggggacctg acatgaggac cttctacacc   4740
ctcgtacgtg tatatatata tatatatata cacgtcgtcg ttttacttct cttcattggc   4800
tagctactta gctagctagc tagcttataa tgatagcccg ttgatccatc gagatatgat   4860
cgtacgtgat gccatgcatg cttcgttctt caggtgatgg tggacccaga tgctccgagc   4920
ccaagcgacc cgaaccttag ggagtaccta cactggtaaa atctatatac gtactcgtcc   4980
tgcacacact cgatcgatcc cttcactatc tatatatatg tatacataca tatgttatat   5040
attacaagta aaatctcata ctccctccct ccgttcttaa atatatgacg ttgtcgttga   5100
tttttttttc aaaaaatttt tgaccactca ttatatttaa aataaatcat gagttattat   5160
ttgttttgct gtgatttgtt ttatcactta cgcaccgttt cgatccttgg aatgcatttt   5220
aataatagta atttggcttt atgcaaaata tatttgtata ttattattag caagatgtcg   5280
gatatattta tgtgctacat ttttaatata aaggagtgag tcgaagagcg tcctataatt   5340
tggagagtag aaacaaattc tactgacaca taaaataatt tctcatcctc caccaaatga   5400
atttgagata gatttatatc tgaactttag aaacaggtgg aatgttaaat ttgaagctaa   5460
atatgttact ttattaaata aattttaatt tctctaaaat gaatggatcc aaacggttcg   5520
ttaagttaat tacttaaaat tttacatttt taaatacata tttttaatta gacgagtggt   5580
caattttttt gaaaaaagtc aacaacctcg tatatattta agaatggaca tcgtatgccc   5640
gggttggttg ggcatgtcct ctctgatcta ccgtcttctt tcatgcaggc tggtgacgga   5700
tattccggga actactgggg cagcatttgg tatatatctg tcactccgtc cggtcataaa   5760
ctgtctgttt gttgtctgtc tatacaactg tgtccagaca aactttttac tacacgtacg   5820
tggccggatt tcctatatat atattgtgca tgcagatcaa acgcatatat acggcgtcac   5880
acttgtcgat cggccaccgg ttatatggag acgtacaaaa gaattctatc tatagatata   5940
tatgtatatg ataattaatt aagctacaag ctactataga tatatatgat aatttattat   6000
```

-continued

```
gttcttgata gccaagttaa taaaaccata atgacaaaat aacaagaaat aaaaaaatca   6060

ggcgtaggaa ttataaatag atatgcatgg tgctgtatta tatgtatgtg atgatgatga   6120

tacaaaaaaa ataaactact actggtgtgt ggcacccgtg ctgcagggca agaggtgatc   6180

tgctacgaga gccctcggcc gaccatgggg atccaccgct tcgtgctggt gctgttccag   6240

cagctggggc ggcagacggt gtacgccccg ggctggcgcc agaacttcaa caccagggac   6300

ttcgccgagc tctacaacct gggcccgccc gtcgccgccg tctacttcaa ctgccagcgt   6360

gaggccggct ctgggggcag gaggatgtac tcgtgatcgg atgcatggtt acataccatg   6420

cacacactac tcactccatc gtctccatgc atgtagacgg acgatggtgc ctgcatcgat   6480

cgtcaactac tcaacaatta cgaactagaa atacacgcgt atatatacat atataaatat   6540

gcatatatac cggtactgta catgtcgccg tacacgcgca ggtggctgct agctgcttgc   6600

tataccggcc ggtactgagc aggcagcatg cgctatatac ttgcttggcg acgacgtgca   6660

gtgtgtgtat acaataatga gcggccggct agcagggcga cgagccgtgg ctttataaag   6720

caatacatat atactgcagg gatgtgtgtg tgcagtgcat gccaaggtac ggtaatcgta   6780

ttattgtgca catacacata tgtatacgta catatgcgta aatatgaatc tgtacgtata   6840

catatgcatg ctggttaatt aaggcgctat cttgtacgta cgtgcttggt gtaataataa   6900

tataagtcct cagtggagaa tatatataat aataaattaa gaactatagg cttttgtgtg   6960

gacaaaccag cagggttggt atatacatta atttcatgca tgattttctc cttaatatat   7020

acacaaatta tcgtcataag ggtctcctct gtttttgatc gtgcaagcgt gctttgaact   7080

tgaacgtacg tctacctgcc ggggcacgcg gaataatgat acagtggcgt gtagctctca   7140

ccagtacaca gaagcttgat                                               7160
```

<210> SEQ ID NO 66
<211> LENGTH: 4711
<212> TYPE: DNA
<213> ORGANISM: Zea mays
<220> FEATURE:
<221> NAME/KEY: misc_feature
<222> LOCATION: 2376, 4660
<223> OTHER INFORMATION: n = A,T,C or G

<400> SEQUENCE: 66

```
taagcttctg caaagtaact gtaatgcaga ccatacatgt agatagtgga gaatgattcc     60

caataataca agatttttac tgtcccactt tcctagagat gtgttatctg ttatgttttc    120

ttgtggactc cacagtgacc tgaaatactt catttcagtc atgaaagaac aattccgtgc    180

atacgtagtc atcaaagagg ggaaaaatgc tttgtcccaa gaaattcaac aaagaaacat    240

gatgcattgc ttgcatagat tttatctgta actgttacag aagtatgata tcctttgttg    300

gctttcttgg aaaaagtggt acaaccttcc tgttgccatt gcagctgcat ccacaccata    360

cccaactaaa agacacacat gacacatgcc tcacatcctc tttttatatc ctacactcag    420

cagcagcctc ataaccgcta taaatagagg cttgtcctct accaatgccc aataagcagc    480

tcacagtatt cttgagtgca ttcgcttgct ccattcagtc agagcatttc ttgtgcaaaa    540

ttcaaatacc tgtcacacca accatgtcta ggtctgtgga gcctctcata gtcgggcggg    600

tgattggaga agttctcgac tcctttaacc catgtgtcaa gatgatagta acctacaact    660

caaacaaact tgtattcaat ggccatgaga tctacccatc agcaattgta tctaaaccta    720

gggtagaggt tcaagggggt gatttgcggt ctttcttcac attggttagc aatcaaatgt    780

tccatctttg acaaatattc tacaaatact actacttctc tgatggccat gctcatcaaa    840
```

-continued

```
tttcaggtta tgacagaccc agatgttcca ggaccaagtg atccatatct aagggagcac    900
cttcattggt aatattcagc atttcttacc ttagtaggga tgttaaatag catatgttgc    960
tcaggaagat agaaccatat cttgcataca aaattgcatg ctttttagca cttaaatggg   1020
agtagtgtga ctaaatggca tccttcacat ttgcaggatc gtgactgata tacctgggac   1080
aacagatgcc tcctttggta ggttctgctg aatcaggctt agtctattcc atgttttagt   1140
tgttctttga attaataaca attcatctga caattgcagg gcgagaggtc ataagctatg   1200
agagcccaag acctaacatc ggtatccaca ggttcatttt tgtgctcttc aagcagaagg   1260
gtaggcaaac tgtaaccgtg ccatccttca gagatcattt caacacccgg cagtttgctg   1320
aggaaaatga ccttggcctc ccagtagctg ctgtctactt caatgcacag agagaaactg   1380
cagctaggag acgttgaaaa ttccagctct tattgtccac ctgatgataa taaaggcctt   1440
ctgatcttct ttctaggaag ccaatgaact tattctacat taaattctcc tgagccctac   1500
cgtataaata aaccagatgc gttttgctga ttgtattagt attagaatgc tttgtacgtg   1560
gcaagaatga gaattacaaa tggtcaatgc ttgtggtaaa atttgatgtg taagacatct   1620
atcactgaaa gtcagaaacc aggcttagtg gacacccctc acagggggaa aatttcatct   1680
tctgtttgca gcttcgcact ttgtgcactt tttctaacat gcaaactcct ggaaacaaaa   1740
ttcgttggac attttgcacc aacttataga actataaaca ccctaactgc attcgactac   1800
tacattgtta agcaaggcat gtatagaata tggagatgtc taatttacca acaggaatat   1860
aggattgccc actggaagca tgaaaagtat ggagacatca atttttgtgc ccctattttt   1920
ccttcagctt gtccttaagc caaatgacca gaaatccata tcatgtatgc ttgaacatgc   1980
aagatagctg catatctttg aattaaagga cagacctagt gttggctgct cccacatgtg   2040
tgggttctag ggaaggagta accaaggcaa gccttatctc tgcatttttg cagagaggtt   2100
gaggaaaagg gaagagaatc ctgtacaaag caacctcctt accagccaga gggtctgagg   2160
atgtcacgag ctaacactaa aaaatcacct ggacacctgg catacaccaa gaaatgatcc   2220
aaccagaata caaaagactc acacctgacc ctctacatga ccttctatgc aaccaaatat   2280
gaatgcaaac tgaatgctct ctttcccatt ggcttctgta tgtgtttatt ggctacatac   2340
aaacaaacta taagatgtaa caatgcaatg tgtacnattg tatcagttta cctctgttga   2400
tgaagactgg ggagtggaat ccccattaat acttcatttc agtcatgaaa gaacaattcc   2460
gtgcatacgt agtcatcaaa gaggggaaaa atgctttgtc ccaagaaatt caacaaagaa   2520
acatgatgca ttgcttgcat agattttatc tgtaactgtt acagaagtat gatatccttt   2580
gttggctttc ttggaaaaag tggtacaacc ttcctgttgc cattgcagct gcatccacac   2640
catacccaac taaaagacac acatgacaca tgcctcacat cctcttttta tatcctacac   2700
tcagcagcag cctcataacc gctataaata gaggcttgtc ctctaccaat gcccaataag   2760
cagctcacag tattcttgag tgcattcgct tgctccattc agtcagagca tttcttgtgc   2820
aaaattcaaa tacctgtcac accaaccatg tctaggtctg tggagcctct catagtcggg   2880
cgggtgattg gagaagttct cgactccttt aacccatgtg tcaagatgat agtaacctac   2940
aactcaaaca aacttgtatt caatggccat gagatctacc catcagcaat tgtatctaaa   3000
cctagggtag aggttcaagg gggtgatttg cggtctttct tcacattggt tagcaatcaa   3060
atgttccatc tttgacaaat attctacaaa tactactact tctctgatgg ccatgctcat   3120
caaatttcag gttatgacag acccagatgt tccaggacca agtgatccat atctaaggga   3180
```

-continued

```
gcaccttcat tggtaatatt cagcatttct taccttagta gggatgttaa atagcatatg   3240
ttgctcagga agatagaacc atatcttgca tacaaaattg catgcttttt agcacttaaa   3300
tgggagtagt gtgactaaat ggcatccttc acatttgcag gatcgtgact gatatacctg   3360
ggacaacaga tgcctccttt ggtaggttct gctgaatcag gcttagtcta ttccatgttt   3420
tagttgttct ttgaattaat aacaattcat ctgacaattg cagggcgaga ggtcataagc   3480
tatgagagcc caagacctaa catcggtatc cacaggttca tttttgtgct cttcaagcag   3540
aagggtaggc aaactgtaac cgtgccatcc ttcagagatc atttcaacac ccggcagttt   3600
gctgaggaaa atgaccttgg cctcccagta gctgctgtct acttcaatgc acagagagaa   3660
actgcagcta ggagacgttg aaaattccag ctcttattgt ccacctgatg ataataaagg   3720
ccttctgatc ttctttctag gaagccaatg aacttattct acattaaatt ctcctgagcc   3780
ctaccgtata aataaaccag atgcgttttg ctgattgtat tagtattaga atgctttgta   3840
cgtggcaaga atgagaatta caaatggtca atgcttgtgg taaaatttga tgtgtaagac   3900
atctatcact gaaagtcaga aaccaggctt agtggacacc cctcacaggg ggaaaatttc   3960
atcttctgtt tgcagcttcg cactttgtgc actttttcta acatgcaaac tcctggaaac   4020
aaaattcgtt ggacattttg caccaactta tagaactata aacaccctaa ctgcattcga   4080
ctactacatt gttaagcaag gcatgtatag aatatggaga tgtctaattt accaacagga   4140
atataggatt gcccactgga agcatgaaaa gtatggagac atcaattttt gtgcccctat   4200
ttttccttca gcttgtcctt aagccaaatg accagaaatc catatcatgt atgcttgaac   4260
atgcaagata gctgcatatc tttgaattaa aggacagacc tagtgttggc tgctcccaca   4320
tgtgtgggtt ctagggaagg agtaaccaag gcaagcctta tctctgcatt tttgcagaga   4380
ggttgaggaa aagggaagag aatcctgtac aaagcaacct ccttaccagc cagagggtct   4440
gaggatgtca cgagctaaca ctaaaaaatc acctggacac ctggcataca ccaagaaatg   4500
atccaaccag aatacaaaag actcacacct gaccctctac atgaccttct atgcaaccaa   4560
atatgaatgc aaactgaatg ctctctttcc cattggcttc tgtatgtgtt tattggctac   4620
atacaaacaa actataagat gtaacaatgc aatgtgtacn attgtatcag tttacctctg   4680
ttgatgaaga ctggggagtg gaatccccat t                                  4711
```

<210> SEQ ID NO 67
<211> LENGTH: 5966
<212> TYPE: DNA
<213> ORGANISM: Zea mays

<400> SEQUENCE: 67

```
acttgcgtga caggaataat caccagaagt agcaagtccg ctcaagtgca atgctgttta     60
gggcatgttc ttttgcaccc catagctcag cagagtggtg cttcagcgtg cctcgctttt    120
ttacctcaag agaaaaagat gctagctcct gggtgcagtt gtgctccagc tttgagaata    180
cccaagctaa gctcactctc cagctgcaaa aagaaaaact aaaatatgtg ttgaaacgca    240
aaataaaata catgtaaaaa taaagggata atcaatcaat ggagagagaa ttcacattaa    300
cgttgtatgc ttctttatat aaagggacag gcaaagaata caagctaaag aactagcata    360
atcaagctgc catctttgac accgttccta cattcactac cacacattat gtctctaaga    420
atttctgaag aaaatgaaat aattaatgca cgtttagtga agattctcta tggtacacta    480
ctaataatgt cttcaattaa ctcctcagtg ctaaatatat acaaattcat actatcattt    540
ttgtacacaa aacataaatt gtgatgtgat ttgtttcagt aaatcacaat caatacgtcg    600
```

-continued

```
attagataca aaaattgtca cctcacttct ggcttctgcg ctcacatagc atgaacaaaa    660
aaaaaacctg gcacactaat aataatcaaa cctaagacta gatcatcacc catgttccag    720
agaaaaatac tgtgaccgcc tctataggga ataaaataat ccatgtggga agccagtgca    780
aaaccgaatg tactaggcga aaaaaaaata ctaaaccatt tctgcattac caagtcaacc    840
aacaagtagc tgcagctccg aacggaagtc aagattttac atgcatccct tataaaccac    900
gaagctaact cccaaaacac ctgagaaatg ctacgatctt ttatatttca atgtgctcgc    960
ttggcttgat cgatgtctga aggaagtacg ttatcagtgg atctctgtcg tcgttcaccg   1020
gagaaacttt aatgatatgg atgtaacaaa gagctttttc ctattttgcc aaatgtggat   1080
tctaggcact taactatttc ggcctgaacg cccatgcata tataataata taaatattgt   1140
gaagggaata aatatctttg agatagatgt ggaaattgga atatatcgga taataaggaa   1200
cttgtatatc tgctgcaagt gcccctattc tatatattgt gaagaaacaa tctgacatgt   1260
taagctatat atgatagtag ccaccgtacg agccgataga gacgctcaaa cctgaacttt   1320
ttaagagctg taatatatga tgatgatcgg tccatcacac tcagctcgat cgatcggaat   1380
atatagctgg ccttgacgtc tataaataga ggccaaacgc cctggtctct tggcaacaca   1440
cacaagcaca cgcacatagg gaacagaagc tactagctcc agcacaaaac acctactgct   1500
tcaactgtac cgttagacat gtcaagggtg ttggagcctc tcattgtggg gaaagtgatt   1560
ggtgaggtcc tggaccattt caaccccacg gtgaagatgg tggtcaccta caactccaac   1620
aagcaggtgt tcaacgggca cgagttcttc ccttcggcag tggccgccaa gccgcgtgtt   1680
gaggtccaag gggcgacct caggtccttc ttcacgttgg tgatgaccga ccccgatgtt   1740
cctggaccta gtgatccata cttgagggag caccttcact ggtaataatt tttatcatca   1800
atgcgagaat tcataataat atagtctata tatatcttgc tagataaagt aatcgtataa   1860
gtaaatactg tactaaatag gggggtatca cctatatatc tactatagtg tagcgcttga   1920
ctcggccatg catgattagc tagaatttat tacgtatata tttttacaca gctgggttat   1980
gcatgcatgg tcttataaat gcatgttcat atatattatc tcaaggcatt tatatgtata   2040
tatagctaat caggggcgtg tttttttgtt tgctggacca cacactggca ctggcaggat   2100
tgtcactgat attcctggga ctaccgatgc ttcttttggt aagtcttttt tcttgtacat   2160
gtcgctttag ttcttgcttg ttttgaagcc gcagaagagg ggaagagtgg gggcgacgaa   2220
tggataaaaa gggtttttat gcatgctgta caaatcagtt cgttctttgt cactccatct   2280
aattaatgct tgtgcttgta tgcatgcagg gaaagaggtg gtgagctacg agatcccaaa   2340
gccaaacatt ggcatccaca ggttcatctt tgtgctgttc cggcagaaga gccggcaagc   2400
ggtgaacccg ccgtcgtcga aggaccgctt cagcacccgc cagttcgctg aggagaacga   2460
cctcggcctc cccgtcgccg ccgtctactt caacgcgcag cgcgagaccg ccgcccgccg   2520
acgctaaccg tacggctcaa cgtacgaaag aagaccatcc tacgacgctt gcaattagct   2580
gggcaagcaa agcttttttt ttcatcctga gtcgatcttt acgtatgtat gtttgtttaa   2640
ataaaaaggt agctaatcag ctgcttggct gtgaccccac gagctagcag ctacaaccta   2700
ctggtacatg ctgcacattt tagctgattt atgaaggtga caatatgatt ggtagggttg   2760
caatgttgac tgggcatagt gtaacaactt aagcaatggc catgggcgag tacgtgtcga   2820
gtggtgaagt tgaagggaag tttatattaa aagcaaggcc atgtcttgta ttaccttgcc   2880
tattattctg ccatatatac atactggtgt ggttctgtga agattgcttt gtttgtttga   2940
```

-continued

```
tgatactgtc actacacagc tggctgctta ttcttgtcgt gccatcgctt actttttcca   3000

attctcttta tactatccca cttttcaatg acaagacgtc catatataca tatcaagctg   3060

aaaacaagaa tgcagcagca tctatttcta ggccacctta gctttttcac gtcatttcag   3120

tcgttttata atacacgatc ttgcgatgct agtttctaag tgcatctgtg catatatgct   3180

agatgggccg tctagccact aggatcacaa ttcacaagtg catttatctg aataagttta   3240

tgaacgaata tgcctttgaa gaaatatatt gattacctca gaagatatat cactcaatgt   3300

caggcaacta gccatttcag ccgtttcaac tgttctcttg aacaggtgta tttatcttga   3360

ttaaattgaa catgtaggtc tagagactgt atgaaaacca aatatacttt accaaatgtt   3420

aggagaagac acttggcaaa cgagagtttt gctgagcacc tgaggacatc actcagcaaa   3480

gacataactg tgtcgacata aatacataac gacggtcgtc ggttgttgac ggcgctttaa   3540

cgagttgagt gttgatgttg gccgagagtt taactatcga caaataagtc tcggcataat   3600

atccttacaa taccatatat aatatgcatg gtctttggca tgcctcttat tatagctata   3660

tatgttaggt gtgtgttctt ataccaaagc aagaaactga caggtgacaa gagaagacaa   3720

ctgttgcaac acgctaagac aactgttgca acttatgtct ggccggatgg ttgtgttaca   3780

attacaacac gctaagacaa ctgttgcatg taaccttctt ttaattgggg gttagttata   3840

gcctaaccct aacacttcca tcggaatgta agtgttcatt taccacgtac cctctccatt   3900

ccaaaatcta aatttacgct tcacccaata ggaagaatga tataattaag cagcaaaggc   3960

aatcctaata gtgtatcacg ctagaatgat attgacacct cagctgctgg atctattgca   4020

gcattaattc aaaatagaaa gtgataataa tactgtccca aattaaaatt cgttttagct   4080

aatcaatgag ctcatacaat atttgtatat gttttatatg tgtataggtt catccttatt   4140

tatttaaata gagactaaaa tgactaatat tttaggacga ccgaggtagt accggccaat   4200

gcaagtcaca tatgagtgga agtgtacgca tcaaattcca ggacaaatat gcgtgttgtg   4260

gtaaaaccgt acctgagctt gatcatttcg ttgcctgtat taaacagttc tagaaaattc   4320

agataaatac atccttatcc tcatatacta atataaaata cgagtttcgt aaccctctcc   4380

acagtagtga gggtttttcg cacgccaacg aaatataaaa aaatgcagct gtcagaattc   4440

aaattgtggc ctacaagaga gcacctgccg atcatgacta taggttatat tggtttttgt   4500

tatataaaca aactatatat atatatatat atatatatat atatatataa atagtagtga   4560

tgtacgggta actaacgagt actcttgata cgtctggtcg gatgccaggc tatcacatgc   4620

atatatagta cgacctatcg tcaggtaata cagatgcaga gataatgcaa acatatatag   4680

catatctgct ccaaaaaaga aagacgatgt gataaataca agtgaaaaaa tgaacaggca   4740

gctaggccac gctgaggcag agctgggcaa cctatcacgg cacttgtctt cctgctgtgt   4800

gtggtaccat accaagtaca gagcattgca gagtgcacag gcgctggggc caaggtggcc   4860

gcaagacaaa catggcgtgg agcgggacag ggcacggatt tgatagggta agttggtcct   4920

tgccacagag cctagctcca cgagaaaccc gctggcctgt cgacgtgtcg atcctgcgat   4980

cgtctcggca gcccccacac ccccgtcttg ttgggtctcg actctcgaca gggtggtggc   5040

aaatccatga attatctaca cctgtgagta cgtacgaggt ggatgcgatc tgcctcctcc   5100

gggccctctg taatatttat aaaggcattg ccaattgcag ctgcagacat cctggactcc   5160

gatgtgtgga ccaaagaaag acgcgtagct agggtagagc tgcatgcgtc cagtctcctg   5220

ttatggccgc cggcccgcca agcacactgc acacgcgcac cttctagcta gctactccgc   5280

ttctgtctgg aatggctgga atatataata tgctatgcta ccgtggagcc gagctctagc   5340
```

-continued atcagatgtg cttgctgctc cggttaacac ttgtgtctgc acgtacaaat gaatgccggc 5400
acaggacaca acagttggca gtacaagctg catcgagatg aacacaatgg tgtgtacaag 5460
cccatgtgtc attgtacaaa gttgccctgc agtgcgagta ccagaaccgg agcctttgtt 5520
ctcctacaac aggccctaga acagcatgca gcacgtagat acgctcctgg cgcatggccc 5580
acgtccgatg tccattgcac cagcacaaca tgtgtcgtcc atcatccacg actcgtgccc 5640
tcaggggtcc agtccagcag gtgaacaatc aagacactct gcatcttgtc aaagacaaca 5700
gcgtgcagtg cttgaatcct ctcatacatg cataccacct cccagctttt gcccaaagat 5760
cgaattgtca aaggcggcaa cagcatgcca gcttttgccc ggagaaagat gtaccgttgc 5820
caatgtagct ggatgttatg tagtaccgga aaacaattaa gcaattttgg gtactgtacc 5880
atcccacagt tatgtgctcc agtcacctac taaacacaat agtatatatt gctgctctag 5940
aggccacctg ttatattgcc atggct 5966

<210> SEQ ID NO 68
<211> LENGTH: 60
<212> TYPE: PRT
<213> ORGANISM: Artificial Sequence
<220> FEATURE:
<223> OTHER INFORMATION: Consensus sequence
<221> NAME/KEY: VARIANT
<222> LOCATION: 14, 26, 29, 42, 44, 54, 56, 57
<223> OTHER INFORMATION: Xaa = Any Amino Acid

<400> SEQUENCE: 68

Met Gly Arg Gly Lys Ile Glu Ile Lys Arg Ile Glu Asn Xaa Thr Asn
1 5 10 15

Arg Gln Val Thr Tyr Ser Lys Arg Arg Xaa Gly Ile Xaa Lys Lys Ala
20 25 30

Arg Glu Leu Thr Val Leu Cys Asp Ala Xaa Val Xaa Ile Ile Met Phe
35 40 45

Ser Ser Thr Gly Lys Xaa His Xaa Xaa Cys Ser Pro
50 55 60